(12) United States Patent
Laurent et al.

(10) Patent No.: US 9,822,120 B2
(45) Date of Patent: Nov. 21, 2017

(54) PROTEIN KINASE INHIBITORS

(71) Applicant: Pharmascience Inc., Montreal, Québec (CA)

(72) Inventors: Alain Laurent, Montreal (CA); Yannick Rose, Montreal (CA)

(73) Assignee: Pharmascience Inc., Montreal, Quebec (CA)

(*) Notice: Subject to any disclaimer, the term of this patent is extended or adjusted under 35 U.S.C. 154(b) by 0 days.

(21) Appl. No.: 15/037,923

(22) PCT Filed: Nov. 20, 2014

(86) PCT No.: PCT/CA2014/000842
§ 371 (c)(1),
(2) Date: May 19, 2016

(87) PCT Pub. No.: WO2015/074138
PCT Pub. Date: May 28, 2015

(65) Prior Publication Data
US 2016/0280711 A1   Sep. 29, 2016

(30) Foreign Application Priority Data
Nov. 21, 2013   (CA) ..................................... 2833867

(51) Int. Cl.
| | | |
|---|---|---|
| A61K 31/4985 | (2006.01) | |
| C07D 487/04 | (2006.01) | |
| A61K 31/506 | (2006.01) | |
| A61K 45/06 | (2006.01) | |

(52) U.S. Cl.
CPC ........ *C07D 487/04* (2013.01); *A61K 31/4985* (2013.01); *A61K 31/506* (2013.01); *A61K 45/06* (2013.01)

(58) Field of Classification Search
CPC .................................................. C07D 487/04
See application file for complete search history.

(56) References Cited

U.S. PATENT DOCUMENTS

| | | |
|---|---|---|
| 2008/0076921 A1 | 3/2008 | Honigberg et al. |
| 2008/0139582 A1 | 6/2008 | Honigberg et al. |
| 2009/0286768 A1 | 11/2009 | Crew et al. |

FOREIGN PATENT DOCUMENTS

| | | |
|---|---|---|
| CA | 2385769 A1 | 3/2001 |
| CA | 2779184 A1 | 11/2013 |
| CA | 2782774 A1 | 1/2014 |
| CN | 1390220 A | 1/2003 |
| WO | WO 2008/121742 A2 | 10/2008 |
| WO | WO 2012/158795 A1 | 11/2012 |

OTHER PUBLICATIONS

Bradshaw, "The Src, Syk, and Tec family kinases: Distinct types of molecular switches", Cell Signalling 22:1175-1184, 2010.
Cenni et al., "BMX and Its Role in Inflammation, Cardiovascular Disease, and Cancer", Int. Rev. Immunol. 31: 166-173, 2012.
Fabbro et al., "Targeting Cancer with Small-Molecular-Weight Kinase Inhibitors", Methods Mol. Biol. 795: 1-34, 2012.
Guryanova et al., "Non-Receptor Tyrosine Kinase BMX Maintains Self-Renewal and Tumorigenic Potential of Glioblastoma Stem Cells by Activating STAT3", Cancer Cell 19(4): 498-511, 2011.
Herman et al., "Bruton tyrosine kinase represents a promising therapeutic target for treatment of chronic lymphocytic leukemia and is effectively targeted by PCI-32765", Blood 117(23): 6287-6289, 2011.
Jin et al., "Discovery of potent, selective and orally bioavailable imidazo[1,5-a] pyrazine derived ACK1 inhibitors" Bioorganic & Medicinal Chemistry Letters 23: 979-984, 2013.
Khan et al., "Defective B Cell Development and Function in Btk-Deficient Mice", Immunity 3: 283-299, 1995.
Kim et al., "Src kinases as therapeutic targets for cancer", Nat. Rev. Clin. Oncol. 6(10): 587-589, 2009.
Kyttaris, "Kinase inhibitors: a new class of antirheumatic drugs", Drug Des. Devel. Ther. 6: 245-250, 2012.
Lee et al., "The Src-family kinase Fgr is critical for activation of mast cells and IgE-mediated anaphylaxis in mice1", J. Immunol. 187(4): 1807-1815, 2011.
Lindvall et al., "Bruton's tyrosine kinase: cell biology, sequence conservation, mutation spectrum, siRNA modifications, and expression profiling", Immunol. Rev. 203: 200-215, 2005.
Liu et al., "Bruton tyrosine kinase is essential for botrocetin/VWF-induced signaling and GPIb-dependent thrombus formation in vivo", Blood 108(8): 2596-2603, 2006.
Liu et al, "Antitumor Effects of Immunotoxiins Are Enhanced by Lowering HCK or Treatment with Src Kinase Inhibitors", Mol. Cancer Ther. 13(1): 82-89, 2013.
Manning et al., "The Protein Kinase Complement of the Human Genome", Science 298: 1912-1934, 2002.
Martin et al., "Update on lymphocyte specific kinase inhibitors: a patent survey", Expert Opin. Ther. Pat. 20(11): 1573-1593, 2010.
Mulvihill et al., "1,3-Disubstituted-imidazo[1,5-a] pyrazines as insulin-like growth-factor-I receptor (IGF-IR) inhibitors" Bioorganic & Medicinal Chemistry Letters 17: 1091-1097, 2007.
Rosen et al., "The Primary Immunodeficiencies", N. Engl. J. Med. 333(7): 431-440, 1995.

(Continued)

*Primary Examiner* — Brian McDowell
(74) *Attorney, Agent, or Firm* — Leydig, Voit & Mayer, Ltd.

(57) ABSTRACT

The present invention relates to a novel family of protein kinase inhibitors of Formula I:

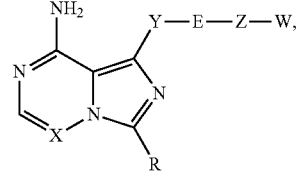

Formula I as well as to the processes of preparation of these compounds, to pharmaceutical compositions comprising them, and to their use in the treatment of proliferative, inflammatory, autoimmune or infectious diseases, disorders, or conditions in which protein kinase activity is implicated.

21 Claims, No Drawings

(56) References Cited

OTHER PUBLICATIONS

Satterthwaite et al., "The role of Bruton's tyrosine kinase in B-cell development and function: a genetic perspective", Immunol. Rev. 175: 120-127, 2000.
Smolinska et al., "Hck Tyrosine Kinase Regulates TLR4-Induced TNF and IL-6 Production via AP-1", J. Immunol. 187: 6043-6051, 2011.
International Search Report, dated Feb. 10, 2015, issued in corresponding International Application No. PCT/CA2014/000842.
International Preliminary Report on Patentability, dated Jun. 2, 2016, issued in corresponding International Application No. PCT/CA2014/000842.
Chinese State Intellectual Property Office, English Translation of Search Report in cognate Chinese Patent Application No. 2014800723992, dated Jun. 1, 2017, 2 pp.

PROTEIN KINASE INHIBITORS

FIELD OF INVENTION

The present invention relates to a novel family of protein kinase inhibitors, to the processes for preparation of these compounds, to pharmaceutical compositions comprising them, and to their use in the treatment of proliferative, inflammatory, autoimmune or infectious diseases, disorders, or conditions in which protein kinase activity is implicated.

BACKGROUND OF THE INVENTION

Protein kinases are a large group of intracellular and transmembrane signaling proteins in eukaryotic cells (Manning G. et al, (2002) Science, 298: 1912-1934). These enzymes are responsible for transfer of the terminal (gamma) phosphate from ATP to specific amino acid residues of target proteins. Phosphorylation of specific amino acid residues in target proteins can modulate their activity leading to profound changes in cellular signaling and metabolism. Protein kinases can be found in the cell membrane, cytosol and organelles such as the nucleus and are responsible for mediating multiple cellular functions including metabolism, cellular growth and differentiation, cellular signaling, modulation of immune responses, or cell death. Serine kinases specifically phosphorylate serine, or threonine residues in target proteins. Similarly, tyrosine kinases, including tyrosine receptor kinases, phosphorylate tyrosine residues in target proteins. Tyrosine kinase families include: Tec, Src, Abl, Jak, Csk, Fak, Syk, Fer, and Ack, and the receptor tyrosine kinase subfamilies including EGFR, FGFR, VEGFR, RET and Eph.

Kinases exert control on key biological processes related to health and disease. Furthermore, aberrant activation or excessive expression of various protein kinases are implicated in the mechanism of multiple diseases and disorders characterized by benign and malignant proliferation, as well as diseases resulting from inappropriate activation of the immune system (Kyttaris V. C., Drug Des. Devel. Ther., 2012, 6:245-50 and Fabbro D. et al. Methods Mol. Biol., 2012, 795:1-34). Thus, inhibitors of select kinases or kinase families are expected to be useful in the treatment of cancer, vascular disease, autoimmune diseases, and inflammatory conditions including, but not limited to: solid tumors, hematological malignancies, thrombus, arthritis, graft versus host disease, lupus erythematosus, psoriasis, colitis, illeitis, multiple sclerosis, uveitis, coronary artery vasculopathy, systemic sclerosis, atherosclerosis, asthma, transplant rejection, allergy, dermatomyositis, pemphigus, and the like.

Tec kinases are a family of non-receptor tyrosine kinases predominantly, but not exclusively, expressed in cells of hematopoietic origin (Bradshaw J. M. Cell Signal. 2010,22: 1175-84). The Tec family includes Tec, Bruton's tyrosine kinase (Btk), inducible T-cell kinase (Itk), resting lymphocyte kinase (Rlk/Txk), and bone marrow-expressed kinase (Bmx/Etk). Btk is important in B-cell receptor signaling and regulation of B-cell development and activation (W. N. Khan et al. Immunity, 1995, 3:283-299 and Satterthwaite A. B. et al. Immunol. Rev. 2000,175: 120-127). Mutation of the gene encoding BTK in humans leads to X-linked agammaglobulinemia which is characterized by reduced immune function, including impaired maturation of B cells, decreased levels of immunoglobulin and peripheral B cells, diminished T-cell independent immune response (Rosen F. S. et al., N. Engl. J. Med.,1995, 333:431-440; and Lindvall J. M. et al. Immunol. Rev. 2005, 203:200-215). Btk is activated by Src-family kinases and phosphorylates PLC gamma leading to effects on B-cell function and survival. Additionally, Btk is important in signal transduction in response to immune complex recognition by macrophage, mast cells and neutrophils. Btk inhibition is also important in survival of lymphoma cells (Herman SEM. Blood, 2011, 117:6287-6289) suggesting that inhibition of Btk may be useful in the treatment of lymphomas. As such, inhibitors of Btk and related kinases are of great interest as anti-inflammatory as well as anti-cancer agents. Btk is also important for platelet function and thrombus formation suggesting that Btk-selective inhibitors may prove to be useful antithrombotic agents (Liu J. Blood, 2006,108:2596-603).

Bmx, another Tec family member which has roles in inflammation, cardiovascular disease, and cancer (Cenni B. et al. Int. Rev. Immunol., 2012, 31: 166-173) is also important for self-renewal and tumerogenic potential of glioblastoma stem cells (Guryanova O. A. et al. Cancer Cell 2011, 19:498-511). As such, Bmx inhibitors are expected to be useful in the treatment of various diseases including cancer, cardiovascular disease and inflammation.

The SRC family of tyrosine kinases includes cSRC, Lyn, Fyn, Lck, Hck, Fgr, Blk, Syk, Yrk and Yes. cSRC is critically involved in signaling pathways involved in cancer and is often over-expressed in human malignancies (Kim L. C. et al. (2009) Nat. Rev. Clin. Oncol. 6:587-9). cSRC is involved in signaling downstream of growth factor receptor tyrosine kinases and regulates cell cycle progression suggesting that cSRC inhibition would impact cancer cell proliferation. Furthermore, Src inhibitors or downregulation of Hck sensitize tumor cells to immunotoxins (Lui X. F., Mol. Cancer Ther., 2013, Oct. 21).

Inhibition of SRC family members may be useful in treatments designed to modulate immune function. SRC family members, including Lck, regulate T-cell receptor signal transduction which leads to gene regulation events resulting in cytokine release, survival and proliferation. Thus, inhibitors of Lck may be useful immunosuppressive agents with potential application in graft rejection and T-cell mediated autoimmune disease (Martin et al. Expert Opin. Ther. Pat., 2010, 20:1573-93). The Src family member HCK is implicated in regulation of cytokine production suggesting that inhibition of this kinase may be useful in treatment of inflammatory disease (Smolinska M. J. et al. J. Immunol., 2011, 187:6043-51). Additionally, the Src family kinase Fgr is critical for activation of mast cells and IgE-mediated anaphylaxis suggesting that this kinase is a potential therapeutic target for allergic diseases (Lee J. H. et al. J. Immunol., 2011;187:1807-15).

Inhibition of kinases using small molecule inhibitors has successfully led to several approved therapeutic agents used in the treatment of a variety of diseases disorders and conditions. Herein, we disclose a novel family of kinase inhibitors. Further, we demonstrate that modifications in compound substitution can influence kinase selectivity and therefore the biological function of that agent.

SUMMARY OF THE INVENTION

The present invention relates to a novel family of kinase inhibitors. Compounds of this class have been found to have inhibitory activity against members of the Tec, or Scr protein kinase families.

One aspect of the present invention is directed to a compound of Formula I:

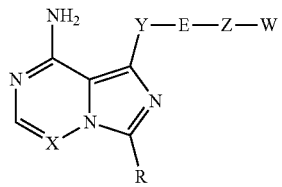

Formula I or pharmaceutically acceptable salts, solvates, solvates of salts, stereoisomers, tautomers, isotopes, prodrugs, complexes or biologically active metabolites thereof, wherein
X is CH or N;
R is selected from the group consisting of:
1) hydrogen,
2) alkyl,
3) heteroalkyl,
4) carbocyclyl,
5) heterocyclyl,
6) aryl, or
7) heteroaryl,
wherein the alkyl, heteroalkyl, carbocyclyl, heterocyclyl, aryl, or heteroaryl are optionally substituted;
Y is

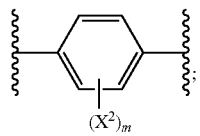

E is oxygen;
Z is

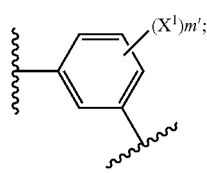

W is
1) —OCH$_2$R$^1$, or
2) —CH$_2$OR$^1$, wherein
R$^1$ is substituted or unsubstituted aryl, substituted or unsubstituted heteroaryl;
wherein Y-E-Z-W is

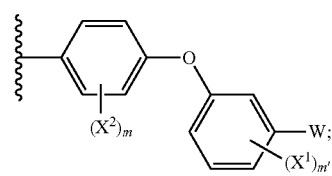

X$^1$ and X$^2$ are independently hydrogen or halogen;
m is an integer from 0 to 4,
m' is an integer from 0 to 4.

Another embodiment of the present invention includes compounds of Formula I, wherein W is selected from the group consisting of:

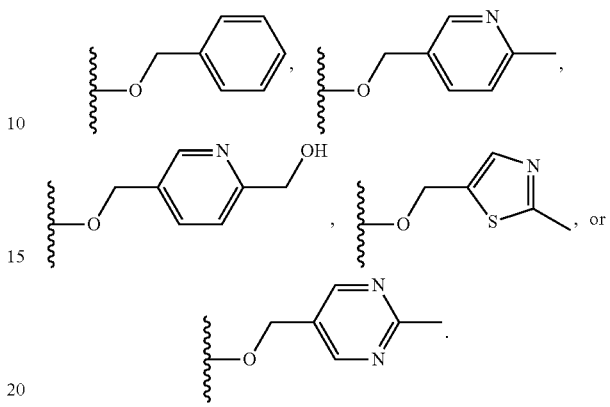

Another embodiment of the present invention includes compounds of Formula I, wherein Z is

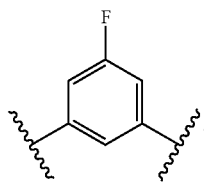

Other embodiments of the present invention includes compounds of Formula I, wherein Y is

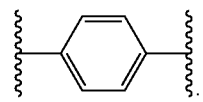 [SMILES: *c1ccc(*)cc1]

Another embodiment of the present invention includes compounds of Formula I, wherein R is selected from the group consisting of:

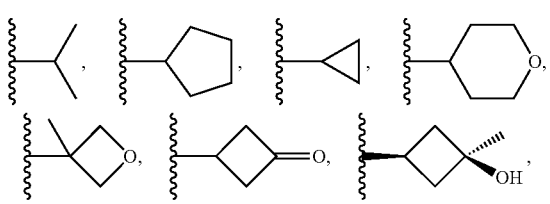

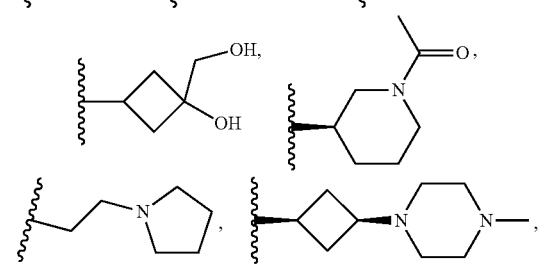

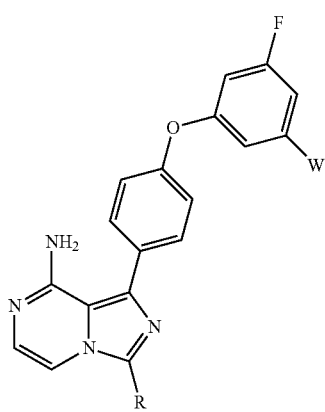

Another embodiment of the present invention includes compounds of Formula II:

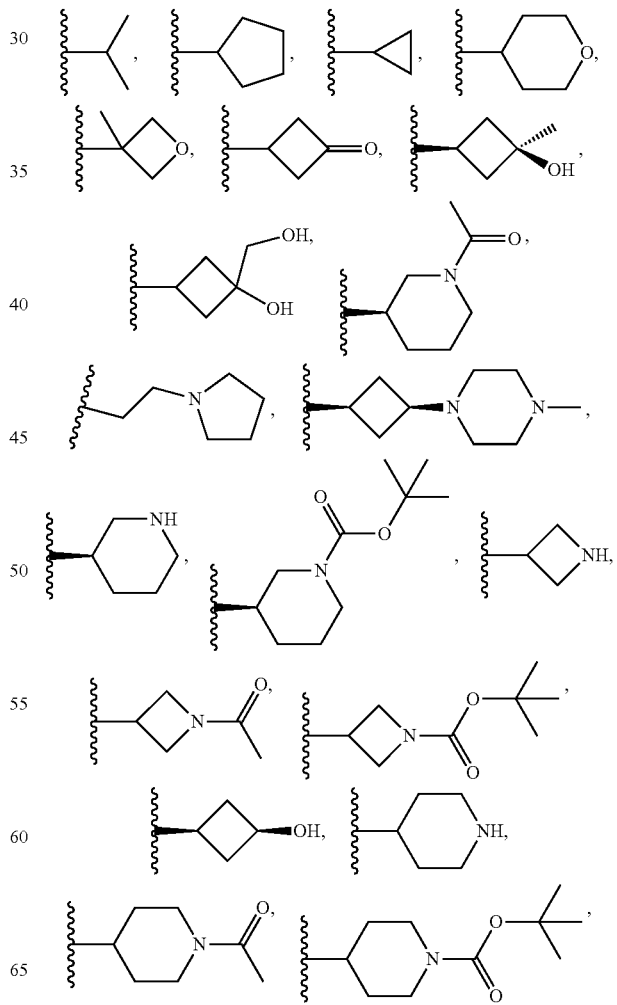

or a pharmaceutically acceptable salts, solvates, solvates of salts, stereoisomers, tautomers, isotopes, prodrugs, complexes or biologically active metabolites thereof, wherein R is selected from the group consisting of:
1) hydrogen,
2) alkyl,
3) heteroalkyl,
4) carbocyclyl,
5) heterocyclyl,
6) aryl, or
7) heteroaryl,
wherein the alkyl, heteroalkyl, carbocyclyl, heterocyclyl, aryl, or heteroaryl are optionally substituted;
W is —OCH$_2$R$^1$ or —CH$_2$OR$^1$,
wherein R$^1$ is substituted or unsubstituted aryl, substituted or unsubstituted heteroaryl.

Another embodiment of the present invention includes compounds of Formula II, wherein W is selected from the group consisting of:

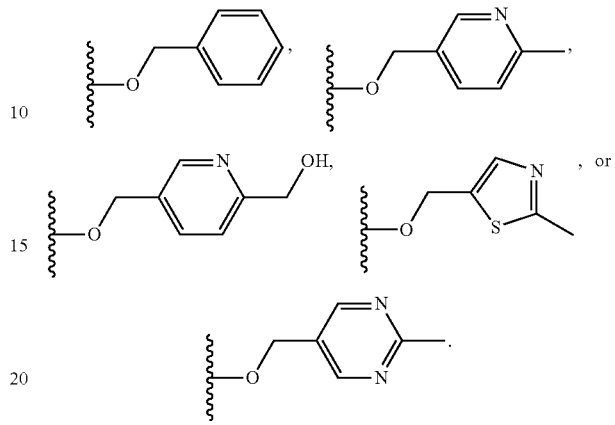

Another embodiment of the present invention includes compounds of Formula II, wherein R is selected from the group consisting of:

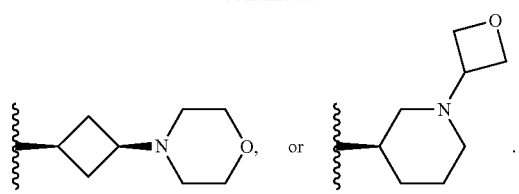

Another aspect of the present invention provides Intermediates and their synthesis related to a process of production of compounds of the invention as defined herein, or a pharmaceutically acceptable salt, or solvate, solvates of salts, stereoisomers, tautomers, isotopes, prodrugs, complexes or biologically active metabolites thereof, or a pharmaceutical composition as defined herein.

In another aspect, the present invention relates to a process for preparing a compound of Formula I, or Formula II, wherein the process comprises:

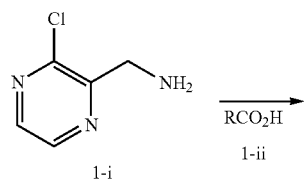

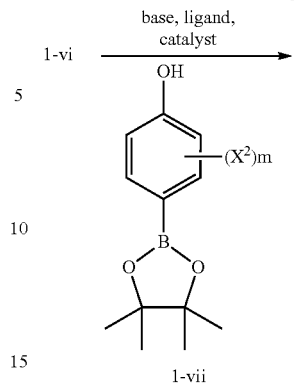

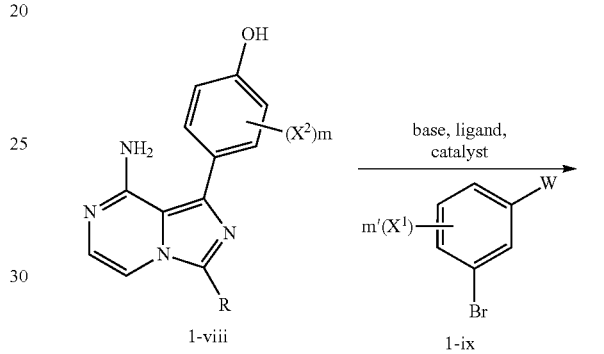

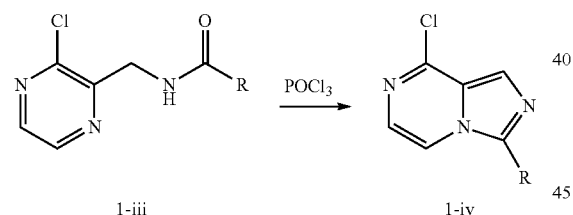

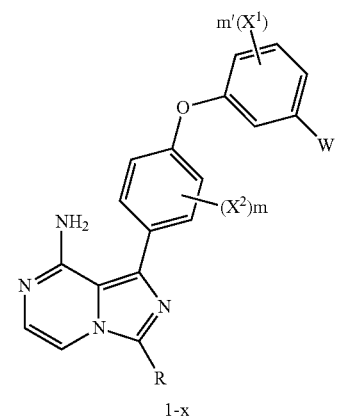

Another aspect of the present invention provides the process for preparing a compound of Formula I, or Formula II, wherein the process comprises:

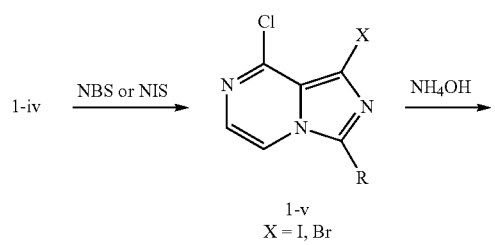

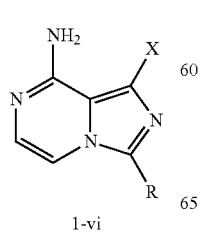

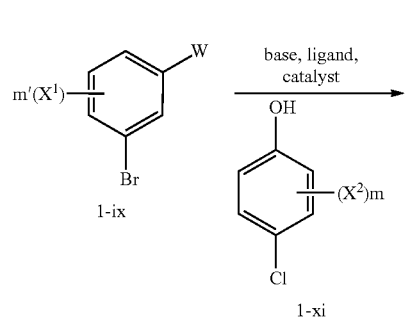

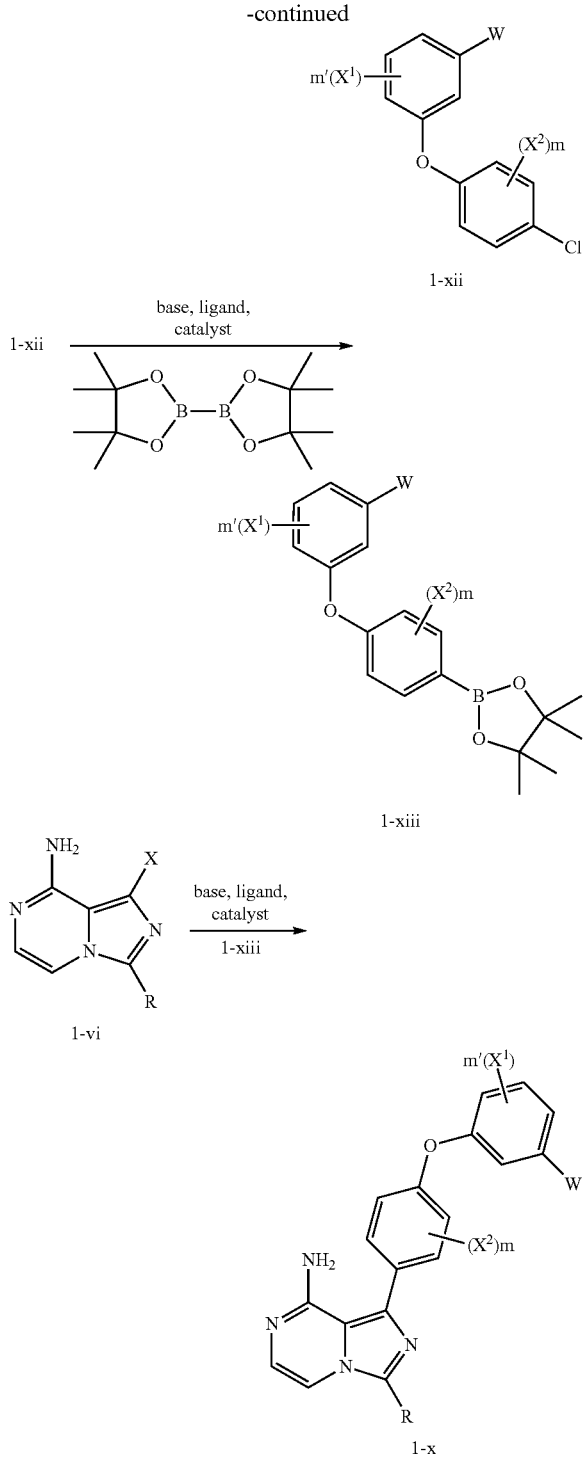

Another aspect of the present invention provides a pharmaceutical composition comprising a compound of Formula I, or Formula II, or a pharmaceutically acceptable salts, solvates, solvates of salts, stereoisomers, tautomers, isotopes, prodrugs, complexes or biologically active metabolites thereof, and at least one pharmaceutically acceptable carrier, diluents, or excipient.

In another aspect, the present invention relates to a compound of the invention as defined herein, or a pharmaceutically acceptable salt, or solvate, solvates of salts, stereoisomers, tautomers, isotopes, prodrugs, complexes or biologically active metabolites thereof, or a pharmaceutical composition as defined herein, for use in therapy.

In another aspect, the present invention relates to a compound of the invention as defined herein, or a pharmaceutically acceptable salt, or solvate thereof, or a pharmaceutical composition, as defined herein, for use in the treatment of subjects suffering from a protein kinase mediated diseases or conditions.

Another aspect of the present invention provides a use of the compound of Formula I, or Formula II, as an inhibitor of protein kinase, more particularly, as an inhibitor of members of the Tec family of kinases.

A further aspect of the present invention provides a use of the compound of Formula I, or Formula II, as an inhibitor of protein kinase, more particularly, as an inhibitor of members of the Src family of kinases.

Another aspect of the present invention provides a use of the compound of Formula I, or Formula II, as an inhibitor of protein kinase, more particularly, as an inhibitor wherein the disease is a protein kinase mediated disease, disorder, or condition in which Btk kinase activity is implicated.

In another aspect, the present invention relates to the use of a compound of the invention as defined herein, or a pharmaceutically acceptable salt or solvate thereof, in the manufacture of a medicament for use in the treatment of subjects suffering from a protein kinase mediated diseases or conditions.

A further aspect of the present invention provides a pharmaceutically acceptable salt, or solvate thereof, for use in manufacturing of a pharmaceutical composition, for use in treatment of proliferative, inflammatory, infectious, or autoimmune diseases.

Another aspect of the present invention provides a compound, or pharmaceutically acceptable salts, or solvates thereof, or a pharmaceutical composition, as defined in present invention, for use in the treatment of a proliferative disorder, inflammatory, or autoimmune disease. In a particular embodiment, the proliferative disorder, inflammatory, or autoimmune disease is cancer. More particular, is a human cancer.

A further aspect of the present invention provides the use of a compound, or a pharmaceutically acceptable salt, or solvate thereof, in the manufacture of a medicament for use in the treatment of a proliferative disorder, such as cancer.

Another aspect of the present invention provides a compound of Formula I, or Formula II, or a pharmaceutically acceptable salts, solvates, solvates of salts, stereoisomers, tautomers, isotopes, prodrugs, complexes, or biologically active metabolites thereof, for use in the treatment of a proliferative, inflammatory, or autoimmune diseases, or disorder state in combination with an agent selected from: an estrogen receptor modulator; an androgen receptor modulator; a retinoid receptor modulator; a cytotoxic agent; an anti-proliferative agent comprises adriamycin, dexamethasone, vincristine, cyclophosphamide, fluorouracil, topotecan, taxol, interferons, or platinum derivatives; an anti-inflammatory agent comprises corticosteroids, TNF blockers, IL-1 RA, azathioprine, cyclophosphamide, or sulfasalazine; a prenyl-protein transferase inhibitor; an HMG-CoA reductase inhibitor; an HIV protease inhibitor; a reverse transcriptase inhibitor; an angiogenesis inhibitor comprises sorafenib, sunitinib, pazopanib or everolimus; an immunomodulatory or immunosuppressive agents comprises cyclosporin, tacrolimus, rapamycin, mycophenolate mofetil, interferons, corticosteroids, cyclophophamide, azathioprine, or sulfasalazine; a PPAR-γ agonist comprising thiazolidinediones; a PPAR-δ agonist; an inhibitor of inherent multidrug resistance; an agent for the treatment of anemia, comprising erythropoiesis-stimulating agents, vitamins or iron supplements; an anti-emetic agent including 5-HT3 receptor antagonists, dopamine antagonists, NK1 receptor antagonist, H1 histamine receptor antagonists, cannabinoids, benzodiazepines, anticholinergic agents or steroids; an agent for the treatment of neutropenia; an immunologic-enhancing agents; a proteasome inhibitors; an HDAC inhibitors; an inhibitor of the chemotrypsin-like activity in the proteasome; a E3 ligase inhibitors; a modulator of the immune system including interferon-alpha, Bacillus Calmette-Guerin (BCG), or ionizing radiation (UVB) that can induce the release of cytokines, interleukins, TNF, or induce release of death receptor ligands including TRAIL; a modulator of death receptors TRAIL or TRAIL agonists including humanized antibodies HGS-ETR1 or HGS-ETR2; neurotrophic factors selected from cetylcholinesterase inhibitors, MAO inhibitors, interferons, anti-convulsants, ion channel blockers, or riluzole; Anti-Parkinsonian agents comprising anticholinergic agents or dopaminergic agents, including dopaminergic precursors, monoamine oxidase B inhibitors, COMT inhibitors, dopamine receptor agonists; agents for treating cardiovascular disease comprises beta-blockers, ACE inhibitors, diuretics, nitrates, calcium channel blockers, or statins; agents for treating liver disease comprises corticosteroids, cholestyramine, or interferons; anti-viral agents, including nucleoside reverse transcriptase inhibitors, non-nucleoside reverse transcriptase inhibitors, protease inhibitors, integrase inhibitors, fusion inhibitors, chemokine receptor antagonists, polymerase inhibitors, viral proteins synthesis inhibitors, viral protein modification inhibitors, neuraminidase inhibitors, fusion or entry inhibitors; agents for treating blood disorders comprising corticosteroids, anti-leukemic agents, or growth factors; agents for treating immunodeficiency disorders comprising gamma globulin, adalimumab, etarnecept or infliximab; a HMG-CoA reductase inhibitors including torvastatin, fluvastatin, lovastatin, pravastatin, rosuvastatin, simvastatin, or pitavastatin, or in combination, or sequentially with radiation, or with at least one chemotherapeutic agent.

More preferably the medicament is for the treatment of a proliferative disorder or disease state in combination with a death receptor agonist.

Another aspect of the present invention provides a compound, or pharmaceutically acceptable salts, or solvates thereof, or a pharmaceutical composition as defined in present invention, for use in the treatment of diseases or disorders selected from: cancer, myeloproliferative disorders, lung fibrosis, hepatic fibrosis, cardiovascular diseases: cardiac hypertrophy, cardiomyopathy, restenosis; thrombosis, heart attacks or stroke; alopecia, emphysema; atherosclerosis, psoriasis or dermatological disorders, lupus, multiple sclerosis, macular degeneration, asthma, reactive synoviotides, viral disorders; CNS disorders; auto-immune disorders: glomerulonephritis or rheumatoid arthritis; hormone-related diseases, metabolic disorders; inflammatory diseases; infectious or fungal diseases, malaria or parasitic disorders.

Another aspect of the present invention provides a compound, or pharmaceutically acceptable salts, or solvates thereof, or a pharmaceutical composition, as defined in present invention, for use in the manufacture of a medicament for the treatment of: arthritis, tenosynovial giant cell tumour, pigmented villonodular synovitis, and other reactive synoviotides, bone metastases formation and progression, acute myeloid leukemia, or human cancer, or select subsets of cancer, for example breast tumours and gastric cancer by inhibition of kinase activity.

In another aspect, the present invention relates to a method of treating a disease or condition associated with protein kinase activity, said method comprising administering to a subject a therapeutically effective amount of a compound of the invention as defined herein, or a pharmaceutically acceptable salt, or solvate thereof, or a pharmaceutical composition as defined herein.

In another aspect, the present invention provides a method of treating a proliferative disorder, said method comprising administering to a subject a therapeutically effective amount of a compound, or a pharmaceutically acceptable salt, or solvate thereof, or a pharmaceutical composition, as defined herein. In a particular embodiment, the proliferative disorder is a cancer.

Another aspect of the present invention provides a method of modulating kinase function, the method comprising contacting a cell with a compound of the present invention in an amount sufficient to modulate the enzymatic activity of a given kinase, or kinases from Tec or Src families, thereby modulating the kinase function.

A further aspect of the present invention provides a method of inhibiting cell proliferation, or survival in vitro or in vivo, said method comprising contacting a cell with an effective amount of a compound as defined herein, or a pharmaceutically acceptable salt, or solvate thereof.

In one embodiment, the present invention provides a method of producing a protein kinase inhibitory effect in a cell or tissue, said method comprising contacting the cell or tissue with an effective amount of a compound, or a pharmaceutically acceptable salt or solvate thereof.

In other embodiment, the present invention provides a method of producing a protein kinase inhibitory effect in vivo, said method comprising administering to a subject an effective amount of a compound, or a pharmaceutically acceptable salt, or solvate thereof.

In other embodiment, the present invention provides a method of producing a protein kinase inhibitory effect in vivo, said method comprising administering to a subject an effective amount of a compound, or a pharmaceutically acceptable salt, or solvate thereof. The administration may be by any suitable route of administration, such as parenteral or oral. The dosage unit may be any suitable amount, for example, the dosage unit for parenteral or oral administration may contain from about 50 mg to about 5000 mg of a compound of Formula I, or Formula II, or a pharmaceutical acceptable salt, or solvate thereof. The compounds of the present invention may be administered 1 to 4 times a day. A dosage of between 0.01-100 mg/kg body weight/day of the compounds of the present invention can be administered to a patient receiving these compositions.

The compounds of the present invention may be used alone or in combination with one or more other therapeutic agents. The combination may be achieved by way of the simultaneous, sequential or separate dosing of the individual components of treatment. Such combination products employ the compounds of this invention within the dose range described hereinbefore and the other pharmaceutically active agent within its approved dose range.

Another aspect of the present invention provides a method of modulating the target kinase function. The method comprising:

a) contacting a cell with a compound of the present invention in an amount sufficient to modulate the target kinase function, thereby;

b) modulating the target kinase activity and signaling.

The present invention further provides a method of preparation of a compound, or a pharmaceutically acceptable salt, or solvate thereof, as defined herein.

Another aspect of the present invention provides a probe, the probe comprising a compound of Formula I, or Formula II, labeled with a detectable label or an affinity tag. In other words, the probe comprises a residue of a compound of Formula I, or Formula II covalently conjugated to a detectable label. Such detectable labels include, but are not limited to, a fluorescent moiety, a chemiluminescent moiety, a paramagnetic contrast agent, a metal chelate, a radioactive isotope-containing moiety, or biotin.

DETAILED DESCRIPTION OF PREFERRED EMBODIMENTS

The present invention relates to novel kinase inhibitors. These compounds are found to have activity, as inhibitors of protein kinases, including members of the Src or Tec kinase families.

Compounds of the present invention may be formulated into a pharmaceutical composition, which comprises an effective amount of a compound of the present invention, with at least one pharmaceutically acceptable diluent, carrier, or excipient.

The term "pharmaceutically effective amount" refers to any amount of the composition for the prevention and treatment of humans, or animals that is effective in treating a disease, disorder, or condition associated with protein kinase activity.

Pharmaceutical Compositions

According to the present invention there is provided a pharmaceutical composition which comprises a compound of Formula I, Formula II, combinations thereof, or a pharmaceutically acceptable salt, solvate, solvates of salts, stereoisomers, tautomers, isotopes, prodrugs, complexes, biologically active metabolites thereof or mixtures of the compounds of the present invention, in association with at least one pharmaceutically acceptable excipient, diluents, or carrier.

The pharmaceutical compositions may be in a conventional pharmaceutical form suitable for oral administration (e.g., tablet, capsule, granules, powder, liquid solution, suspension or syrup); for parenteral administration (e.g., cutaneous, subcutaneous, intramuscular, intraperitoneal, intravenous, intra-arterial, intra-cerebral, intraocular injection, or infusion); suppository rectal or vaginal; bronchial, nasal, topical, buccal, sub-lingual, transdermal, or drop infusion preparations, inhalation or insufflations, eye lotion or liquid aerosol. Regardless of the route of administration selected, the compounds may be formulated into pharmaceutically acceptable dosage forms by conventional methods known to those skilled in the art.

In the development of a dosage form formulation, the choice of the core excipients is extremely important. Several aspects of the finished dosage form must be considered such as the nature of the active pharmaceutical ingredient (API), the intended delivery method of the API (immediate release, modified, sustained, extended, delayed release etc), and the manufacturing process.

A non-limiting list of pharmaceutical compositions comprising a compound of Formula I or Formula II (or combinations of the inventive compounds), according to the present invention, and at least one pharmaceutically acceptable excipient, such as a binder, a disintegrating agent, a lubricant, a diluents, a solubilizing agent, an emulsifier, a coating agent, a cyclodextrin or buffer, for use in formulation of suitable release dosage forms: "prolonged release", "extended release", "modified release", "delayed release", "sustained release", or "immediate release", "orally disintegrating tablets", or "sustained release parenteral depot" pharmaceutical compositions.

There are different dosage forms with plurality of "controlled release" pharmaceutical compositions, particularly "prolonged release", "extended release", "modified release", "delayed release", or "sustained release" compositions. Examples for controlled release pharmaceutical compositions are immediate release pharmaceutical compositions, enteric coated pharmaceutical compositions, pulsed release pharmaceutical compositions, or sustained release pharmaceutical compositions.

An oral "controlled release pharmaceutical composition" means a pharmaceutical composition including at least one active pharmaceutical ingredient which is formulated with at least one pharmaceutically acceptable film forming polymer, and optionally with at least one pharmaceutically acceptable excipient, where the pharmaceutical composition shows a pH-dependent. or a pH-independent reproducible release profile.

The term "oral controlled release pharmaceutical composition", as referred to herein, is defined to mean oral pharmaceutical compositions which when administered releases the active ingredient at a relatively constant rate, and provide plasma concentrations of the active ingredient that remain substantially invariant with time within the therapeutic range of the active ingredient over a 24-hour period, and encompasses "prolonged release", "extended release", "modified release", "delayed release" or "sustained release" compositions.

The term "modified release", as referred to herein, means that the escape of the drug from the tablet has been modified in some way. Usually, this is to slow the release of the drug so that the medicine doesn't have to be taken too often, and therefore improves compliance. The other benefit from modifying release is that the drug release is controlled, and there are smaller peaks, and troughs in blood levels therefore reducing the chance of peak effects, and increasing the likelihood of therapeutic effectiveness for longer periods of time.

The term "continuous release", means that a term applied to a drug that is designed to deliver a dose of a medication over an extended period. The most common device for this purpose is a soft, soluble capsule containing minute pellets of the drug for release at different rates in the GI tract, depending on the thickness and nature of the oil, fat, wax, or resin coating on the pellets. Another system consists of a porous plastic carrier, impregnated with the drug, and a surfactant to facilitate the entry of GI fluids that slowly leach out of the drug. Ion exchange resins that bind to drugs and liquids containing suspensions of slow-release drug granules, are also used to provide medication over an extended period.

The term "pulsatile release", means that a drug is delivered in one, or more doses that fluctuate between a maximum and minimum dose, over a predetermined time intervals. This can be represented by a dose release profile having one or more distinct peaks, or valleys. However, two or more pulsed releases may produce an overlapping, overall, or composite release profile that appears, or effectively is constant. The need for pulsatile release may include the desire to avoid drug degradation in the stomach, or first pass metabolism. Pulsatile release can be achieved via coating of multiparticulates with pH dependent, and/or barrier membrane coating systems, followed by blending of the multiparticulates to achieve desired release profiles.

The term "delayed" release", refers to the onset of release in relationship to administration of the drug. "Delayed", means that the release of drug is postponed, and begins, or is triggered some period of time after administration (e.g., the lag time), typically a relatively long period of time, e.g. more than one hour.

The term "immediate release", means that oral pharmaceutical compositions, which when administered release the active ingredient within a small period of time, typically less than 45 minutes after administration. Oral formulations for immediate release drug delivery system is a conventional type of drug delivery system that designed to disintegrate, and release their pharmaceutically active ingredient with no rate controlling features, such as special coatings and other techniques.

The term "Orally Disintegrating Tablets" (ODT), refers to the tablet that have a disintegration time less than 60 seconds, with good mouth feel and friability that did not exceed 1%. Orally Disintegrating Tablet (ODT) allows to improve patient compliance, in particular with pediatric, geriatric, and institutionalized patients, or patients with chemotherapy-induced nausea.

Oral dosage forms, which may be employed with the present invention include: tablets, granules, spheroids, or pellets in a capsule, or in any other suitable solid form.

A "depot formulation" may be formulated to provide slow absorption of the molecules of Formula I, or Formula 2, or combinations thereof, or pharmaceutically acceptable salts, derivatives, isomers, polymorphs, solvates, hydrates, analogues, enantiomers, tautomeric forms, or mixtures thereof from the site of administration, often keeping therapeutic levels of the molecule, or an active metabolite in the patient's system for days or weeks at a time. Alternatively, a depot formulation may provide convenience for a patient in need of chronic medication. By delivering molecules of the present invention without exposure to the GI tract. Moreover, a depot formulation may provide better compliance due to the infrequent dosing regimen and convenience. Additional characteristics of a depot formulation that will enhance patient compliance are good local tolerance at the injection site and ease of administration.

Although the dosage form will vary depending on the symptoms, age, and body weight of the patient, the nature and severity of the disorder to be treated or prevented, the route of administration, and the form of the drug. In general a daily dosage form 0.01 to 2000 mg of the compound is recommended for an adult human patient, and this may be administered in a single dose, or in divided doses. The amount of active ingredient, which can be combined with at least one carrier material, to produce a single dosage form will generally be that amount of the compound which produces a therapeutic effect.

The time of administration, or amount of the composition that will yield the most effective results in terms of efficacy of treatment, in a given patient will depend upon the activity, pharmacokinetics, and bioavailability of a particular compound, physiological condition of the patient (including age, sex, disease type, and stage, general physical condition, responsiveness to a given dosage form, and type of medication), route of administration, etc.

The term "pharmaceutically acceptable", is employed herein to refer to those ligands, materials, compositions, or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier", as used herein means a pharmaceutically acceptable material, composition, or vehicle, such as a liquid or solid filler, diluent, excipient, solvent, or encapsulating material. Each carrier must be acceptable in the sense of being compatible with the other ingredients of the formulation, including the active ingredient, and not injurious, or harmful to the patient. Some examples of materials which can serve as pharmaceutically acceptable carriers include: (1) sugars, such as lactose, glucose, or sucrose; (2) starches, such as corn starch, potato starch, and substituted or unsubstituted β-cyclodextrin; (3) cellulose, and its derivatives, such as sodium carboxymethyl cellulose, ethyl cellulose, or cellulose acetate; (4) powdered tragacanth; (5) malt; (6) gelatin; (7) talc; (8) excipients, such as cocoa butter or suppository waxes; (9) oils, such as peanut oil, cottonseed oil, safflower oil, sesame oil, olive oil, corn oil, or soybean oil; (10) glycols, such as propylene glycol; (11) polyols, such as glycerin, sorbitol, mannitol, or polyethylene glycol; (12) esters, such as ethyl oleate or ethyl laurate; (13) agar; (14) buffering agents, such as magnesium hydroxide or aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salt" refers to the relatively non-toxic, inorganic and organic acid addition salts of the compound(s). These salts can be prepared in situ during the final isolation and purification of the compound(s), or by separately reacting a purified compound(s) in its free base form, with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19).

The term "halo" or "halogen" refers to chlorine, bromine, fluorine, or iodine. Fluorine is a preferred halogen.

The pharmaceutical compositions of the present invention may be obtained by conventional procedures using conventional pharmaceutical excipients, well known in the art.

In other cases, the compounds of the present invention may contain one or more acidic functional groups and, thus, are capable of forming pharmaceutically acceptable salts with pharmaceutically acceptable bases, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al.).

As used herein, the term "affinity tag", means a ligand or group, linked either to a compound of the present invention, or to a protein kinase domain that allows the conjugate to be extracted from a solution.

The term "alkyl", refers to substituted or unsubstituted saturated hydrocarbon groups, including straight-chain alkyl, and branched-chain alkyl groups, including haloalkyl groups, such as trifluoromethyl and 2,2,2-trifluoroethyl, etc. Representative alkyl groups include methyl, ethyl, n-propyl, isopropyl, n-butyl, t-butyl, isobutyl, sec-butyl, cyclohexyl) methyl, cyclopropylmethyl, n-pentyl, n-hexyl, n-heptyl, n-octyl, and the like.

The terms "alkenyl" and "alkynyl", refers to substituted or unsubstituted unsaturated aliphatic groups analogous in length, and possible substitution to the alkyls described above, but that contain at least one double, or triple bond respectively. Representative alkenyl groups include vinyl, propen-2-yl, crotyl, isopenten-2-yl, 1,3-butadien-2-yl), 2,4-pentadienyl, and 1,4-pentadien-3-yl. Representative alkynyl groups, include ethynyl, 1- and 3-propynyl, and 3-butynyl. In certain preferred embodiments, alkyl substituents are lower alkyl groups, e.g., having from 1 to 6 carbon atoms. Similarly, alkenyl and alkynyl, preferably refer to lower alkenyl and alkynyl groups, e.g., having from 2 to 6 carbon atoms. As used herein, "alkylene" refers to an alkyl group with two open valencies (rather than a single valency), such as —$(CH_2)_{1-10}$— and substituted variants thereof.

The term "alkoxy", refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl, which renders that alkyl an ether is, or resembles an alkoxy.

The term "alkoxyalkyl", refers to an alkyl group substituted with an alkoxy group, thereby forming an ether.

The terms "amide" and "amido", are art-recognized as an amino-substituted carbonyl, and includes a moiety that can be represented by the general formula:

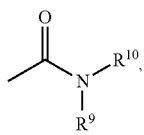

wherein $R^9$, $R^{10}$ are as defined above. Preferred embodiments of the amide will not include imides, which may be unstable.

The terms "amine" and "amino", are art-recognized and refer to both unsubstituted and substituted amines, and salts thereof, e.g., a moiety that can be represented by the general formula:

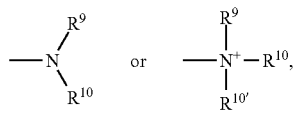

wherein $R^9$, $R^{10}$ and $R^{10'}$ each independently represent a hydrogen, an alkyl, an alkenyl, —$(CH_2)_p$—$R^8$, or $R^9$ and $R^{10}$ taken together with the N atom to which they are attached, complete a heterocycle having from 4 to 8 atoms in the ring structure; $R^8$ represents an aryl, a cycloalkyl, a cycloalkenyl, a heterocyclyl, or a polycyclyl; and p is zero, or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alk-enyl, or —$(CH_2)_p$—$R^8$. In certain embodiments, the amino group is basic, meaning the protonated form has a $pK_a > 7.00$.

The term "aralkyl", as used herein, refers to an alkyl group substituted with an aryl group, for example —$(CH_2)_p$—Ar.

The term "heteroaralkyl", as used herein, refers to an alkyl group substituted with a heteroaryl group, for example —$(CH_2)_p$-Het.

The term "aryl", as used herein, includes 5-, 6-, or 7-membered substituted, or unsubstituted single-ring aromatic groups, in which each atom of the ring is carbon. The term "aryl", also includes polycyclic ring systems, having two or more cyclic rings, in which two or more carbons are common to two adjoining rings, wherein at least one of the rings is aromatic, e.g., the other cyclic rings can be cycloalkyls, cycloalkenyls, cycloalkynyls, aryls, heteroaryls, or heterocyclyls. Aryl groups include benzene, naphthalene, phenanthrene, phenol, aniline, anthracene, or phenanthrene.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Representative carbocyclic groups include cyclopentyl, cyclohexyl, 1-cyclohexenyl, or 3-cyclohexen-1-yl, cycloheptyl.

The term "carbonyl", is art-recognized and includes such moieties, as can be represented by the general formula:

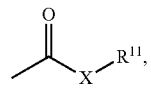

wherein X is a bond, or represents an oxygen, or a sulfur, and $R^{11}$ represents a hydrogen, an alkyl, an alkenyl, —$(CH_2)_p$—$R^8$, or a pharmaceutically acceptable salt. Where X is oxygen and $R^{11}$ is not hydrogen, the formula represents an "ester". Where X is oxygen, and $R^{11}$ is hydrogen, the formula represents a "carboxylic acid".

The terms "heteroaryl", includes substituted or unsubstituted aromatic 5- to 7-membered ring structures, more preferably 5- to 6-membered rings, whose ring structures include one to four heteroatoms. The term "heteroaryl", also includes polycyclic ring systems having two or more cyclic rings, in which two or more carbons are common to two adjoining rings, wherein at least one of the rings is heteroaromatic, e.g., the other cyclic rings can be cycloalkyls, cycloalkenyls, cycloalkynyls, aryls, heteroaryls, or heterocyclyls. Heteroaryl groups include, for example, pyrrole, furan, thiophene, imidazole, isoxazole, oxazole, thiazole, triazole, pyrazole, pyridine, pyrazine, pyridazine, or pyrimidine, and the like.

The term "heteroatom", as used herein, means an atom of any element, other than carbon or hydrogen. Preferred heteroatoms are nitrogen, oxygen, or sulfur.

The terms "heterocyclyl" or "heterocyclic group", refers to substituted or unsubstituted non-aromatic 3- to 10-membered ring structures, more preferably 3- to 7-membered rings, whose ring structures include one to four heteroatoms. The terms "heterocyclyl" or "heterocyclic group", also include polycyclic ring systems having two or more cyclic rings, in which two or more carbons are common to two adjoining rings, wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, tetrahydropyran, piperidine, piperazine, pyrrolidine, morpholine, lactones, or lactams.

The term "hydrocarbon", as used herein, refers to a group that is bonded through a carbon atom that does not have a =O or =S substituent, and typically has at least one carbon-hydrogen bond, and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon), and ethoxy (which is linked through oxygen, not carbon) are not. Hydrocarbyl groups include, but are not limited to aryl, heteroaryl, carbocycle, heterocycle, alkyl, alkenyl, alkynyl, or combinations thereof.

The terms "polycyclyl" or "polycyclic", refer to two or more rings (e.g., cycloalkyls, cycloalkenyls, cycloalkynyls, aryls, heteroaryls, or heterocyclyls) in which two or more carbons are common to two adjoining rings, e.g., the rings are "fused rings". Each of the rings of the polycycle can be substituted or unsubstituted.

As used herein, the term "probe", means a compound of the invention which is labeled with either a detectable label or an affinity tag, and which is capable of binding, either covalently, or non-covalently, to a protein kinase domain. When, for example, the probe is non-covalently bound, it may be displaced by a test compound. When, for example, the probe is bound covalently, it may be used to form cross-linked adducts, which may be quantified and inhibited by a test compound.

The term "substituted", refers to moieties having substituents replacing a hydrogen on one or more atoms of the backbone. It will be understood that "substitution", or "substituted with" includes the implicit proviso that such substitution is in accordance with permitted valence of the substituted atom, and the substituent, and that the substitution results in a stable compound, e.g., which does not spontaneously undergo transformation, such as by rearrangement, cyclization, elimination, etc. As used herein, the term "substituted", is contemplated to include all permissible substituents of organic compounds. In a broad aspect, the permissible substituents include acyclic or cyclic, branched or unbranched, carbocyclic or heterocyclic, aromatic or non-aromatic substituents of organic compounds. The permissible substituents can be one or more and the same, or different for appropriate organic compounds. For purposes of this invention, the heteroatoms such as nitrogen may have hydrogen substituents, or any permissible substituents of organic compounds described herein, which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic, or heteroaromatic moiety. It will be understood by those skilled in the art that the moieties substituted on the hydrocarbon chain can themselves be substituted, if appropriate.

Compounds of the invention also include all isotopes of atoms present in the intermediates or final compounds. Isotopes include those atoms having the same atomic number, but different mass numbers. For example, isotopes of hydrogen include deuterium and tritium.

Therapeutic Uses and Applications

The compounds of the present invention are inhibitors of protein kinase activity.

An aspect of the present invention provides a method of inhibiting protein kinase activity in a cell, the method comprising administering to said cell compound of Formula I, or Formula II, as defined herein, combinations thereof, or a pharmaceutically acceptable salt or solvate thereof.

In a further aspect, the present invention provides a method of inhibiting protein kinase in vitro or in vivo, said method comprising contacting a cell with an effective amount of a compound, or a pharmaceutically acceptable salt, or solvate thereof, as defined herein.

A further aspect of the present invention provides a method of inhibiting protein kinase activity in a human or an animal subject, the method comprising administering to said subject an effective amount of a compound of Formula I, or Formula H, as defined herein, combinations thereof, or a pharmaceutically acceptable salt, or solvate thereof.

In one embodiment, the protein kinase is selected from the following group: Tec, Src, Abl, Jak, Csk, Fak, Syk, Fer, Ack kinases, or receptor protein kinases. Preferably the protein kinases are from Tec or Src kinase family. In a particular embodiment the protein kinase is Bruton's tyrosine kinase (Btk).

The compounds of the present invention are suitable for the treatment of diseases or conditions, in which one or more of the protein kinase targets are implicated.

In one embodiment, the compounds are suitable for inhibition of a proliferative disorder, mediated by protein kinase targets.

In other embodiment, the compounds are suitable for inhibition of a proliferative disorder mediated by Tec kinase targets.

In other embodiment, the compounds are suitable for inhibition of a proliferative disorder mediated by Src kinase targets.

The term "proliferative disorder", is used herein in a broad sense to include disorder that requires control of deleterious cell proliferation, for example cancers and other disorders associated with uncontrolled cellular proliferation, such as dermatological disorders or psoriasis, certain viral disorders, certain cardiovascular diseases such as restenosis or cardiomyopathy, certain CNS disorders, auto-immune disorders such as glomerulonephritis, or rheumatoid arthritis, hormone-related diseases, metabolic disorders, stroke, alopecia, emphysema, inflammatory diseases, or infectious diseases such fungal diseases, or parasitic disorders such as malaria. In these disorders, the compounds of the present invention may induce apoptosis, or maintain stasis within the desired cells as required.

The term "protein kinase mediated disease", is used herein, associated with abnormal cellular responses triggered by protein kinase-mediated events. Furthermore, aberrant activation, or excessive expression of various protein kinases are implicated in the mechanism of multiple diseases or disorders, characterized by benign and malignant proliferation. These diseases include, but are not limited to allergies or asthma, Alzheimer's disease, autoimmune diseases, bone diseases, cancer, cardiovascular diseases, inflammatory diseases, hormone-related diseases, metabolic diseases, neurological and neurodegenerative diseases.

Thus, inhibitors of kinase families are expected to be suitable in the treatment of cancer, vascular disease, autoimmune diseases, or inflammatory conditions including, but not limited to: solid tumors, hematological malignancies, thrombus, arthritis, graft versus host disease, lupus erythematosus, psoriasis, colitis, illeitis, multiple sclerosis, uveitis, coronary artery vasculopathy, systemic sclerosis, atherosclerosis, asthma, transplant rejection, allergy and dermatomyositis.

In one embodiment, the compound of Formula I, Formula II, combinations thereof, or pharmaceutically acceptable salts, solvates, solvates of salts, stereoisomers, tautomers, isotopes, prodrugs, complexes or biologically active metabolites thereof, is acting by inhibiting one or more of the host cell kinases involved in cell proliferation, cell survival, viral replication, cardiovascular disorders, neurodegeneration, autoimmunity, a metabolic disorder, stroke, alopecia, an inflammatory disease, or an infectious disease.

In one embodiment, the proliferative disorder is cancer. The cancer may be selected from the group consisting of: chronic lymphocytic leukaemia (CLL), lymphoma, leukaemia, breast cancer, lung cancer, prostate cancer, colon cancer, melanoma, pancreatic cancer, ovarian cancer, squamous carcinoma, carcinoma of head or neck, endometrial cancer, or oesophageal carcinoma.

In another embodiment of the present invention, the infectious disease includes diseases that are caused by protozoal infestations in humans or animals. Such veterinary and human pathogenic protozoas are preferably intracellular active parasites of the phylum Apicomplexa, or Sarcomastigophora, especially *Trypanosoma, Plasmodia, Leishmania, Babesia*, or *Theileria, Cryptosporidia, Sacrocystida, Amoebia, Coccidia*, or *Trichomonadia*. The compounds of the present invention are particularly suitable for the treatment of Malaria tropica caused by *Plasmodium falciparum*, Malaria tertiana caused by *Plasmodium vivax*, or *Plasmodium ovale*, or for the treatment of Malaria quartana caused by *Plasmodium malariae*. These compounds are also suitable for the treatment of Toxoplasmosis caused by *Toxoplasma gondli*, Coccidiosis caused for instance by Isospora belli, intestinal Sarcosporidiosis caused by *Sarcocystis suihominis*, dysentery caused by *Entamoeba histolytica*, Cryptosporidiosis caused by *Cryptosporidium parvum*, Chagas disease caused by *Trypanosoma cruzi*, sleeping sickness caused by *Trypanosoma brucei*, rhodesiense or gambiense, the cutaneous or visceral, as well as other forms of *Leishmaniosis*. The present invention is also suitable for the treatment of animals infected by veterinary pathogenic *Protozoa*, like *Theileria parva*, the pathogen causing bovine East coast fever, *Trypanosoma congolense* or *Trypanosoma vivax, Trypanosoma brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing European bovine Babesiosis, as well as Babesiosis in dogs, cats or sheep, *Sarcocystis ovicanis* or *Sarcocystis ovifelis* pathogens causing Sarcocystiosis in sheep, cattle or pigs, *Cryptosporidia*, pathogens causing Cryptosporidioses in cattle and birds, *Eimeria* or *Isospora* species, pathogens causing Coccidiosis in rabbits, cattle, sheep, goats, pigs and birds, especially in chickens and turkeys. The compounds of the present invention is particularly preferred for use in the treatment of Coccidiosis or Malaria infections, or for the preparation of a drug, or feed stuff for the treatment of these diseases. These treatments can be prophylactic or curative. In the treatment of malaria, the protein kinase inhibitor, as defined above may be combined with other anti-malaria agents. The present compound described may further be used for viral infections, or other infections caused by *Pneumocystis carinii*. These compounds may be used alone, or in combination with one, or more agents for the efficient therapy.

Tec kinases is a family of non-receptor tyrosine kinases predominantly, but not exclusively, expressed in cells of hematopoietic origin. The Tec family comprises: Tec, Bruton's tyrosine kinase (Btk), inducible T-cell kinase (Itk), resting lymphocyte kinase (Rlk/Txk), or bone marrow-expressed kinase (Bmx/Etk).

Btk is activated by Src-family kinases and phosphorylates PLC gamma leading to effects on B-cell function and survival. Additionally, Btk is important in signal transduction in response to immune complex recognition by macrophage, mast cells or neutrophils. Btk inhibition is also important in survival of lymphoma cells (Herman SEM. Blood, 2011, 117:6287-6289) suggesting that inhibition of Btk may be useful in the treatment of lymphomas. Bmx, another Tec family member are expected to be suitable in the treatment of various diseases including cancer, cardiovascular disease and inflammation. These compounds may be used alone, or in combination with one or more agents for the therapy.

In further aspect of the present invention, the compound of Formula I, Formula H, combinations thereof, or pharmaceutically acceptable salts, solvates, solvates of salts, stereoisomers, tautomers, isotopes, prodrugs, complexes or biologically active metabolites thereof, is acting as inhibitor of cell kinases, as anti-inflammatory, anti-cancer, or as antithrombotic agents. These compounds may be used alone, or in combination with one or more agents, for the treatment of cancer, inflammatory or infectious diseases, or thrombi.

More specifically, the compounds of the present invention can also be used in combination with one or more chemotherapeutic agents used particularly in effective treatment of cancer, or other neoplasms.

The compounds of Formula I, Formula II, combinations thereof, or pharmaceutically acceptable salts, solvates, solvates of salts, stereoisomers, tautomers, isotopes, prodrugs, complexes or biologically active metabolites thereof, can be used in combination with, but not limiting to:

1. Anti-proliferative agents, selected from the group of: adriamycin, dexamethasone, vincristine, cyclophosphamide, fluorouracil, topotecan, taxol, interferons, platinum derivatives; anti-inflammatory agents comprising corticosteroids, TNF blockers, IL-1 RA, azathioprine, cyclophosphamide, or sulfasalazine;
2. Prenyl-protein transferase inhibitors;
3. Angiogensis inhibitors, comprising: sorafenib, sunitinib, pazopanib, or everolimus;
4. Immunomodulatory or immunosuppressive agents selected from the group comprising: cyclosporin, tacrolimus, rapamycin, mycophenolate mofetil, interferons, corticosteroids, cyclophophamide, azathioprine, or sulfasalazine;
5. PPAR-γ agonists such as thiazolidinediones;
6. PPAR-δ agonists;
7. Inhibitors of inherent multidrug resistance;
8. Agents for the treatment of anemia, comprising erythropoiesis, stimulating agents, vitamins, or iron supplements;
9. Anti-emetic agents including: 5-HT3 receptor antagonists, dopamine antagonists, NK1 receptor antagonists, H1 histamine receptor antagonists, cannabinoids, benzodiazepines, anticholinergic agents, or steroids;

10. Agents for the treatment of neutropenia;
11. Immunologic-enhancing agents;
12. Proteasome inhibitors;
13. HDAC inhibitors;
14. Inhibitors of the chemotrypsin-like activity in the proteasome;
15. E3 ligase inhibitors;
16. Modulators of the immune system including: interferon-alpha, *Bacillus* Calmette-Guerin (BCG), or ionizing radiation (UVB) that can induce the release of cytokines, such as the interleukins, TNF, or induce release of death receptor ligands such as TRAIL;
17. Modulators of death receptors TRAIL or TRAIL-agonists, including humanized antibodies HGS-ETR1, or HGS-ETR in combination, or sequentially with radiation therapy;
18. Neurotrophic factors comprising: acetylcholinesterase inhibitors, MAO inhibitors, interferons, anti-convulsants, ion channel blockers, or riluzole;
19. Anti-Parkinsonian agents comprising: anticholinergic agents, dopaminergic agents, including dopaminergic precursors, monoamine oxidase B inhibitors, COMT inhibitors, or dopamine receptor agonists;
20. Agents for treating cardiovascular disease comprising: beta-blockers, ACE inhibitors, diuretics, nitrates, calcium channel blockers, or statins;
21. Agents for treating liver disease comprising: corticosteroids, cholestyramine, or interferons;
22. Anti-viral agents including: nucleoside reverse transcriptase inhibitors, nonnucleoside reverse transcriptase inhibitors, protease inhibitors, integrase inhibitors, fusion inhibitors, chemokine receptor antagonists, polymerase inhibitors, viral proteins synthesis inhibitors, viral protein modification inhibitors, neuraminidase inhibitors, fusion or entry Inhibitors;
23. Agents for treating blood disorders including: corticosteroids, anti-leukemic agents, or growth factors;
24. Agents for treating immunodeficiency disorders comprising: gamma globulin, adalimumab, etarnecept, or infliximab; or
25. HMG-CoA reductase inhibitors comprising: torvastatin, fluvastatin, lovastatin, pravastatin, rosuvastatin, simvastatin, or pitavastatin.

As defined herein, an effect against a proliferative disorder mediated by a kinase within the scope of the present invention may be demonstrated by the ability to inhibit a purified kinase in vitro or to inhibit cell proliferation or survival in an in vitro cell assay, for example in Btk Kinase Inhibition Assay and Splenic Cell Proliferation Assay. These assays are described in more details in the accompany examples.

The present invention includes the transdermal, rectal, parenteral, or oral administration of compounds of Formula I, or Formula II (or combinations thereof) to a human or animal subject. The dosage unit for the administration may contain any suitable amount of a compound of Formula I, Formula II, combinations thereof (or a pharmaceutical acceptable salt or solvate thereof, or combinations thereof), for example from about 10 mg to about 5000 mg. Preferably, the dosage unit for oral administration may contain from 50 mg to 500 mg, per human individual.

The compounds of the present invention may be administered 1 to 4 times a day. A dosage may be any suitable therapeutically effective amount, for example, between 0.01-100 mg/kg body weight/day of the compounds of the present invention may be administered to a patient receiving these compositions. The dose can vary within wide limits and is to be suited to the individual conditions in each individual case. For the above uses the appropriate dosage will vary depending on the mode of administration, the particular condition to be treated and the effect desired. Preferably a dose of 1 to 50 mg/kg body weight/day may be used.

In an embodiment of the present invention suitable dosage rates for larger mammals, for example humans, are of the order of from about 10 mg to 3 g/day, administered orally once, or divided doses, such as 2 to 4 times a day, or in sustained release form. For topical delivery, depending on the permeability of the skin, the type and the severity of the disease and dependent on the type of formulation and frequency of application, different concentrations of active compounds within the medicament can be sufficient to elicit a therapeutic effect by topical application. Preferably, the concentration of an active compound pharmaceutically acceptable salts, solvates, solvates of salts, stereoisomers, tautomers, isotopes, prodrugs, complexes or biologically active metabolites thereof, within a medicament according to the present invention is in the range of between 1 μmol/L and 100 mmol/L.

Specific Abbreviations
MS mass spectrometry
ml milliliter
μl microliter
mmol millimole
THF tetrahydrofuran
$H_2$ hydrogen
Pd/C palladium on carbon
HCl hydrogen chloride
NaH sodium hydride (60% in mineral oil)
tBuOK potassium tert-butoxide
CuI copper (I) iodide
$Cs_2CO_3$ cesium carbonate
$K_2CO_3$ potassium carbonate
DIPEA N,N-diisopropylethylamine
TEA triethylamine
$MgSO_4$ magnesium sulfate
$NaHCO_3$ sodium bicarbonate
$H_2O_2$ hydrogen peroxide
$NH_4OH$ ammonium hydroxide
iPrOH isopropyl alcohol
NBS N-bromosuccinimide
NIS N-iodosuccinimide
$POCl_3$ phosphoryl chloride
PPTS pyridinium p-toluenesulfonate
$NaBH_4$ sodium borohydride
$NaBH(OAc)_3$ sodium triacethoxyborohydride
NaOH sodium hydroxide
$Ac_2O$ acetic anhydride
TFA trifluoroacetic acid
$NaIO_4$ sodium periodate
NMO N-methylmorpholine N-oxide
DIBAL-H diisobuthylaluminium hydride
DME ethylene glycol dimethyl ether
DIAD diisopropyl azodicarboxylate
$CaCl_2$ calcium chloride
$(Cy)_3P$ triclyclohexylphosphine
$Ph_3P$ triphenyl phosphine
$PdCl_2(dppf)$ [1,1'-Bis(diphenylphosphino)ferrocene]dichloropalladium(II)
$Pd_2(dba)_3$ Tris(dibenzylideneacetone)dipalladium(0)
HATU (1-[Bis(dimethylamino)methylene]-1H-1,23-triazolo

[4,5-b]pyridinium 3-oxid hexafluorophosphate)

General Synthetic Methods

In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art, In further embodiment of the present invention is provided general synthetic method(s) useful in the preparation of compounds described in the present invention.

General Synthetic Method A:

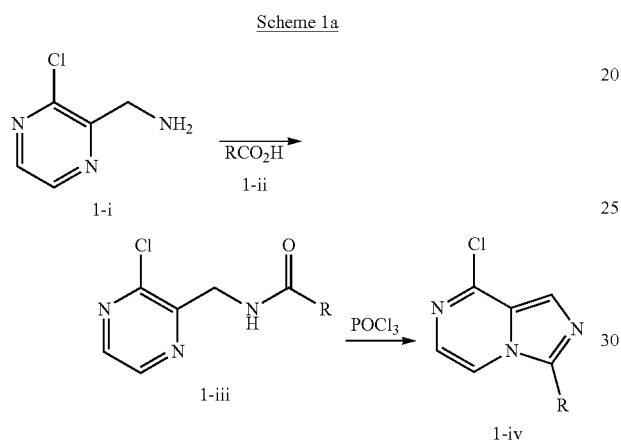

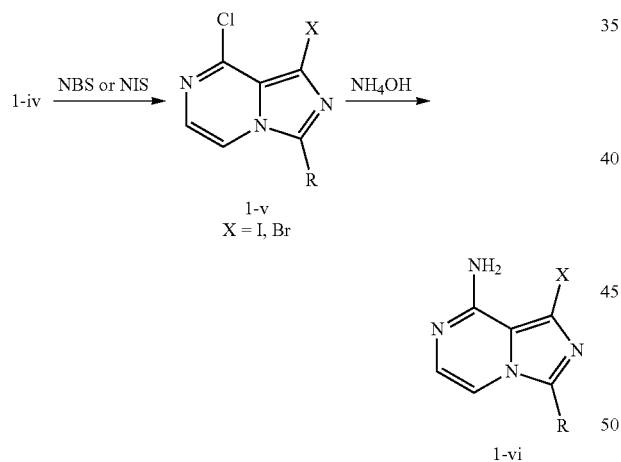

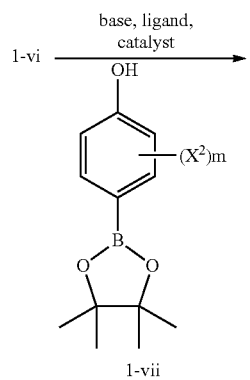

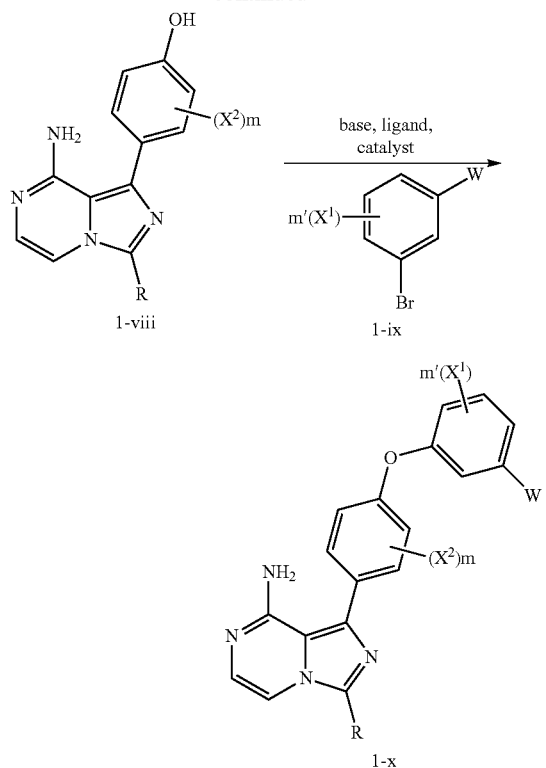

General Synthetic Method B:

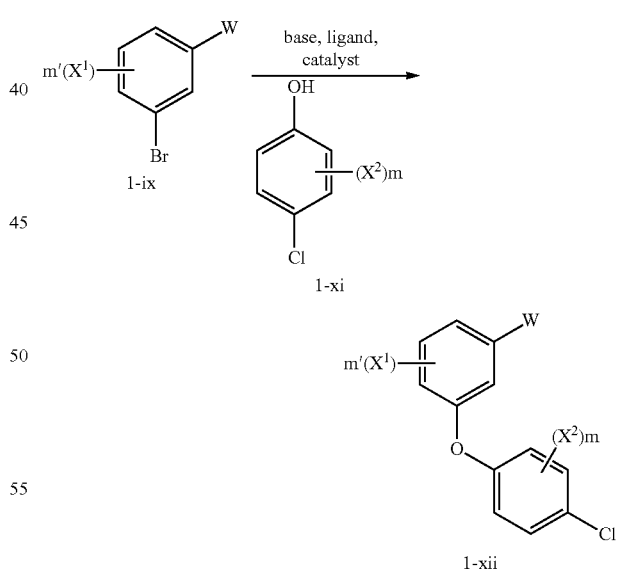

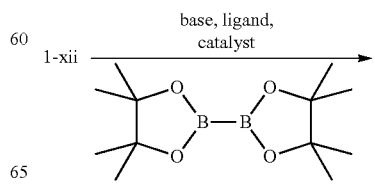

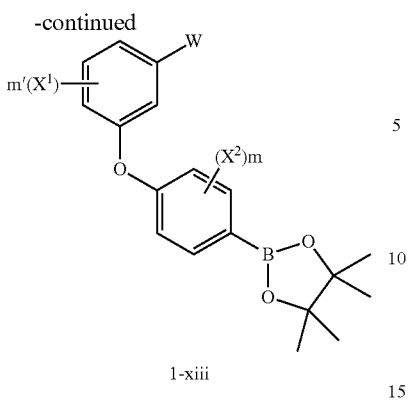

1-xiii

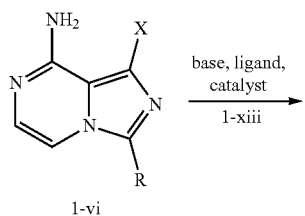

1-vi

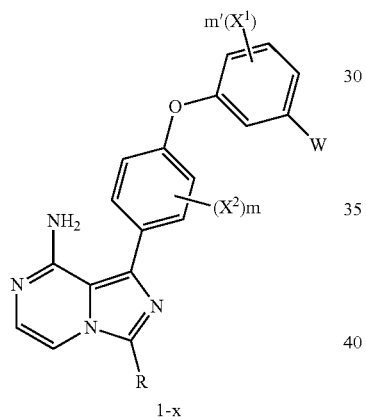

1-x

EXAMPLES

The following synthetic methods are intended to be representative of the chemistry used to prepare compounds of the present invention and are not intended to be limiting.

Synthesis of Intermediate 2-c

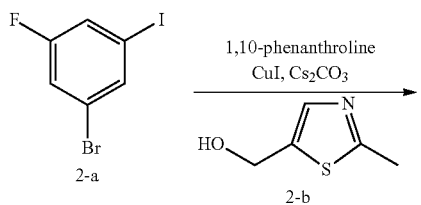

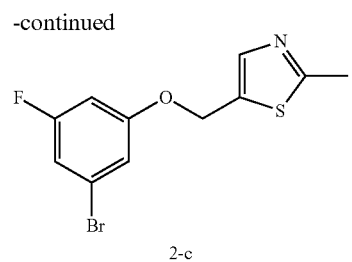

2-c

To a solution of 1-bromo-3-fluoro-5-iodobenzene 2-a (7.52 g, 25.0 mmol) in 1,4-dioxane (12.50 ml) was added (2-methylthiazol-5-yl)methanol 2-b (3.55 g, 27.5 mmol), 1,10-phenanthroline (901 mg, 5.0 mmol), copper (I) iodide (476 mg, 2.50 mmol), and cesium carbonate (11.40 g, 35.0 mmol). The reaction was stirred at 110° C. for 2 days, and then cooled to room temperature, diluted with ethyl acetate, and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered, and concentrated under reduced pressure. Purification by silica gel chromatography provided Intermediate 2-c as a beige solid.

Synthesis of Intermediate 3-b

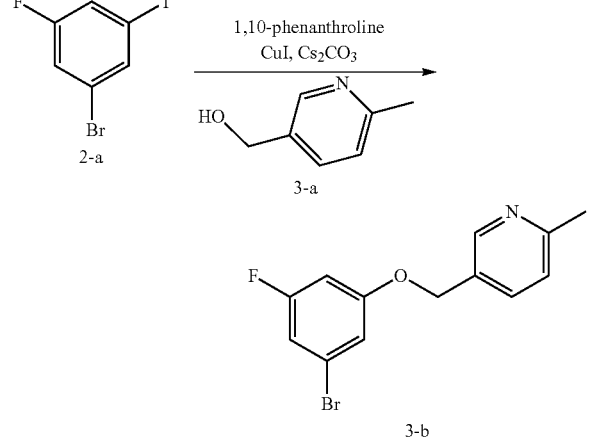

To a solution of 1-bromo-3-fluoro-5-iodobenzene 2-a (5.0 g, 16.62 mmol) in toluene (8.3 ml) was added (6-methyl-pyridin-3-yl) methanol 3-a (2.25 g, 18.28 mmol), 1,10-phenanthroline (599 mg, 3.32 mmol), copper (I) iodide (316 mg, 1.66 mmol), and cesium carbonate (7.58 g, 23.26 mmol). The reaction was stirred at 110° C. for 2 days, and then cooled to room temperature, diluted with ethyl acetate, and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered, and concentrated under reduced pressure. Purification by silica gel chromatography provided Intermediate 3-b as a beige solid.

Synthesis of Intermediate 4-b

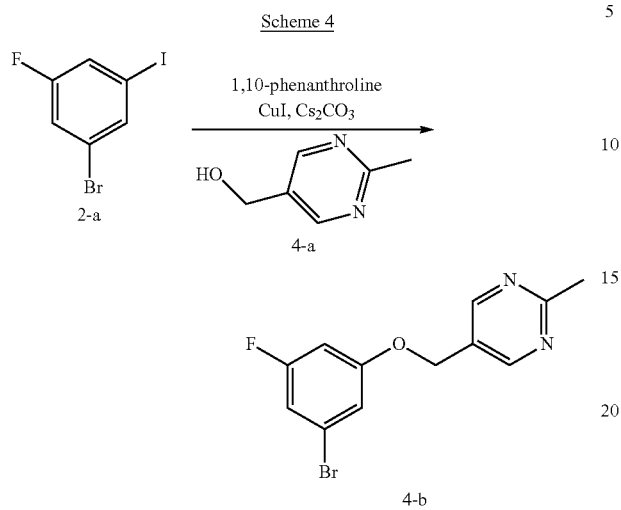

Synthesis of Intermediate 5-f

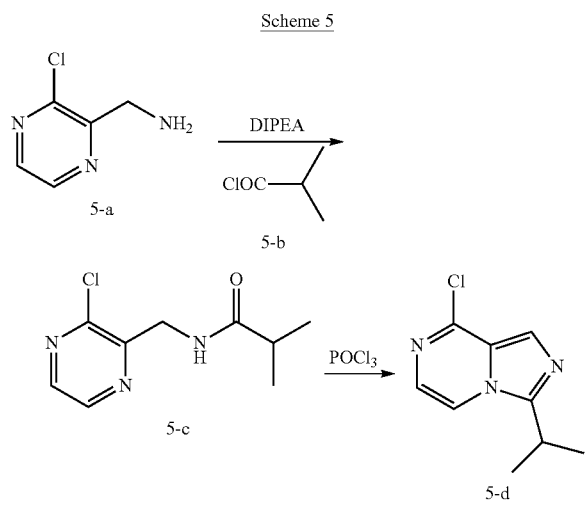

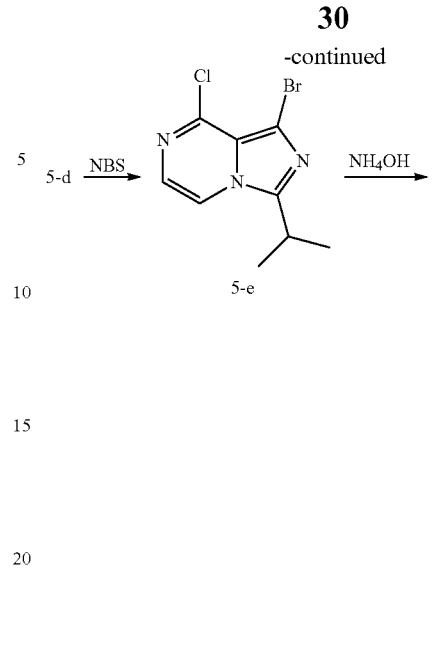

To a solution of 1-bromo-3-fluoro-5-iodobenzene 2-a (5.0 g, 16.62 mmol) in toluene (8.3 ml) was added (2-methylpyrimidin-5-yl)methanol 4-a (2.26 g, 18.28 mmol), 1,10-phenanthroline (599 mg, 3.32 mmol), copper (I) iodide (316 mg, 1.66 mmol), and cesium carbonate (7.58 g, 23.26 mmol). The reaction was stirred at 110° C. for 2 days, and then cooled to room temperature, diluted with ethyl acetate, and filtered over celite. A saturated aqueous solution of ammonium chloride was added to the filtrate, the organic layer was separated, and the aqueous phase was extracted twice with ethyl acetate. The combined organic extracts were washed with brine, dried over $MgSO_4$, filtered, and concentrated under reduced pressure. Purification by silica gel chromatography provided Intermediate 4-b as a beige solid.

Step 1: Intermediate 5-c

To a solution of (3-chloropyrazin-2-yl)methanamine bis hydrochloride 5-a (2.0 g, 13.9 mmol) in dichloromethane cooled to 0° C. were sequentially added DIPEA (4.87 ml, 27.9 mmol), and isobutyryl chloride 5-b (1.8 g, 16.7 mmol), and the reaction mixture was stirred for 1 hour at room temperature. Water and ethyl acetate were added, the organic layer was separated, washed with brine, dried over anhydrous $MgSO_4$, filtered, and concentrated under reduced pressure to provide Intermediate 5-c as a beige solid.

Step 2: Intermediate 5-d

To a solution of Intermediate 5-c (2.5 g, 11.7 mmol) in ethyl acetate (36.6 ml) cooled to 0° C. was added DMF (2.4 ml) and phosphorous oxychloride (1.9 ml, 21.0 mmol) dropwise. After the addition was completed, the reaction mixture was stirred for 45 minutes at room temperature. An ice cooled saturated aqueous solution of $Na_2CO_3$ and dichloromethane were slowly added, the organic layer was separated, the aqueous phase was extracted twice with dichloromethane, the combined organic extracts were washed with brine, dried over anhydrous $MgSO_4$, filtered, and concentrated under reduced pressure to provide Intermediate 5-d as a beige oil.

Step 3: Intermediate 5-e

To a solution of Intermediate 5-d (1.9 g, 9.7 mmol) in DMF cooled to 0° C. was slowly added a 0.7N solution of N-bromosuccinimide in DMF (15.2 ml, 10.7 mmol) under an atmosphere of nitrogen. After the addition was completed the reaction mixture was stirred for 15 minutes. Water was added; a precipitate formed, and was collected by filtration to provide Intermediate 5-e as a beige solid.

Step 4: Intermediate 5-f

To a solution of Intermediate 5-e (2.6 g, 9.5 mmol) in iPrOH (13.1 ml) was added $NH_4OH$ (18.5 ml), and the reaction mixture was stirred at 90° C. overnight. Volatiles were removed under reduced pressure. Water was added to the residue; a precipitate formed and was collected by filtration to provide Intermediate 5-f as a beige solid.

Synthesis of Intermediate 6-e

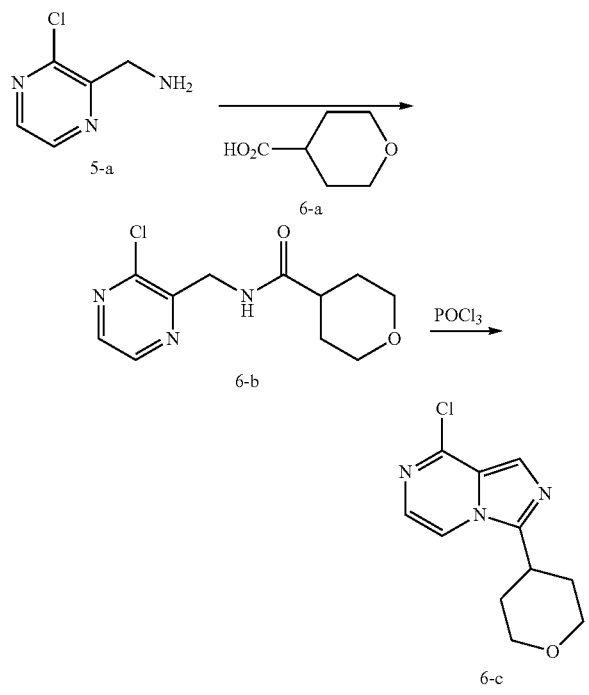

Scheme 6

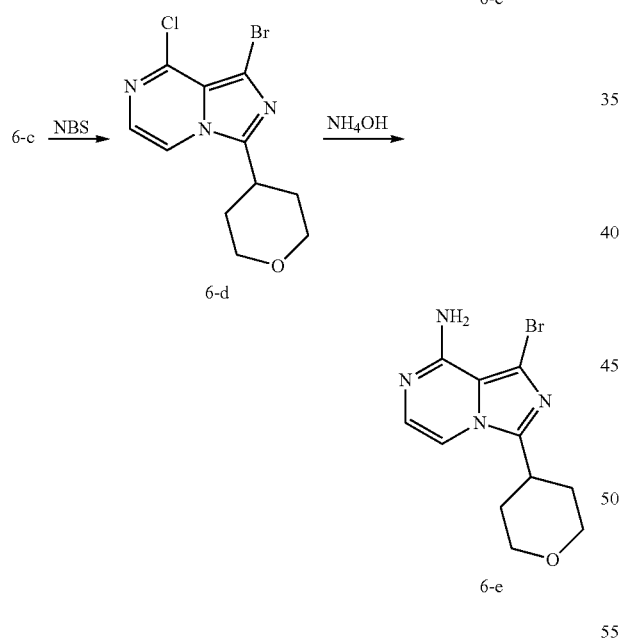

Step 1: Intermediate 6-b

To a solution of tetrahydro-2H-pyran-4-carboxylic acid 6-a (2.17 g, 16.7 mmol) in dichloromethane (2.5 ml) cooled to 0° C. were sequentially added a few drops of DMF followed by oxalyl chloride (890 μl, 10.1 mmol), and the mixture was stirred for 30 minutes at room temperature. Volatiles were removed under reduced pressure and the residue was dissolved in DMF. (3-chloropyrazin-2-yl)methanamine bis hydrochloride 5-a (2.0 g, 9.2 mmol) and DIPEA (6.45 ml, 37.0 mmol) were sequentially added, and the reaction mixture was stirred for 1 hour at room temperature. Water and dichloromethane were added, the organic layer was separated, washed with brine, dried over anhydrous MgSO₄, filtered, and concentrated under reduced pressure to provide Intermediate 6-b as a white solid.

Step 2: Intermediate 6-c

To a solution of Intermediate 6-b (2.0 g, 7.8 mmol) in ethyl acetate (24.5 ml) cooled to 0° C. was added DMF (1.6 ml) and phosphorous oxychloride (1.3 ml, 14.0 mmol) dropwise. After the addition was completed, the reaction mixture was stirred for 45 minutes at room temperature. An ice cooled saturated aqueous solution of Na₂CO₃ and dichloromethane were slowly added, the organic layer was separated, the aqueous phase was extracted twice with dichloromethane, the combined organic extracts were washed with brine, dried over anhydrous MgSO₄, filtered, and concentrated under reduced pressure to provide Intermediate 6-c as a beige oil.

Step 3: Intermediate 6-d

To a solution of Intermediate 6-c (1.9 g, 8.0 mmol) in DMF cooled to 0° C. was slowly added a 0.7N solution of N-bromosuccinimide in DMF (12.5 ml, 8.8 mmol) under an atmosphere of nitrogen. After the addition was completed the reaction mixture was stirred for 15 minutes. Water was added; a precipitate formed, and was collected by filtration to provide Intermediate 6-d as a beige solid.

Step 4: Intermediate 6-e

To a solution of Intermediate 6-d (1.8 g, 5.8 mmol) in iPrOH (8.1 ml) was added NH₄OH (11.4 ml), and the reaction mixture was stirred at 90° C. overnight. Volatiles were removed under reduced pressure. Water was added to the residue; a precipitate formed, and was collected by filtration to provide Intermediate 6-e as a beige solid.

Synthesis of Intermediate 7-e

Scheme 7

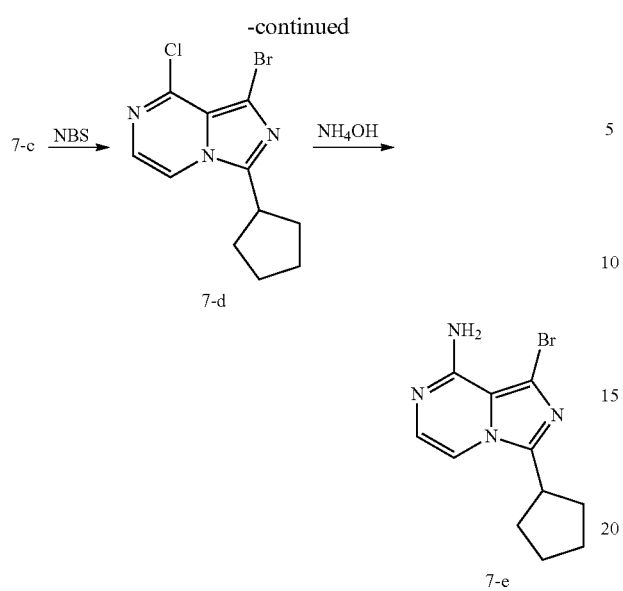

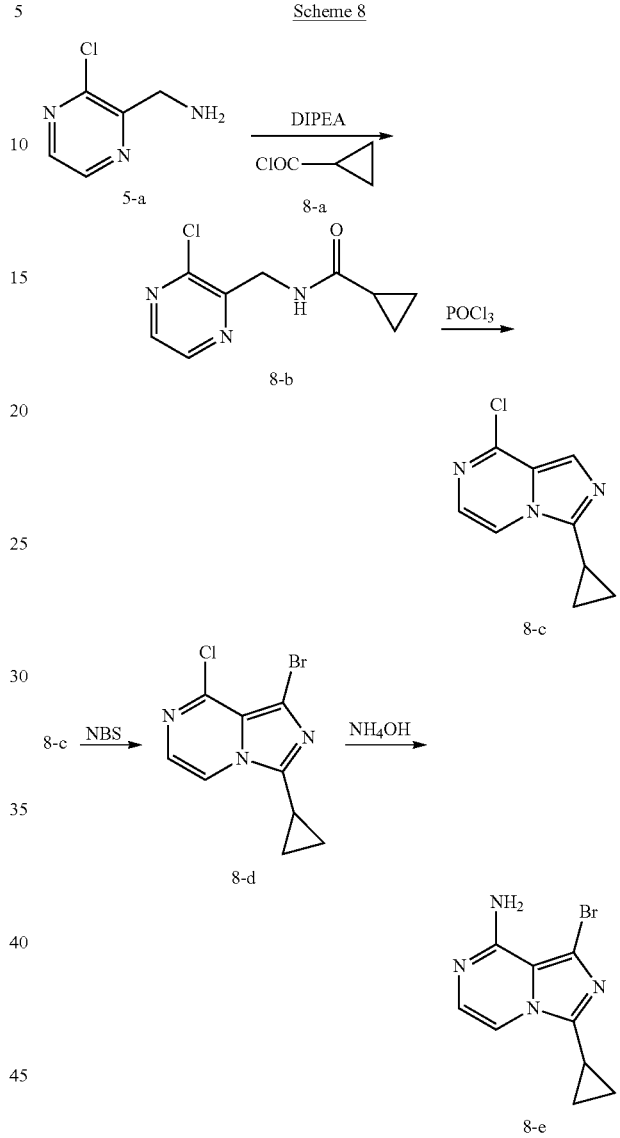

Synthesis of Intermediate 8-e

Step 1: Intermediate 7-b

To a solution of (3-chloropyrazin-2-yl)methanamine bis hydrochloride 5-a (2.0 g, 9.2 mmol) in dichloromethane (92 ml) cooled to 0° C. were sequentially added cyclopentanecarbonyl chloride 7-a (2.2 g, 16.7 mmol), and DIPEA (6.45 ml, 37.0 mmol), and the reaction mixture was stirred for 1 hour at room temperature. Water and dichloromethane were added, the organic layer was separated, washed with brine, dried over anhydrous MgSO$_4$, filtered, and concentrated under reduced pressure to provide Intermediate 7-b as a white solid.

Step 2: Intermediate 7-c

To a solution of Intermediate 7-b (2.3 g, 9.6 mmol) in ethyl acetate (30.0 ml) cooled to 0° C. was added DMF (2.0 ml), and phosphorous oxychloride (1.6 ml, 17.3 mmol) dropwise. After the addition was completed, the reaction mixture was stirred for 45 minutes at room temperature. An ice cooled saturated aqueous solution of Na$_2$CO$_3$ and dichloromethane were slowly added, the organic layer was separated, the aqueous phase was extracted twice with dichloromethane, the combined organic extracts were washed with brine, dried over anhydrous MgSO$_4$, filtered, and concentrated under reduced pressure to provide Intermediate 7-c as a beige oil.

Step 3: Intermediate 7-d

To a solution of Intermediate 7-c (2.1 g, 9.5 mmol) in DMF cooled to 0° C. was slowly added a 0.7N solution of N-bromosuccinimide in DMF (14.9 ml, 10.4 mmol) under an atmosphere of nitrogen. After the addition was completed the reaction mixture was stirred for 15 minutes. Water was added; a precipitate formed, and was collected by filtration to provide Intermediate 7-d as a beige solid.

Step 4: Intermediate 7-e

To a solution of Intermediate 7-d (2.8 g, 9.3 mmol) in iPrOH (12.9 ml) was added NH$_4$OH (18.2 ml) and the reaction mixture was stirred at 90° C. overnight. Volatiles were removed under reduced pressure. Water was added to the residue; a precipitate formed, and was collected by filtration to provide Intermediate 7-e as a beige solid.

Step 1: Intermediate 8-b

To a solution of (3-chloropyrazin-2-yl)methanamine bis hydrochloride 5-a (3.4 g, 15.9 mmol) in dichloromethane (159 ml) cooled to 0° C. were sequentially added cyclopropanecarbonyl chloride 8-a (2.0 g, 19.3 mmol), and DIPEA (11.1 ml, 63.8 mmol), and the reaction mixture was stirred for 1 hour at room temperature. Water and ethyl acetate were added, the organic layer was separated, washed with brine, dried over anhydrous MgSO$_4$, filtered, and concentrated under reduced pressure to provide Intermediate 8-b as a white solid Step 2: Intermediate 8-c To a solution of Intermediate 8-b (3.4 g, 15.9 mmol) in ethyl acetate (50.0 ml) cooled to 0° C. was added DMF (3.3 ml), and phosphorous oxychloride (2.6 ml, 28.7 mmol) dropwise. After the addition was completed, the reaction mixture was stirred for 45 minutes at room temperature. An ice cooled saturated aqueous solution of Na$_2$CO$_3$ and dichloromethane were slowly added, the organic layer was separated, the aqueous phase was extracted twice with dichloromethane, the combined organic extracts were washed with brine, dried over anhydrous MgSO$_4$, filtered, and concentrated under reduced pressure to provide Intermediate 8-c as an orange solid.

Step 3: Intermediate 8-d

To a solution of Intermediate 8-c (3.1 g, 15.9 mmol) in DMF cooled to 0° C. was slowly added a 0.7N solution of N-bromosuccinimide in DMF (25.0 ml, 17.5 mmol) under an atmosphere of nitrogen. After the addition was completed the reaction mixture was stirred for 15 minutes. Water was added; a precipitate formed, and was collected by filtration to provide Intermediate 8-d as a yellow solid.

Step 4: Intermediate 8-e

To a solution of Intermediate 8-d (2.7 g, 9.9 mmol) in iPrOH (13.7 ml) was added NH$_4$OH (19.3 ml) and the reaction mixture was stirred at 90° C. overnight. Volatiles were removed under reduced pressure. Water was added to the residue; a precipitate formed, and was collected by filtration to provide Intermediate 8-e as a yellow solid.

Synthesis of Intermediate 9-a

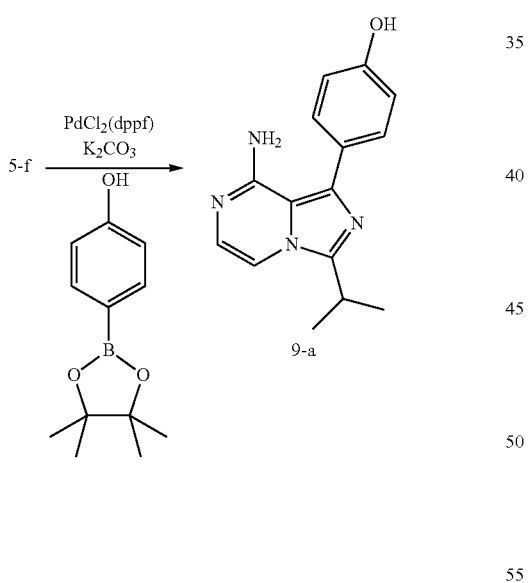

To a solution of Intermediate 5-f (1.5 g, 5.9 mmol) in 1,2-dimethoxyethane (36.2 ml) and water (9.0 ml), were sequentially added potassium carbonate (2.5 g, 18.2 mmol), 4-(4,4,5,5-tetramethyl-1,3,2-dioxaborolan-2-yl)phenol (1.5 g, 6.7 mmol), and PdCl$_2$(dppf) (200 mg, 0.3 mmol) under an atmosphere of nitrogen. The reaction mixture was stirred at 90° C. overnight, and then cooled to room temperature. Volatiles were removed under reduced pressure. Purification by silica gel chromatography provided Intermediate 9-a as a beige solid.

Synthesis of Intermediate 10-a

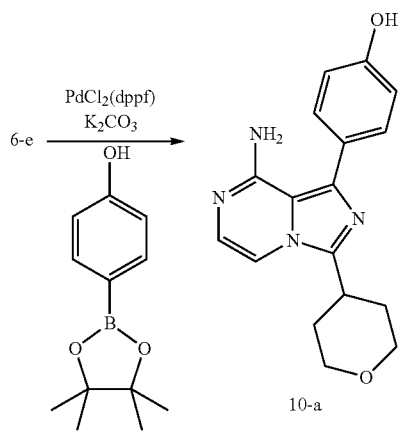

To a solution of Intermediate 6-e (1.9 g, 6.4 mmol) in 1,2-dimethoxyethane (39.3 ml) and water (9.8 ml) were sequentially added potassium carbonate (2.7 g, 19.8 mmol), 4-(4,4,5,5-tetramethyl-1,3,2-dioxaborolan-2-yl)phenol (1.6 g, 7.3 mmol), and PdCl$_2$(dppf) (354 mg, 0.5 mmol) under an atmosphere of nitrogen. The reaction mixture was stirred at 90° C. overnight, and then cooled to room temperature. Volatiles were removed under reduced pressure. Purification by silica gel chromatography provided Intermediate 10-a as a beige solid.

Synthesis of Intermediate 11-a

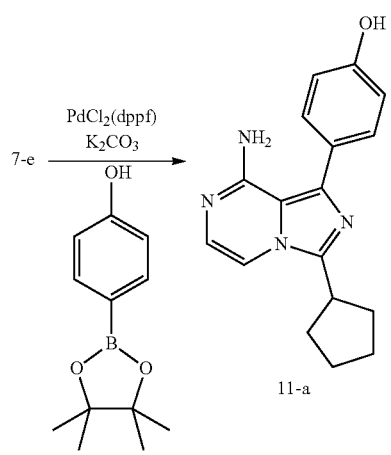

To a solution of Intermediate 7-e (2.3 g, 8.3 mmol) in 1,2-dimethoxyethane (51.4 ml) and water (12.8 ml) were sequentially added potassium carbonate (3.5 g, 25.9 mmol), 4-(4,4,5,5-tetramethyl-1,3,2-dioxaborolan-2-yl)phenol (2.1 g, 9.6 mmol), and PdCl$_2$(dppf) (308 mg, 0.4 mmol) under an atmosphere of nitrogen. The reaction mixture was stirred at 90° C. overnight, and then cooled to room temperature.

Volatiles were removed under reduced pressure. Purification by silica gel chromatography provided Intermediate 11-a as a beige solid.

Synthesis of Intermediate 12-a

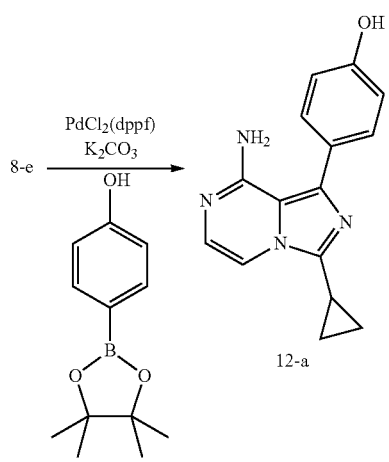

To a solution of Intermediate 8-e (500 mg, 1.9 mmol) in 1,2-dimethoxyethane (12.1 ml) and water (3.0 ml), were sequentially added potassium carbonate (846 mg, 6.1 mmol), 4-(4,4,5,5-tetramethyl-1,3,2-dioxaborolan-2-yl)phenol (500 mg, 2.3 mmol), and PdCl$_2$(dppf) (72 mg, 0.1 mmol) under an atmosphere of nitrogen. The reaction mixture was stirred at 90° C. overnight, and then cooled to room temperature. Volatiles were removed under reduced pressure. Purification by silica gel chromatography provided Intermediate 12-a as a beige solid.

Synthesis of Compound 1

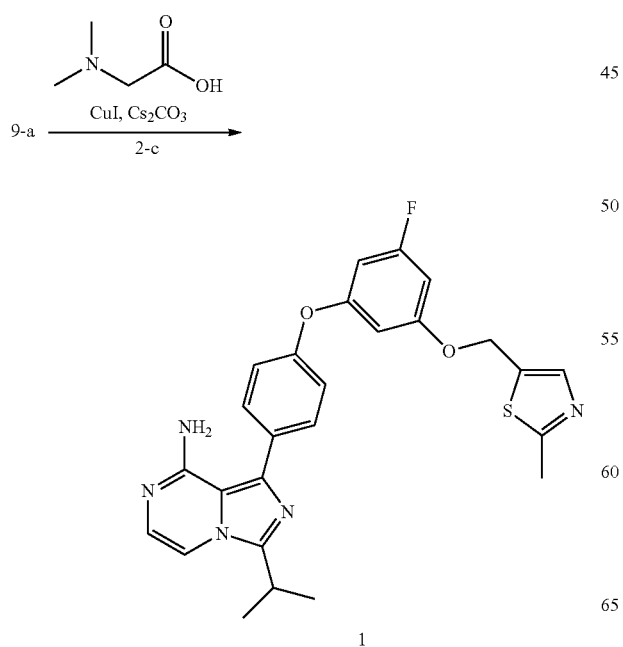

A solution of Intermediate 9-a (300 mg, 1.1 mmol), Intermediate 2-c (405 mg, 1.3 mmol), N,N-Dimethylglycine (231 mg, 2.2 mmol), cesium carbonate (1.1 g, 3.3 mmol), and copper(I) iodide (141 mg, 0.7 mmol) in 1,4-dioxane (1.5 ml) was heated in a pressure vessel at 110° C. for 36 hours, then cooled to room temperature. Ethyl acetate was added, the reaction was adsorbed on silica gel. Purification by silica gel chromatography provided Compound 1. Compound 1 was dissolved in dichloromethane, 1N HCl in diethyl ether was added, a precipitate formed and was collected by filtration to provide Compound 1·2HCl as a yellow solid. MS (m/z) M+H=490.3

Synthesis of Compound 3

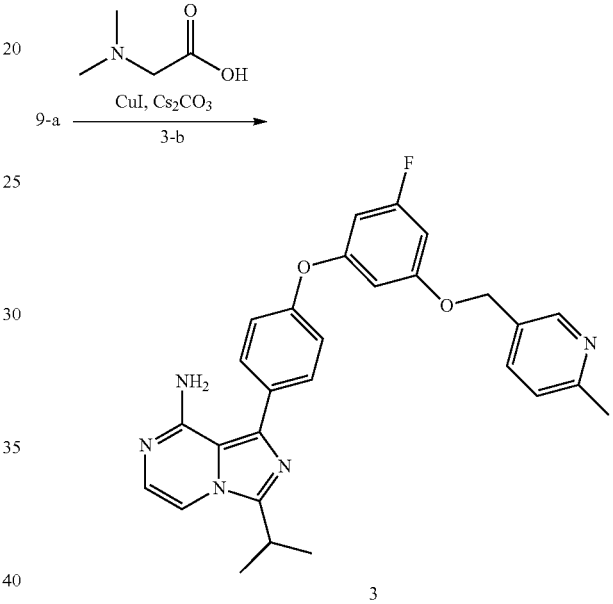

A solution of Intermediate 9-a (300 mg, 1.1 mmol), Intermediate 3-b (397 mg, 1.3 mmol), N,N-Dimethylglycine (231 mg, 2.2 mmol), cesium carbonate (1.1 g, 3.3 mmol), and copper(I) iodide (141 mg, 0.7 mmol) in 1,4-dioxane (1.5 ml) was heated in a pressure vessel at 110° C. overnight, then cooled to room temperature. Ethyl acetate was added, the reaction was adsorbed on silica gel. Purification by silica gel chromatography provided Compound 3 as a yellow solid. Compound 3 was dissolved in dichloromethane, 1N HCl in diethyl ether was added, a precipitate formed and was collected by filtration to provide Compound 3·2HCl as a yellow solid. MS (m/z) M+H=484.3

Synthesis of Compound 2

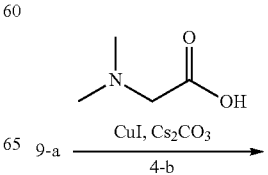

-continued

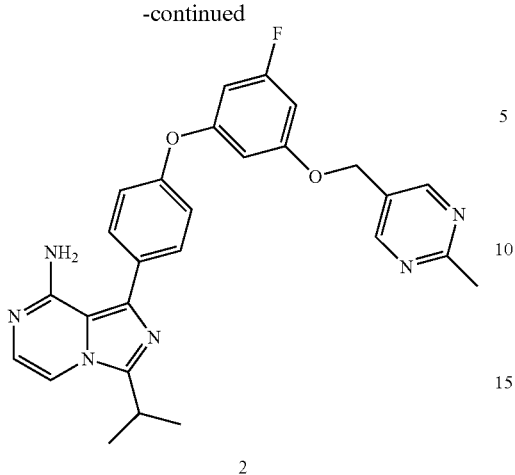

2

A solution of Intermediate 9-a (300 mg, 1.1 mmol), Intermediate 4-b (399 mg, 1.3 mmol), N,N-Dimethylglycine (231 mg, 2.2 mmol), cesium carbonate (1.1 g, 3.3 mmol), and copper(I) iodide (141 mg, 0.7 mmol) in 1,4-dioxane (1.5 ml) was heated in a pressure vessel at 110° C. overnight, then cooled to room temperature. Ethyl acetate was added, the reaction was adsorbed on silica gel. Purification by silica gel chromatography provided Compound 2. Compound 2 was dissolved in dichloromethane, 1N HCl in diethyl ether was added, a precipitate formed, and was collected by filtration to provide Compound 2·2HCl as a yellow solid. MS (m/z) M+H=485.2

Synthesis of Compound 7

Scheme 16

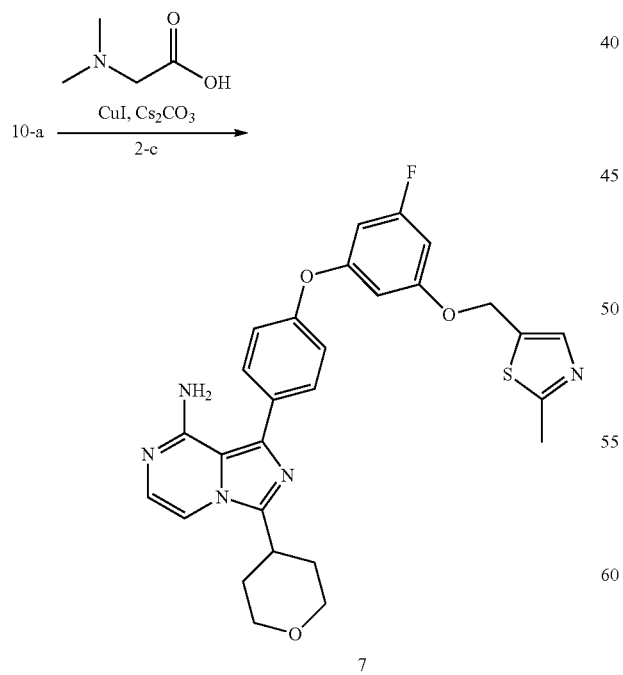

7

A solution of Intermediate 10-a (300 mg, 1.0 mmol), Intermediate 2-c (351 mg, 1.2 mmol), N,N-Dimethylglycine (199 mg, 1.9 mmol), cesium carbonate (945 mg, 2.9 mmol), and copper(I) iodide (122 mg, 0.6 mmol) in 1,4-dioxane (1.3 ml) was heated in a pressure vessel at 110° C. for 36 hours, then cooled to room temperature. Ethyl acetate was added, the reaction was adsorbed on silica gel. Purification by silica gel chromatography provided Compound 7 as a beige solid. MS (m/z) M+H=532.2

Synthesis of Compound 8

Scheme 17

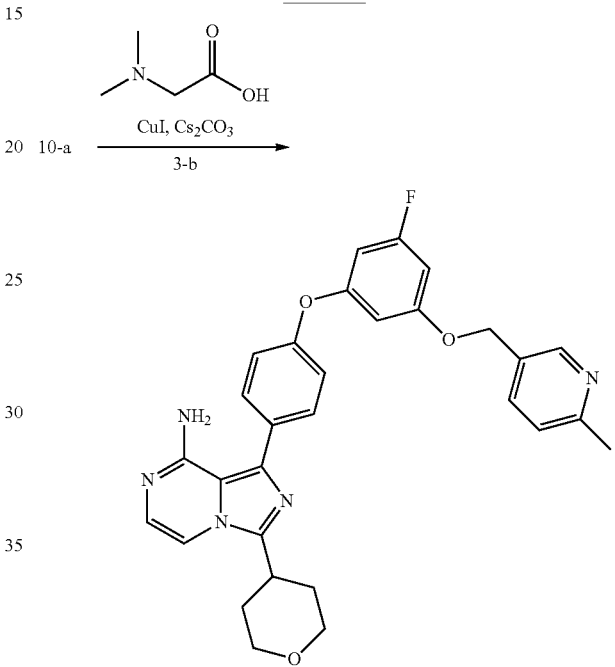

8

A solution of Intermediate 10-a (200 mg, 0.6 mmol), Intermediate 3-b (229 mg, 0.8 mmol), N,N-Dimethylglycine (133 mg, 1.3 mmol), cesium carbonate (630 mg, 1.9 mmol), and copper(I) iodide (81 mg, 0.4 mmol) in 1,4-dioxane (0.8 ml) was heated in a pressure vessel at 110° C. for 36 hours, then cooled to room temperature. Ethyl acetate was added, the reaction was adsorbed on silica gel. Purification by silica gel chromatography provided Compound 8 as a beige solid. MS (m/z) M+H=526.2

Synthesis of Compound 9

Scheme 18

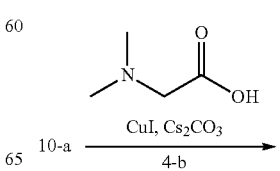

-continued

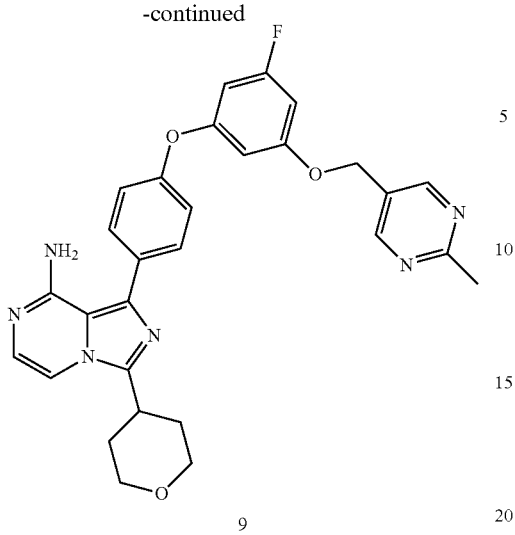

9

A solution of Intermediate 10-a (200 mg, 0.6 mmol), Intermediate 4-b (230 mg, 0.8 mmol), N,N-Dimethylglycine (133 mg, 1.3 mmol), cesium carbonate (630 mg, 1.9 mmol), and copper(I) iodide (81 mg, 0.4 mmol) in 1,4-dioxane (0.8 ml) was heated in a pressure vessel at 110° C. overnight, then cooled to room temperature. Ethyl acetate was added, the reaction was adsorbed on silica gel. Purification by reverse phase chromatography eluting with a 0.1% HCl/methanol gradient provided Compound 9·2HCl as a yellow solid. MS (m/z) M+H=527.3

Synthesis of Compound 4

Scheme 19

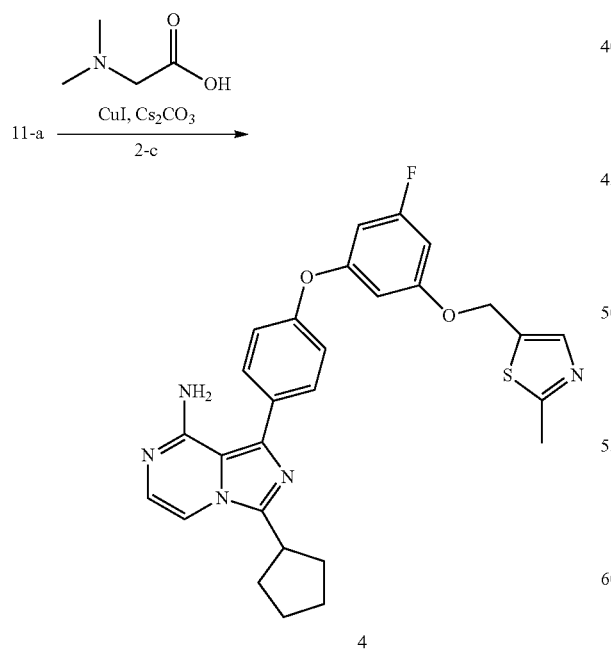

4

A solution of Intermediate 11-a (300 mg, 1.0 mmol), Intermediate 2-c (370 mg, 1.2 mmol), N,N-Dimethylglycine (210 mg, 2.0 mmol), cesium carbonate (996 mg, 3.0 mmol), and copper(I) iodide (128 mg, 0.7 mmol) in 1,4-dioxane (1.3 ml) was heated in a pressure vessel at 110° C. overnight, then cooled to room temperature. Ethyl acetate was added, the reaction was adsorbed on silica gel. Purification by silica gel chromatography provided Compound 4. Compound 4 was dissolved in dichloromethane, 1N HCl in diethyl ether was added, a precipitate formed and was collected by filtration to provide Compound 4·2HCl as a yellow solid. MS (m/z) M+H=516.2

Synthesis of Compound 5

Scheme 20

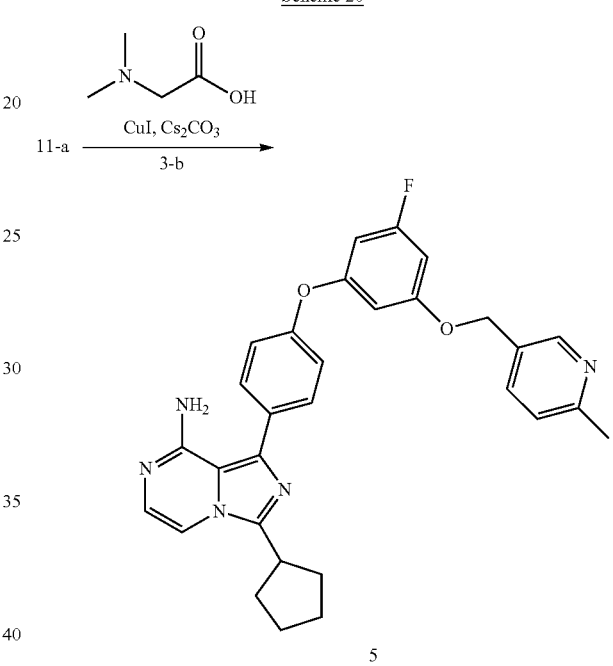

5

A solution of Intermediate 11-a (300 mg, 1.0 mmol), Intermediate 3-b (362 mg, 1.2 mmol), N,N-Dimethylglycine (210 mg, 2.0 mmol), cesium carbonate (996 mg, 3.0 mmol), and copper(I) iodide (128 mg, 0.7 mmol) in 1,4-dioxane (1.3 ml) was heated in a pressure vessel at 110° C. overnight, then cooled to room temperature. Ethyl acetate was added, the reaction was adsorbed on silica gel. Purification by reverse phase chromatography eluting with a 0.1% HCl/methanol gradient provided Compound 5·2HCl as yellow solid. MS (m/z) M+H=510.3

Synthesis of Compound 6

Scheme 21

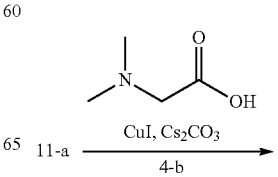

-continued

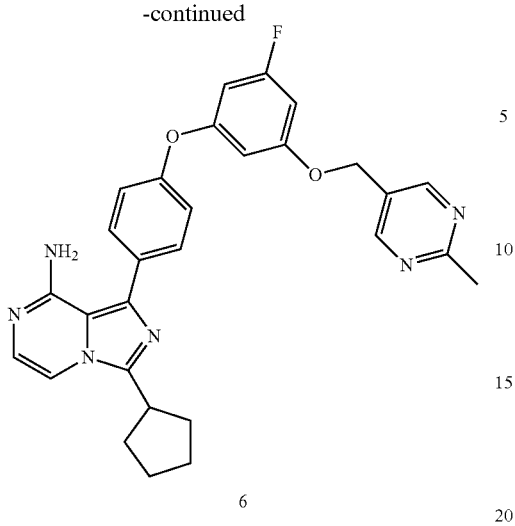

6

A solution of Intermediate 11-a (300 mg, 1.0 mmol), Intermediate 4-b (363 mg, 1.2 mmol), N,N-Dimethylglycine (210 mg, 2.0 mmol), cesium carbonate (996 mg, 3.0 mmol), and copper(I) iodide (128 mg, 0.7 mmol) in 1,4-dioxane (1.3 ml) was heated in a pressure vessel at 110° C. overnight, then cooled to room temperature. Ethyl acetate was added, the reaction was adsorbed on silica gel. Purification by reverse phase chromatography eluting with a 0.1% HCl/methanol gradient provided Compound 6·2HCl as a yellow solid. MS (m/z) M+H=511.3

Synthesis of Compound 10

Scheme 22

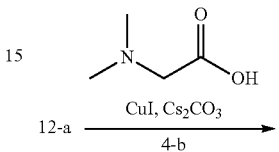

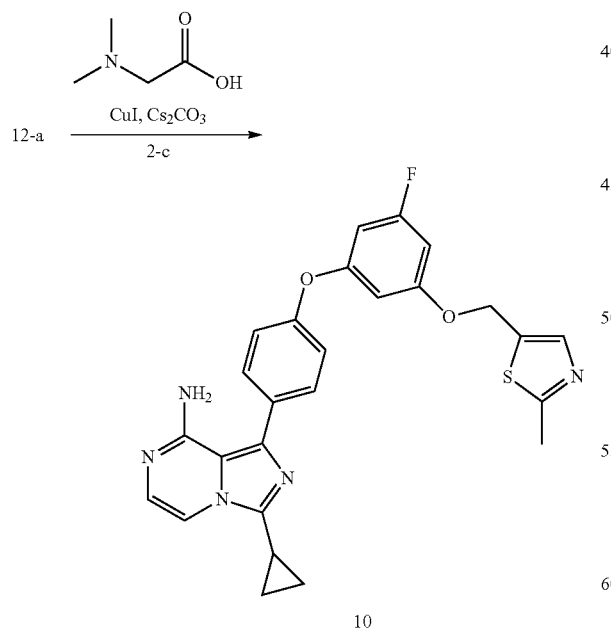

10

A solution of Intermediate 12-a (220 mg, 0.8 mmol), Intermediate 2-c (300 mg, 1.0 mmol), N,N-Dimethylglycine (256 mg, 2.5 mmol), cesium carbonate (1.1 g, 3.3 mmol), and copper(I) iodide (104 mg, 0.5 mmol) in 1,4-dioxane (1.1 ml) was heated in a pressure vessel at 110° C. overnight, then cooled to room temperature. Ethyl acetate was added, the reaction was adsorbed on silica gel. Purification by reverse phase chromatography eluting with a 0.1% HCl/methanol gradient provided Compound 10·2HCl as a yellow solid. MS (m/z) M+H=488.2

Synthesis of Compound 11

Scheme 23

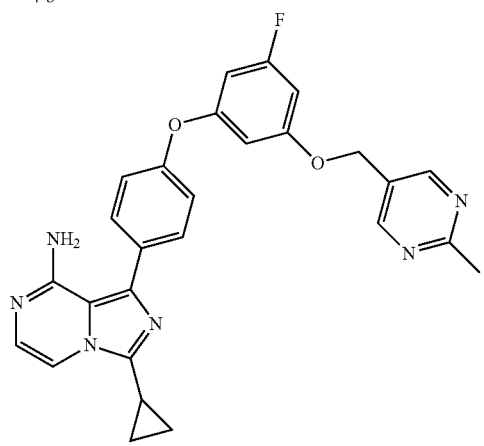

Compound 11

A solution of Intermediate 12-a (270 mg, 1.0 mmol), Intermediate 4-b (362 mg, 1.2 mmol), N,N-Dimethylglycine (314 mg, 3.0 mmol), cesium carbonate (1.3 g, 4.1 mmol), and copper(I) iodide (127 mg, 0.7 mmol) in 1,4-dioxane (1.3 ml) was heated in a pressure vessel at 110° C. overnight, then cooled to room temperature. Ethyl acetate was added, the reaction was adsorbed on silica gel. Purification by reverse phase chromatography eluting with a 0.1% HCl/methanol gradient provided Compound 11·2HCl as a yellow solid. MS (m/z) M+H=483.1

Synthesis of Intermediate 24-b

Scheme 24

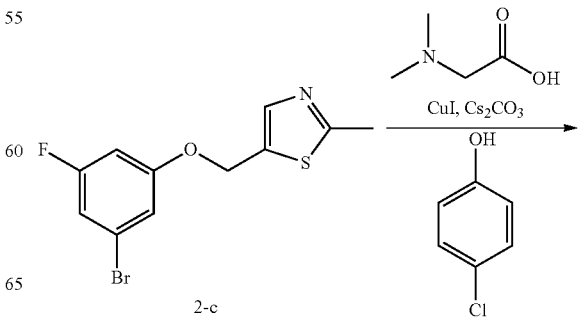

45
-continued

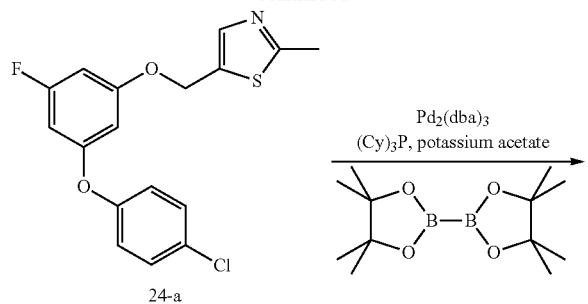

24-a

Pd₂(dba)₃
(Cy)₃P, potassium acetate
→

24-b

Step 1: Intermediate 24-a

A solution of Intermediate 2-c (3.0 g, 9.9 mmol), 4-chlorophenol (1.3 g, 10.4 mmol), N,N-dimethylglycine (3.1 g, 29.8 mmol), cesium carbonate (16.2 g, 49.6 mmol), and copper (I) iodide (1.9 g, 9.9 mmol) in dioxane (28.4 ml) was heated in a pressure vessel at 110° C. for 2 days, and then cooled to room temperature. Ethyl acetate was added; the reaction was filtered over celite, and adsorbed on silica gel. Purification by silica gel chromatography provided Intermediate 24-a as a colorless oil.

Step 2: Intermediate 24-b

To a degassed solution of Intermediate 24-a (1.2 g, 3.6 mmol), 4,4,4',4',5,5,5',5'-octamethyl-2,2'-bi(1,3,2-dioxaborolane (1.1 g, 4.3 mmol), potassium acetate (1.7 g, 17.8 mmol) and tricyclohexylphosphine (200 mg, 0.7 mmol) was added Pd₂(dba)₃ (327 mg, 0.4 mmol) under nitrogen. The reaction was heated in a pressure vessel at 110° C. overnight and then cooled to room temperature. Ethyl acetate was added, the reaction was filtered over celite and adsorbed on silica gel. Purification by silica gel chromatography provided Intermediate 24-b as a yellow solid.

46
Synthesis of Intermediate 25-b

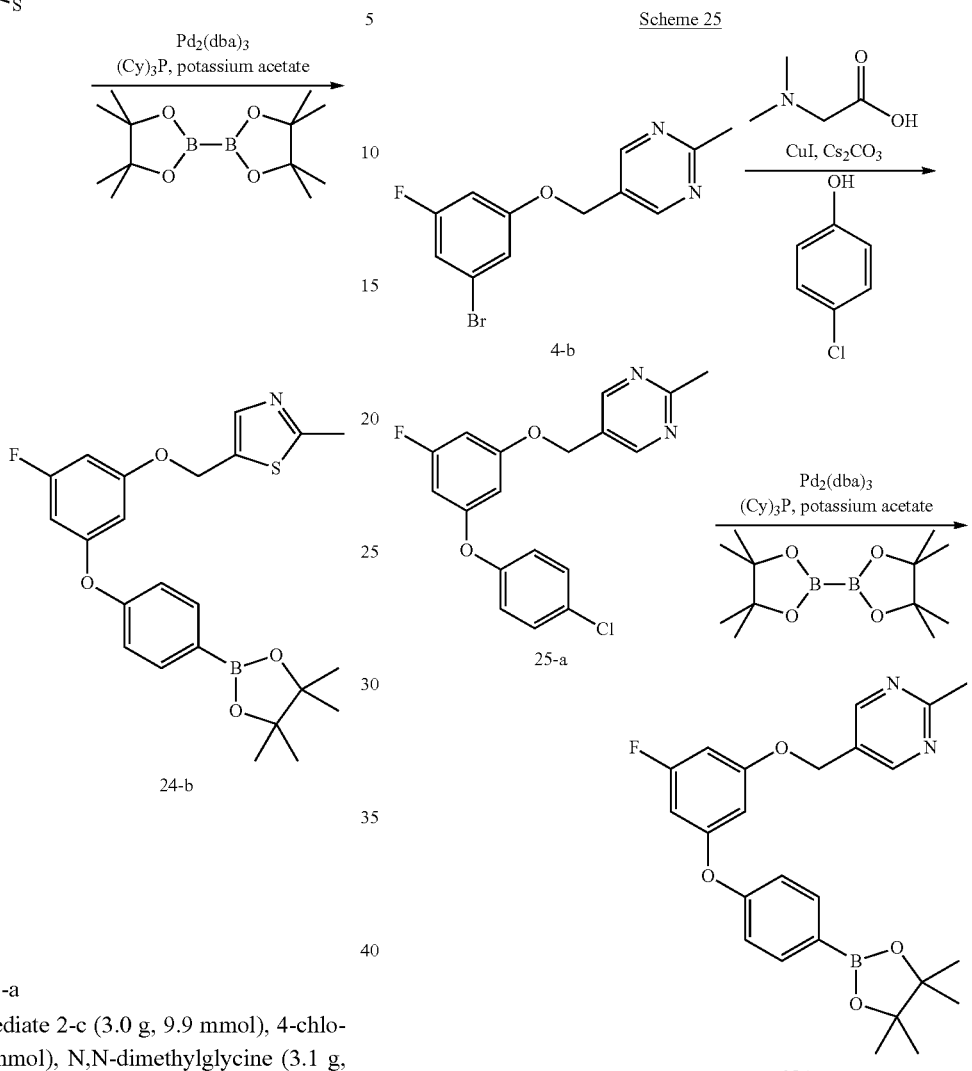

Step 1: Intermediate 25-a

A solution of Intermediate 4-b (1.5 g, 5.0 mmol), 4-chlorophenol (681 mg, 5.3 mmol), N,N-dimethylglycine (1.5 g, 15.1 mmol), cesium carbonate (8.2 g, 25.2 mmol), and copper (I) iodide (961 mg, 5.0 mmol) in dioxane (14.4 ml) was heated in a pressure vessel at 110° C. for 2 days, and then cooled to room temperature. Ethyl acetate was added, the reaction was adsorbed on silica gel. Purification by silica gel chromatography provided Intermediate 25-a as a colorless oil.

Step 2: Intermediate 25-b

To a degassed solution of Intermediate 25-a (5.3 g, 15.4 mmol), 4,4,4',4',5,5,5',5'-octamethyl-2,2'-bi(1,3,2-dioxaborolane (4.68 g, 18.45 mmol), potassium acetate (4.5 g, 46.1 mmol), and tricyclohexylphosphine (862 mg, 3.1 mmol) was added Pd₂(dba)₃ (1.4 g, 1.5 mmol) under nitrogen. The reaction was heated in a pressure vessel at 110° C. for 2 days, and then cooled to room temperature. Ethyl acetate was added, the reaction was filtered over celite, and reaction was adsorbed on silica gel. Purification by silica gel chromatography provided Intermediate 25-b as a colorless oil.

Synthesis of Intermediate 26-e

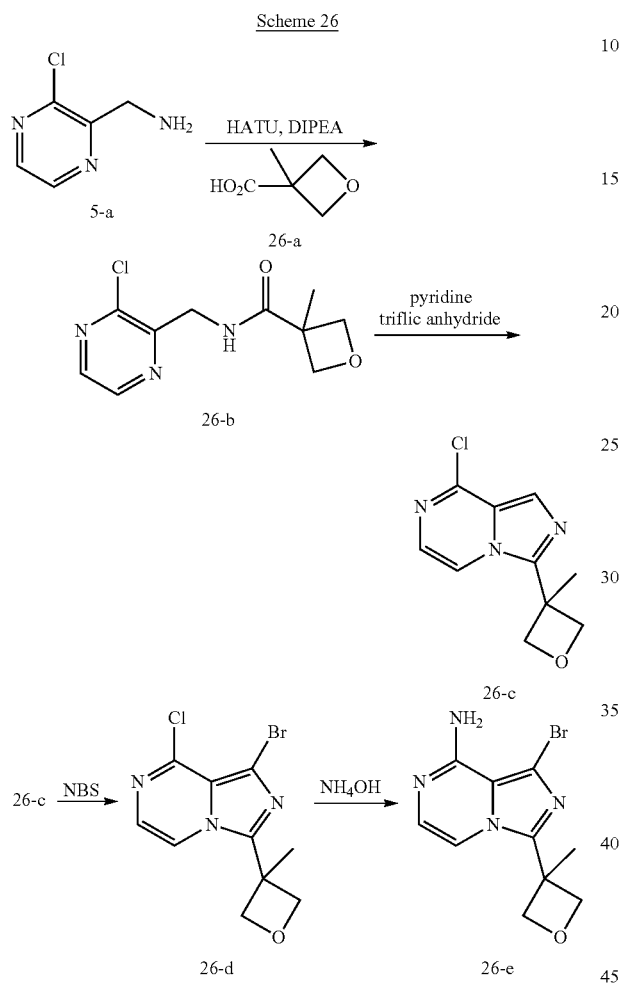

over anhydrous $MgSO_4$, filtered and concentrated under reduced pressure. Purification by silica gel chromatography provided Intermediate 26-c as a yellow foam.

Step 3: Intermediate 26-d

To a solution of Intermediate 26-c (900 mg, 4.0 mmol) in DMF cooled to 0° C. was slowly added a 0.7 N solution of N-bromosuccinimide in DMF (6.3 ml, 4.4 mmol) under an atmosphere of nitrogen. After the addition was completed the reaction mixture was stirred for 15 minutes at 0° C. Water was added; a precipitate formed and was collected by filtration to provide Intermediate 26-d as a white solid.

Step 4: Intermediate 26-e

To a solution of Intermediate 26-d (700 mg, 2.3 mmol) in iPrOH (3.2 ml) was added $NH_4OH$ (4.5 ml), and the reaction mixture was stirred at 90° C. overnight. Volatiles were removed under reduced pressure. Water was added; a precipitate formed and was collected by filtration to provide Intermediate 26-e as a white solid.

Synthesis of Compound 12

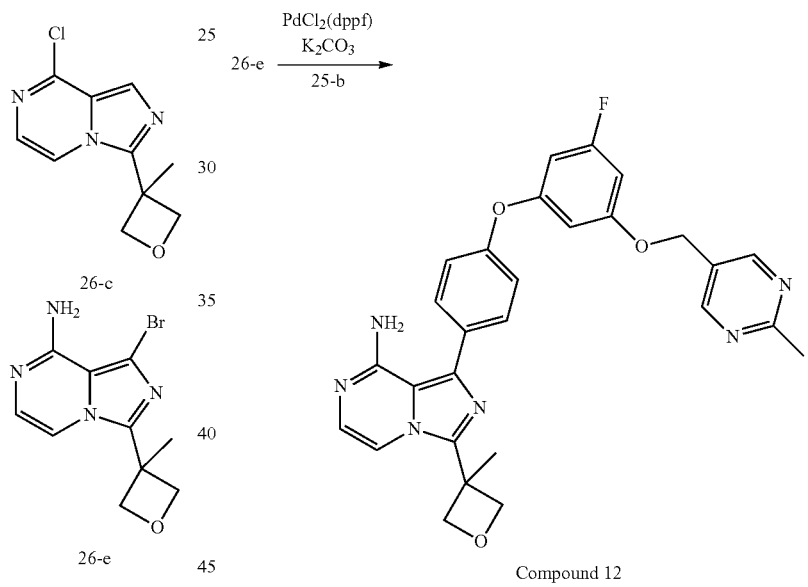

Step 1: Intermediate 26-b

To a solution of (3-chloropyrazin-2-yl)methanamine bis hydrochloride 5-a (2.0 g, 9.2 mmol) in dichloromethane (92.0 ml) cooled to 0° C. were sequentially added 3-methyloxetane-3-carboxylic acid 26-a (1.3 g, 11.1 mmol), HATU (4.2 g, 11.1 mmol), and DIPEA (6.4 ml, 37.0 mmol), and the reaction mixture was stirred for 1 hour at room temperature. Water and ethyl acetate were added; the organic layer was separated, washed with a saturated aqueous solution of ammonium chloride and brine, dried over anhydrous $MgSO_4$, filtered and concentrated under reduced pressure to provide Intermediate 26-b as a yellow solid.

Step 2: Intermediate 26-c

To a solution of Intermediate 26-b (1.7 g, 7.0 mmol) in dichloromethane (23.5 ml) cooled to 0° C. was added pyridine (654 μl, 8.1 mmol) and trifluoromethanesulfonic anhydride (1.3 ml, 7.7 mmol), and the reaction mixture was then stirred for 2 hours at room temperature. A saturated aqueous solution of $NaHCO_3$ and ethyl acetate were added, the organic layer was separated, washed with brine, dried To a degassed solution of Intermediate 26-e (200 mg, 0.7 mmol), Intermediate 25-b (354 mg, 0.8 mmol), and potassium carbonate (293 mg, 2.1 mmol) in DME (3.7 ml), and water (940 μl) was added $PdCl_2(dppf)$ (26 mg, 0.03 mmol). The reaction was heated in a pressure vessel at 120° C. for 4 days, and then cooled to room temperature. Ethyl acetate was added, the reaction was adsorbed on silica gel. Purification by reverse phase chromatography eluting with a 0.1% formic acid/methanol gradient provided Compound 12 as a white solid. MS (m/z) M+H=513.2

Synthesis of Compound 15

Scheme 28

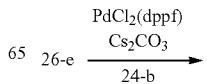

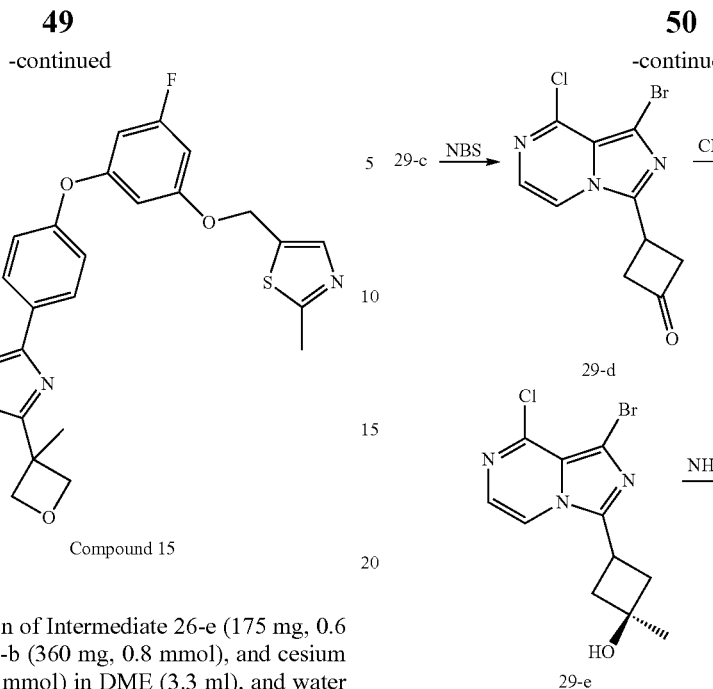

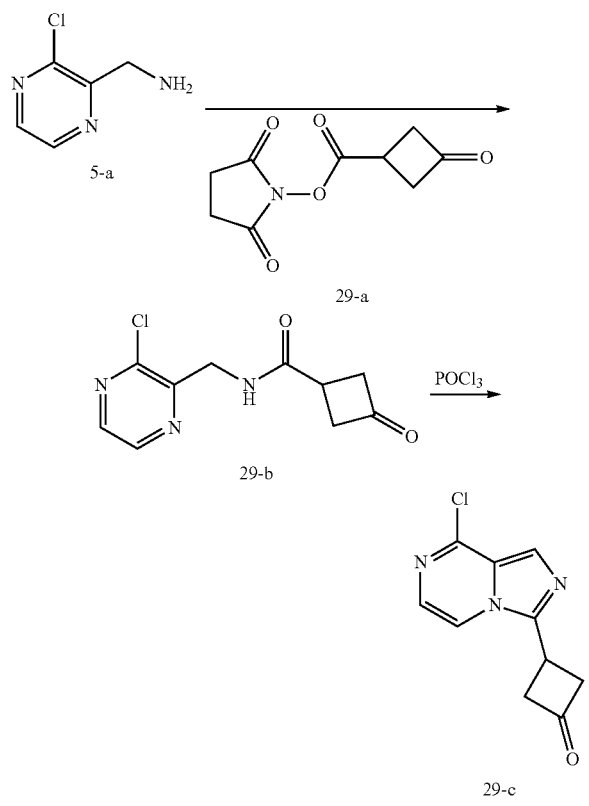

Compound 15

To a degassed solution of Intermediate 26-e (175 mg, 0.6 mmol), Intermediate 24-b (360 mg, 0.8 mmol), and cesium carbonate (604 mg, 1.8 mmol) in DME (3.3 ml), and water (824 μl) was added PdCl$_2$(dppf) (45 mg, 0.06 mmol). The reaction was heated in a pressure vessel at 90° C. overnight, and then cooled to room temperature. Ethyl acetate was added, the reaction was adsorbed on silica gel. Purification by reverse phase chromatography eluting with a 0.1% formic acid/methanol gradient provided Compound 15 as a white solid. MS (m/z) M+H=518.2

Synthesis of Intermediate 29-f

Scheme 29

Step 1: Intermediate 29-b

To a solution of (3-chloropyrazin-2-yl)methanamine bis hydrochloride 5-a (3.3 g, 15.1 mmol) in THF (60.3 ml) cooled to 0° C. were sequentially added 3-Intermediate 29-a (3.5 g, 16.6 mmol), and a saturated aqueous solution of sodium bicarbonate (17.6 ml), and the reaction mixture was stirred for 2 hours at room temperature. Water and ethyl acetate were added, the organic layer was separated, washed with brine, dried over anhydrous MgSO$_4$, filtered and concentrated under reduced pressure to provide Intermediate 29-b as a white solid.

Step 2: Intermediate 29-c

To a solution of Intermediate 29-b (3.2 g, 13.3 mmol) in ethyl acetate (41.7 ml) cooled to 10° C. was added DMF (2.8 ml) and phosphorous oxychloride (2.2 ml, 24.0 mmol) dropwise. After the addition was completed, the reaction mixture was stirred for 45 minutes at room temperature. An ice cooled saturated aqueous solution of Na$_2$CO$_3$ and dichloromethane were slowly added, the organic layer was separated, the aqueous phase was extracted twice with dichloromethane, the combined organic extracts were washed with brine, dried over anhydrous MgSO$_4$, filtered and concentrated under reduced pressure to provide Intermediate 29-c as a white solid.

Step 3: Intermediate 29-d

To a solution of Intermediate 29-c (2.7 g, 12.2 mmol) in DMF cooled to 0° C. was slowly added a 0.7 N solution of N-bromosuccinimide in DMF (19.1 ml, 13.4 mmol) under an atmosphere of nitrogen. After the addition was completed the reaction mixture was stirred for 15 minutes at 0° C. Water was added; a precipitate formed and was collected by filtration to provide Intermediate 29-d as a white solid.

Step 4: Intermediate 29-e

To a solution of Intermediate 29-d (3.0 g, 9.9 mmol) in THF (24.9 ml) cooled to −78° C. was slowly added methylmagnesium bromide (19.9 ml, 19.9 mmol) under nitrogen. The reaction mixture was stirred for 2 hours at −78° C., quenched by slow addition of a saturated aqueous solution of ammonium chloride, and warmed to room temperature.

Ethyl acetate was added, the organic layer was separated, the aqueous phase was extracted twice with ethyl acetate, the combined organic extracts were brine, dried over anhydrous MgSO$_4$, filtered and concentrated under reduced pressure to provide Intermediate 29-e as a white solid.

Step 5: Intermediate 29-f

To a solution of Intermediate 29-e (1.7 g, 5.4 mmol) in iPrOH (13.4 ml) was added NH$_4$OH (13.4 ml) and the reaction mixture was stirred at 90° C. overnight. Volatiles were removed under reduced pressure. Water was added; a precipitate formed and was collected by filtration to provide Intermediate 29-f as a white solid.

Synthesis of Compound 13

Scheme 30

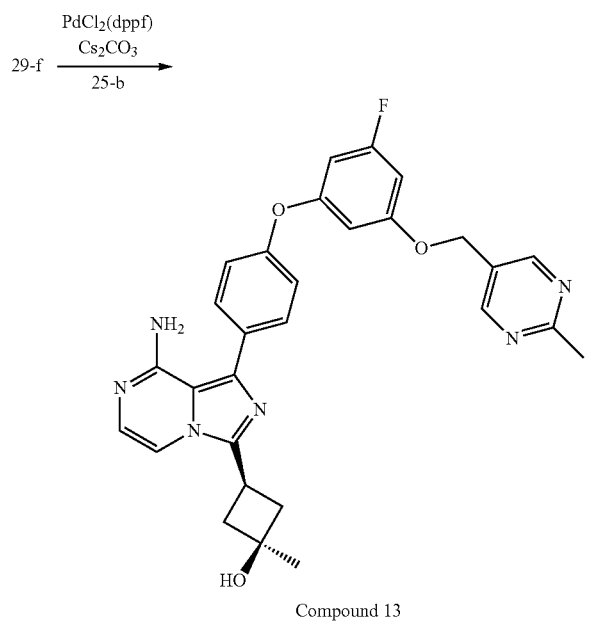

Compound 13

To a degassed solution of Intermediate 29-f (237 mg, 0.8 mmol), Intermediate 25-b (400 mg, 0.9 mmol), and cesium carbonate (779 mg, 2.4 mmol) in DME (4.2 ml), and water (1.1 ml) was added PdCl$_2$(dppf) (58 mg, 0.08 mmol). The reaction was heated in a pressure vessel at 90° C. overnight, and then cooled to room temperature. Ethyl acetate was added, the reaction was adsorbed on silica gel. Purification by reverse phase chromatography eluting with a 0.1% formic acid/methanol gradient provided Compound 13 as a white solid. MS (m/z) M+H=527.2

Synthesis of Compound 16

Scheme 31

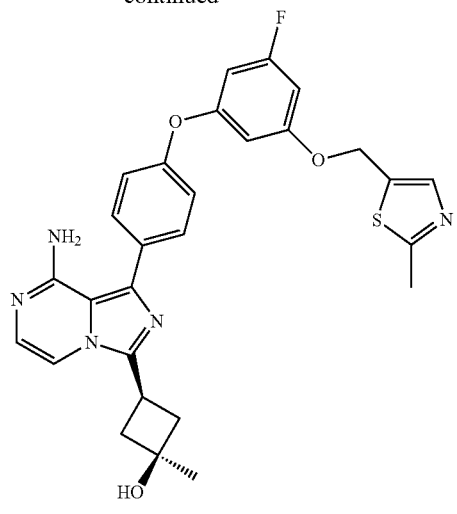

Compound 16

To a degassed solution of Intermediate 29-f (730 mg, 2.4 mmol), Intermediate 24-b (1.5 g, 3.4 mmol), and cesium carbonate (2.4 g, 7.4 mmol) in DME (13.1 ml), and water (3.3 ml) was added PdCl$_2$(dppf) (180 mg, 0.2 mmol). The reaction was heated in a pressure vessel at 90° C. overnight, and then cooled to room temperature. Ethyl acetate was added; the reaction was filtered over celite, and adsorbed on silica gel. Purification by reverse phase chromatography eluting with a 0.1% formic acid/methanol gradient provided Compound 16 as a white solid. MS (m/z) M+H=532.2

Synthesis of Intermediate 32-f

Scheme 32

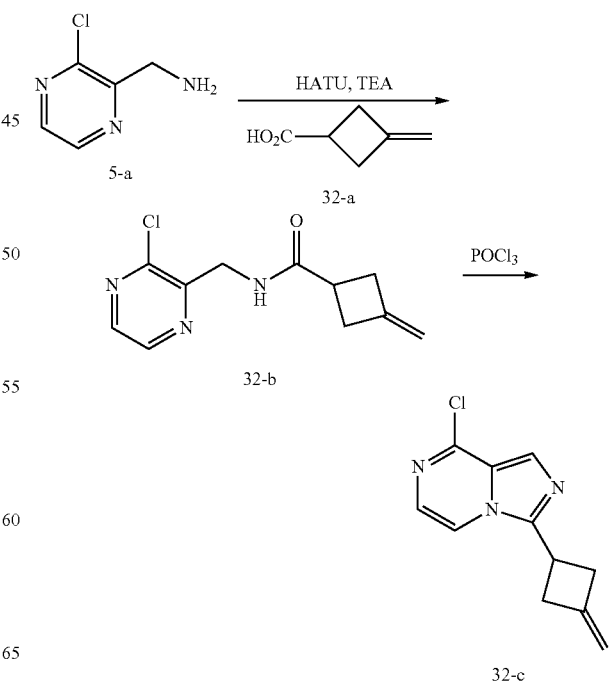

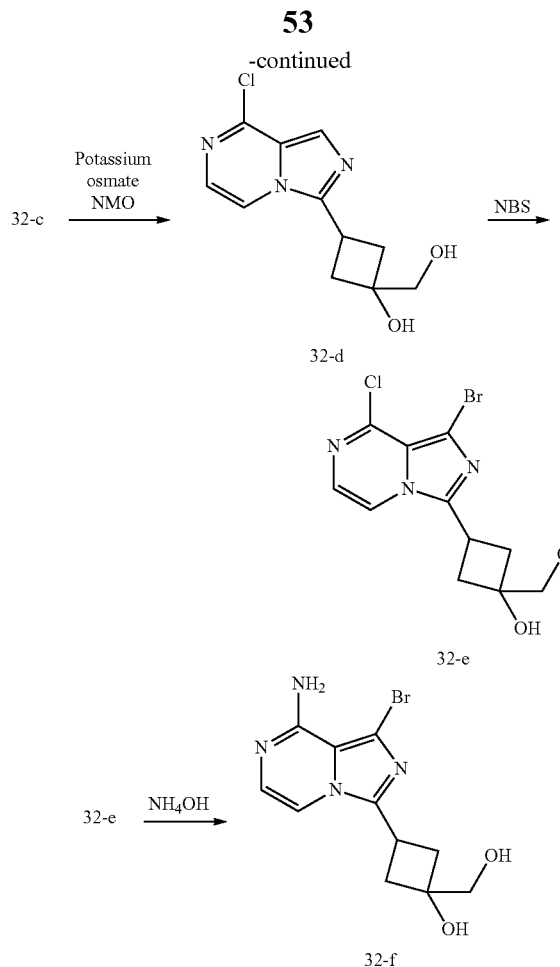

Step 1: Intermediate 32-b

To a solution of (3-chloropyrazin-2-yl)methanamine bis hydrochloride 5-a (5.0 g, 23.1 mmol) in DMF (46.2 ml) cooled to 0° C. were sequentially added 3-methylenecyclobutanecarboxilic acid 32-a (3.1 g, 27.7 mmol), HATU (8.8 g, 23.1 mmol), and TEA (16.1 ml, 115.0 mmol), and the reaction mixture was stirred for 1 hour at room temperature. Water and dichloromethane were added, the organic layer was separated, the aqueous phase was extracted twice with dichloromethane, the combined organic extracts were washed with a saturated aqueous solution of ammonium chloride and brine, dried over anhydrous MgSO$_4$, filtered and concentrated under reduced pressure to provide Intermediate 32-b as a yellow solid.

Step 2: Intermediate 32-c

To a solution of Intermediate 32-b (5.5 g, 23.1 mmol) in ethyl acetate (72.2 ml) cooled to 10° C. was added DMF (4.8 ml), and phosphorous oxychloride (3.9 ml, 41.6 mmol) dropwise. After the addition was completed, the reaction mixture was stirred for 2 hours at room temperature. An ice cooled saturated aqueous solution of Na$_2$CO$_3$, and dichloromethane were slowly added, the organic layer was separated, the aqueous phase was extracted twice with dichloromethane, the combined organic extracts were washed with brine, dried over anhydrous MgSO$_4$, filtered and concentrated under reduced pressure. Purification by silica gel chromatography provided Intermediate 32-c as a white solid.

Step 3: Intermediate 32-d

To a solution of Intermediate 32-c (1.9 g, 8.6 mmol) in THF (72.1 ml) and water (24.0 ml) was added NMO (2.0 g, 17.3 mmol), and potassium osmate dihydrate (159 mg, 0.4 mmol), and the reaction was stirred at room temperature overnight. Sodium sulfite (5.4 g, 43.2 mmol) and water were added, the mixture was extracted 3 times with ethyl acetate, the combined organic extracts were washed with brine, dried over anhydrous MgSO$_4$, filtered and concentrated under reduced pressure to provide Intermediate 32-d as a beige solid Step 4: Intermediate 32-e To a solution of Intermediate 32-d (1.3 g, 5.1 mmol) in DMF cooled to 0° C. was slowly added a 0.7 N solution of N-bromosuccinimide in DMF (8.0 ml, 5.6 mmol) under an atmosphere of nitrogen. After the addition was completed the reaction mixture was stirred for 1 hour at 0° C. Water and dichloromethane were added, the organic layer was separated, the aqueous phase was extracted twice with dichloromethane, the combined organic extracts were washed with a saturated aqueous solution of ammonium chloride and brine, dried over anhydrous MgSO$_4$, filtered and concentrated under reduced pressure to provide Intermediate 32-e as a yellow oil.

Step 5: Intermediate 32-f

To a solution of Intermediate 32-e (1.7 g, 5.1 mmol) in iPrOH (7.1 ml) was added NH$_4$OH (10.0 ml) and the reaction mixture was stirred at 95° C. overnight. Volatiles were removed under reduced pressure. Water was added; a precipitate formed and was collected by filtration. Purification by reverse phase chromatography eluting with a 0.1% formic acid/methanol gradient provided Intermediate 32-f as a yellow solid.

Synthesis of Compound 19

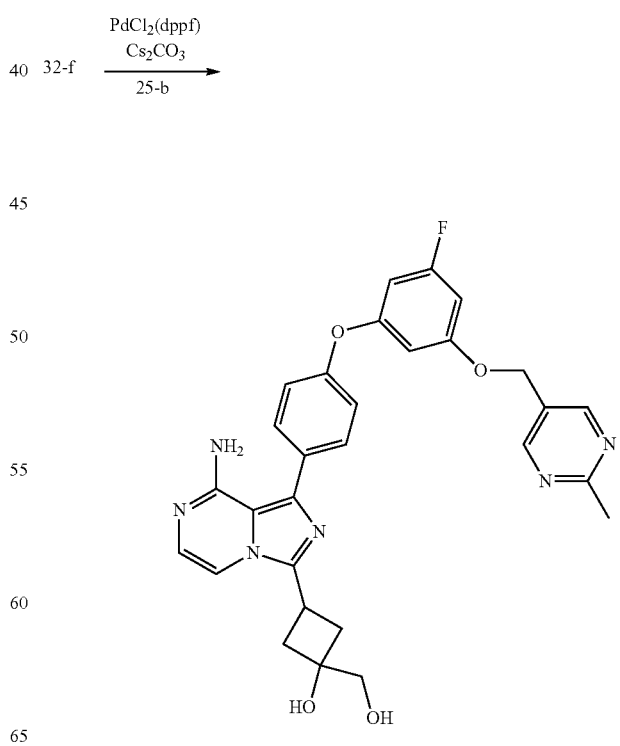

Compound 19

To a degassed solution of Intermediate 32-f (144 mg, 0.5 mmol), Intermediate 25-b (221 mg, 0.5 mmol), and cesium carbonate (449 mg, 1.4 mmol) in DME (2.4 ml), and water (613 µl) was added PdCl$_2$(dppf) (34 mg, 0.04 mmol). The reaction was heated in a pressure vessel at 90° C. overnight, and then cooled to room temperature. Ethyl acetate was added; the reaction was filtered over celite, and adsorbed on silica gel. Purification by reverse phase chromatography eluting with a 0.1% formic acid/methanol gradient provided Compound 19 (cis/trans mixture) as a white foam. MS (m/z) M+H=543.1

Synthesis of Compound 14

Scheme 34

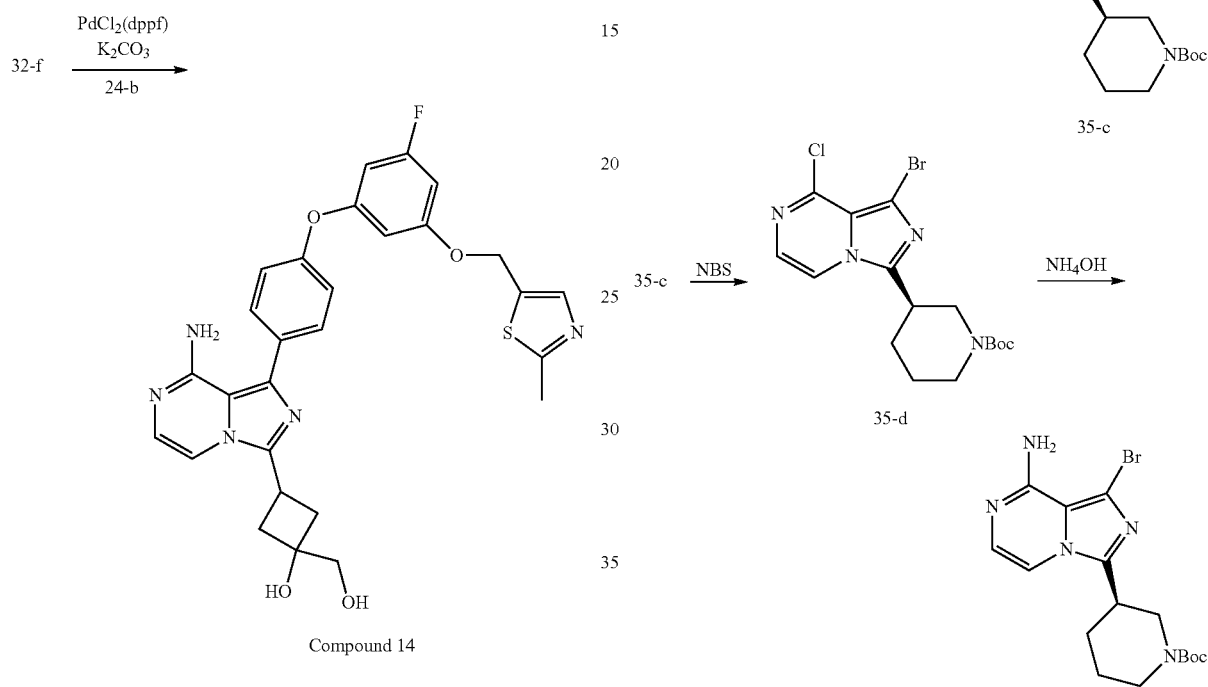

Compound 14

To a degassed solution of Intermediate 32-f (150 mg, 0.5 mmol), Intermediate 24-b (233 mg, 0.5 mmol), and cesium carbonate (468 mg, 1.4 mmol) in DME (2.5 ml), and water (639 µl) was added PdCl$_2$(dppf) (35 mg, 0.05 mmol). The reaction was heated in a pressure vessel at 95° C. overnight, and then cooled to room temperature. Ethyl acetate was added; the reaction was filtered over celite, and adsorbed on silica gel. Purification by reverse phase chromatography eluting with a 0.1% formic acid/methanol gradient provided Compound 14 (cis/trans mixture) as a white solid. MS (m/z) M+H=548.1

Synthesis of Intermediate 35-e

Scheme 35

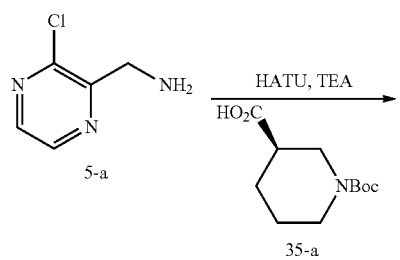

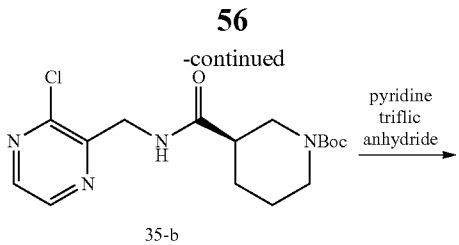

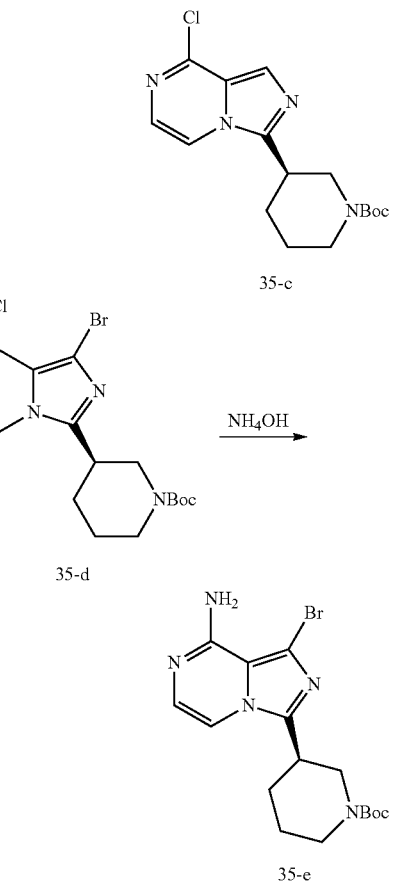

Step 1: Intermediate 35-b

To a solution of (3-chloropyrazin-2-yl)methanamine bis hydrochloride 5-a (2.5 g, 11.5 mmol) in dichloromethane (23.0 ml) cooled to 0° C. were sequentially added (R)-1-(tert-butoxycarbonyl)piperidine-3-carboxylic acid 35-a (2.6 g, 11.5 mmol), HATU (4.4 g, 11.5 mmol), and TEA (8.0 ml, 57.7 mmol), and the reaction mixture was stirred for 4 hours at room temperature. Water and dichloromethane were added, the organic layer was separated, the aqueous phase was extracted twice with dichloromethane, the combined organic extracts were washed with a saturated aqueous solution of ammonium chloride and brine, dried over anhydrous MgSO$_4$, filtered and concentrated under reduced pressure to provide Intermediate 35-b as a yellow oil.

Step 2: Intermediate 35-c

To a solution of Intermediate 35-b (4.0 g, 11.3 mmol) in dichloromethane (37.6 ml) cooled to 0° C. was added pyridine (2.1 ml, 25.9 mmol), and trifluoromethanesulfonic anhydride (2.1 ml, 12.4 mmol), and the reaction mixture was then stirred for 2 hours at room temperature. A saturated aqueous solution of NaHCO$_3$ and ethyl acetate were added, the organic layer was separated, washed with brine, dried over anhydrous MgSO$_4$, filtered and concentrated under reduced pressure. Purification by silica gel chromatography provided Intermediate 35-c as a white foam.

Step 3: Intermediate 35-d

To a solution of Intermediate 35-c (1.4 g, 4.2 mmol) in DMF cooled to 0° C. was slowly added a 0.7 N solution of N-bromosuccinimide in DMF (6.7 ml, 4.7 mmol) under an atmosphere of nitrogen. After the addition was completed the reaction mixture was stirred for 1 hour at 0° C. Water and dichloromethane were added, the organic layer was separated, the aqueous phase was extracted twice with dichloromethane, and the combined organic extracts were washed with a saturated aqueous solution of ammonium chloride and brine, dried over anhydrous MgSO₄, filtered and concentrated under reduced pressure. Purification by silica gel chromatography provided Intermediate 35-d as a white foam.

Step 4: Intermediate 35-e

To a solution of Intermediate 35-d (1.4 g, 3.5 mmol) in iPrOH (4.8 ml) was added NH₄OH (6.8 ml) and the reaction mixture was stirred at 90° C. overnight. Volatiles were removed under reduced pressure. Water was added; a precipitate formed and was collected by filtration to provide Intermediate 35-e as a beige solid.

Synthesis of Compound 23

Scheme 36

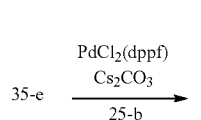

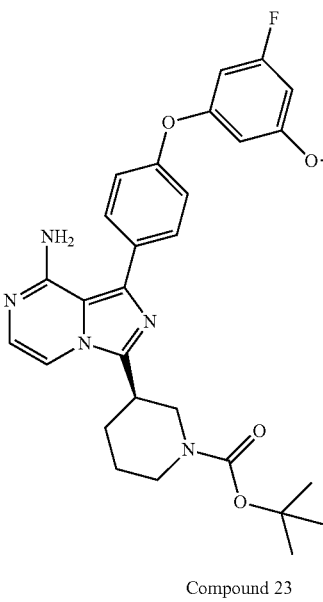

Compound 23

To a degassed solution of Intermediate 35-e (400 mg, 1.0 mmol), Intermediate 25-b (484 mg, 1.1) mmol), and cesium carbonate (987 mg, 3.0 mmol) in DME (5.4 ml), and water (1.4 ml) was added PdCl₂(dppf) (74 mg, 0.1 mmol). The reaction was heated in a pressure vessel at 100° C. overnight, and then cooled to room temperature. Ethyl acetate was added, the reaction was adsorbed on silica gel. Purification by reverse phase chromatography eluting with a 0.1% formic acid/methanol gradient provided Compound 23 as a white solid. MS (m/z) M+H=626.1

Synthesis of Compound 22

Scheme 37

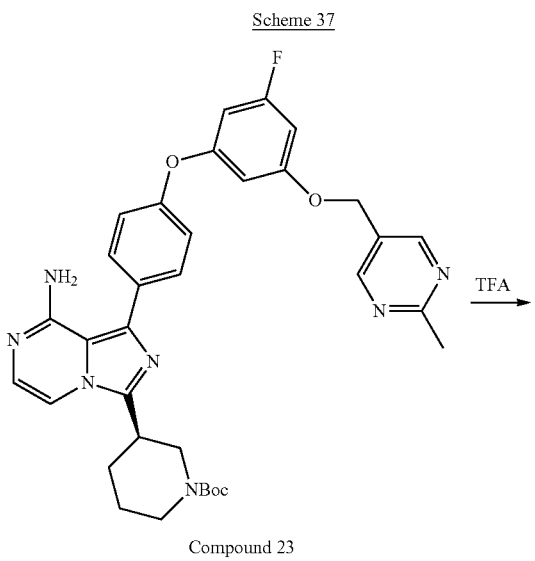

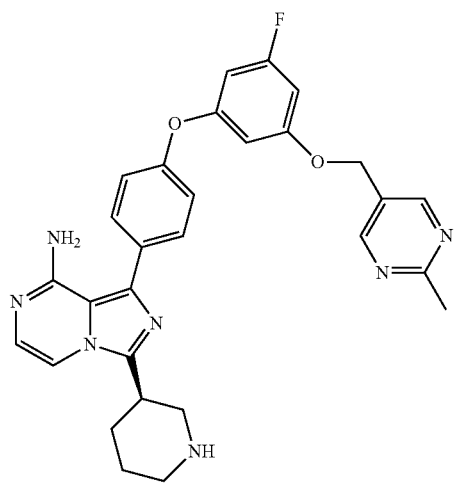

Compound 22

To a solution of Compound 23 (400 mg, 0.6 mmol) in dichloromethane (4.2 ml) was added TFA (4.0 ml, 51.9 mmol) and the solution was stirred at room temperature for 30 minutes. Volatiles were removed under reduced pressure to provide Compound 22·2TFA as a white solid. MS (m/z) M+H=526.1

Synthesis of Compound 24

Scheme 38

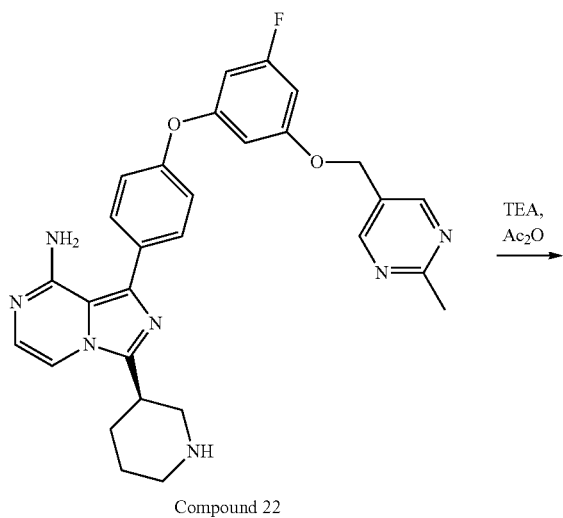

Compound 22

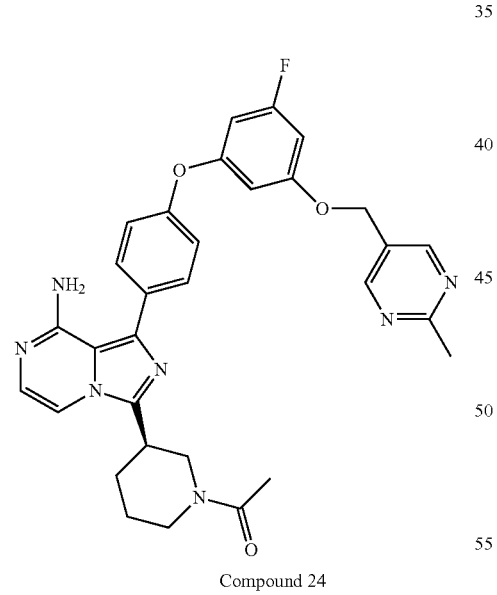

Compound 24

To a solution of Compound 22·2TFA (90 mg, 0.14 mmol) in dichloromethane (1.4 ml) cooled to 0° C. were sequentially added triethylamine (78 µl, 0.5 mmol), and acetic anhydride (141 µl, 0.14 mmol), and the reaction was then stirred at 0° C. for 1 hour. Volatiles were removed under reduced pressure. Purification by reverse phase chromatography eluting with a 0.1% formic acid/methanol gradient provided Compound 24 as a beige solid. MS (m/z) M+H=568.0

Synthesis of Compound 21

Scheme 39

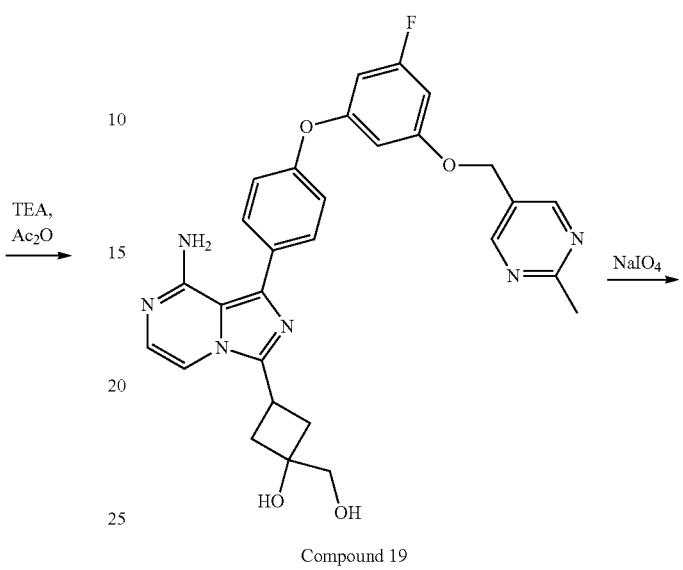

To a solution of Compound 19 (29 mg, 0.05 mmol) THF (668 µl) and water (223 µl) cooled to 0° C., was added sodium periodate (17 mg, 0.08 mmol), the reaction was slowly warmed to room temperature, over a period of 2 hours. Water and ethyl acetate were added, the organic layer was separated, the aqueous phase was extracted twice with ethyl acetate, the combined organic extracts were washed with brine, dried over anhydrous MgSO$_4$, filtered and concentrated under reduced pressure. Purification by reverse phase chromatography eluting with a 0.1% formic acid/methanol gradient provided Compound 21 as a white foam. MS (m/z) M+H=511.1

Synthesis of Intermediate 40-e

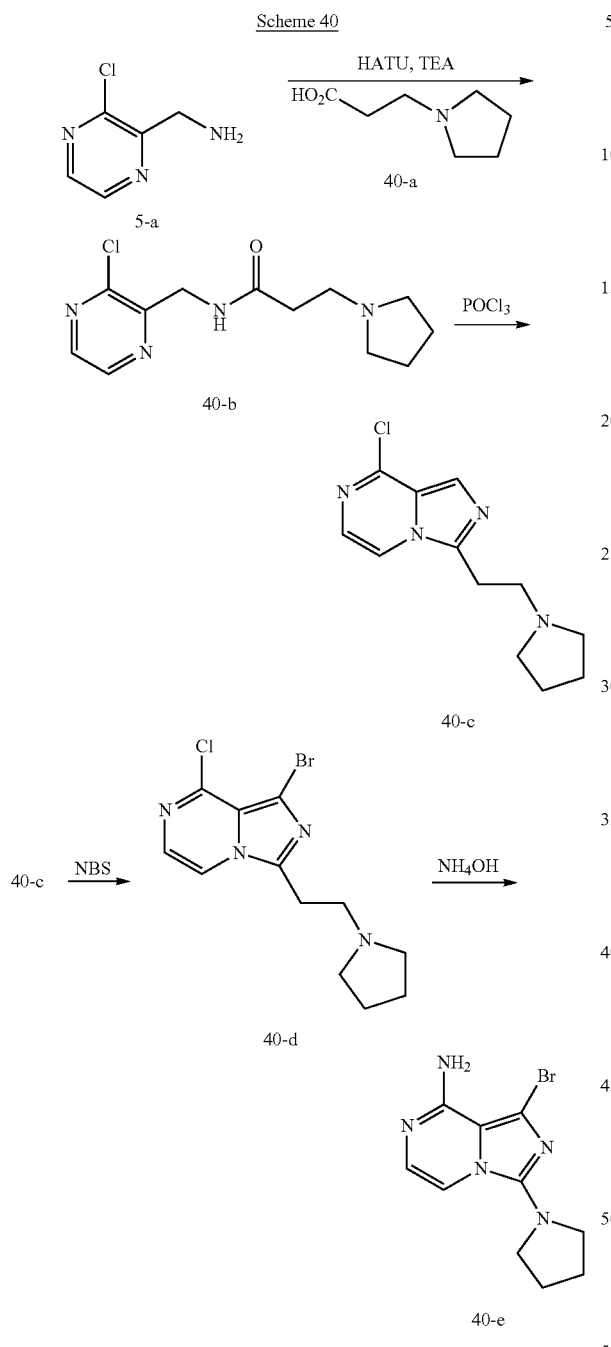

Step 1: Intermediate 40-b

To a solution of (3-chloropyrazin-2-yl)methanamine bis hydrochloride 5-a (3.0 g, 13.8 mmol) in dichloromethane (27.7 ml) cooled to 0° C. were sequentially added 3-(pyrrolidin-1-yl)propanoic acid, HCl 40-a (3.0 g, 16.3 mmol), HATU (5.3 g, 13.9 mmol), and TEA (9.7 ml, 69.3 mmol), the reaction mixture was stirred for 1 hour at room temperature. Water and ethyl acetate were added, the organic layer was separated, washed with brine, dried over anhydrous MgSO$_4$, filtered and concentrated under reduced pressure to provide Intermediate 40-b as a yellow solid.

Step 2: Intermediate 40-c

To a solution of Intermediate 40-b (3.7 g, 13.8 mmol) in ethyl acetate (43.3 ml) cooled to 0° C. was added DMF (2.9 ml), and phosphorous oxychloride (2.3 ml, 24.9 mmol) dropwise. After the addition was completed, the reaction mixture was stirred for 2 hours at room temperature. An ice cooled saturated aqueous solution of Na$_2$CO$_3$ and dichloromethane were slowly added, the organic layer was separated, the aqueous phase was extracted twice with dichloromethane, the combined organic extracts were washed with brine, dried over anhydrous MgSO$_4$, filtered and concentrated under reduced pressure to provide Intermediate 40-c as an orange solid.

Step 3: Intermediate 40-d

To a solution of Intermediate 40-c (1.0 g, 3.9 mmol) in DMF cooled to 0° C. was slowly added a 0.7 N solution of N-bromosuccinimide in DMF (6.3 ml, 4.4 mmol) under an atmosphere of nitrogen. After the addition was completed the reaction mixture was stirred for 1 hour. Water and dichloromethane were added, the organic layer was separated, the aqueous phase was extracted twice with dichloromethane, the combined organic extracts were washed with a saturated aqueous solution of ammonium chloride and brine, dried over anhydrous MgSO$_4$, filtered and concentrated under reduced pressure to provide Intermediate 40-d as a yellow oil.

Step 4: Intermediate 40-e

To a solution of Intermediate 40-d (1.3 g, 3.9 mmol) in iPrOH (5.5 ml) was added NH$_4$OH (7.8 ml) and the reaction mixture was stirred at 90° C. for 2 days. Volatiles were removed under reduced pressure. Water and ethyl acetate were added to the residue, the organic layer was separated, washed with brine, dried over anhydrous MgSO$_4$, filtered and concentrated under reduced pressure. Purification by reverse phase chromatography eluting with a 0.1% HCl/methanol gradient provided Intermediate 40-e·HCl as a yellow oil.

Synthesis of Compound 18

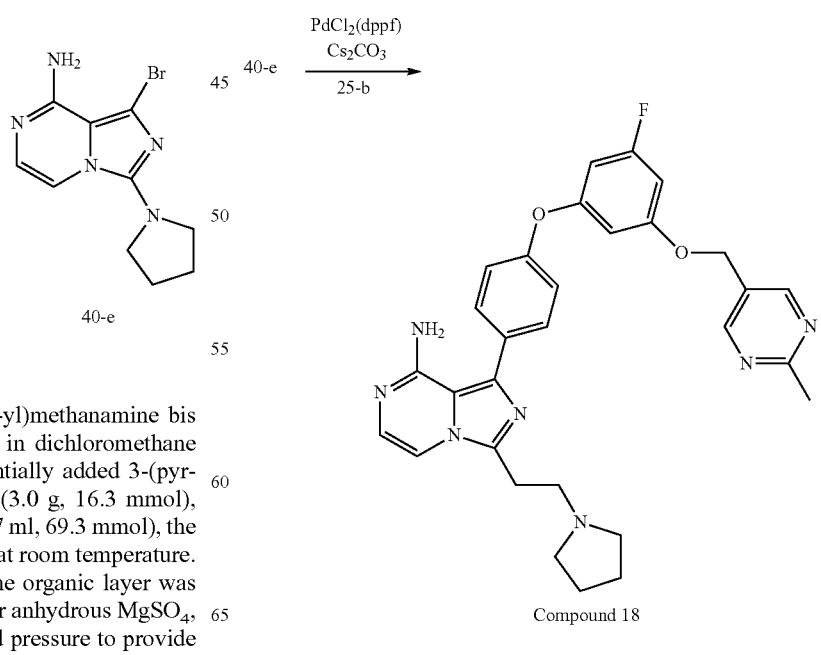

To a degassed solution of Intermediate 40-e·HCl (75 mg, 0.2 mmol), Intermediate 25-b (121 mg, 0.28 mmol), and cesium carbonate (315 mg, 0.9 mmol) in DME (1.3 ml) and water (0.3 ml) was added PdCl$_2$(dppf) (18 mg, 0.02 mmol), the reaction was heated in a pressure vessel at 100° C. overnight, and then cooled to room temperature. Ethyl acetate was added, the reaction was adsorbed on silica gel. Purification by reverse phase chromatography eluting with a 0.1% formic acid/methanol gradient provided Compound 18 as a white solid. MS (m/z) M+H=540.2

Synthesis of Intermediate 42-e

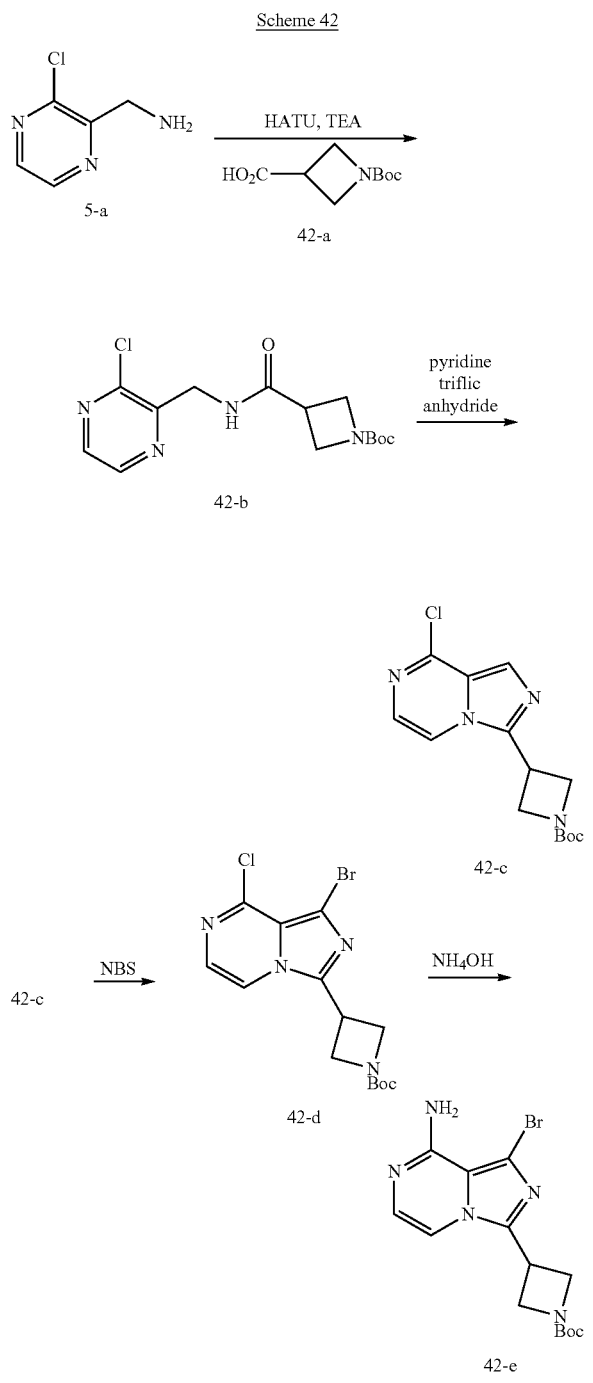

Step 1: Intermediate 42-b

To a solution of (3-chloropyrazin-2-yl)methanamine bis hydrochloride 5-a (3.2 g, 14.9 mmol) in DMF (24.8 ml) cooled to 0° C. were sequentially added 1-(tert-butoxycarbonyl)azetidine-3-carboxylic acid 42-a (3.0 g, 14.9 mmol), HATU (5.6 g, 14.9 mmol), and TEA (10.4 ml, 74.5 mmol), and the reaction mixture was stirred for 4 hours at room temperature. Water and dichloromethane were added, the organic layer was separated, the aqueous phase was extracted twice with dichloromethane, the combined organic extracts were washed with a saturated aqueous solution of ammonium chloride and brine, dried over anhydrous MgSO$_4$, filtered and concentrated under reduced pressure. Purification by silica gel chromatography provided Intermediate 42-b as a yellow oil.

Step 2: Intermediate 42-c

To a solution of Intermediate 42-b (4.9 g, 14.9 mmol) in dichloromethane (49.6 ml) cooled to 0° C. was added pyridine (2.7 ml, 34.3 mmol), and trifluoromethanesulfonic anhydride (2.5 ml, 14.9 mmol), and the reaction mixture was then stirred for 2 hours at room temperature. A saturated aqueous solution of NaHCO$_3$ and ethyl acetate were added, the organic layer was separated, washed with brine, dried over anhydrous MgSO$_4$, filtered and concentrated under reduced pressure. Purification by silica gel chromatography provided Intermediate 42-c as a yellow oil.

Step 3: Intermediate 42-d

To a solution of Intermediate 42-c (1.2 g, 4.0 mmol) in DMF (10 ml) cooled to 0° C. was slowly added a 0.7 N solution of N-bromosuccinimide in DMF (6.3 ml, 4.4 mmol) under an atmosphere of nitrogen. After the addition was completed the reaction mixture was stirred for 1 hour at 0° C. Water and dichloromethane were added, the organic layer was separated, the aqueous phase was extracted twice with dichloromethane, the combined organic extracts were washed with a saturated aqueous solution of ammonium chloride and brine, dried over anhydrous MgSO$_4$, filtered and concentrated under reduced pressure. Purification by silica gel chromatography provided Intermediate 42-d as a yellow solid.

Step 4: Intermediate 42-e

To a solution of Intermediate 42-d (1.7 g, 4.3 mmol) in iPrOH (6.0 ml) was added NH$_4$OH (8.4 ml), and the reaction mixture was stirred in pressure vessel overnight at 95° C. and then cooled to room temperature. Volatiles were removed under reduced pressure and the residue was purified by silica gel chromatography to provide Intermediate 42-e as a yellow foam.

Synthesis of Intermediate 43

Scheme 43

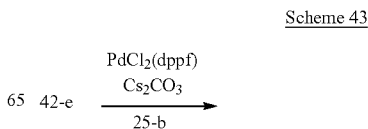

65
-continued

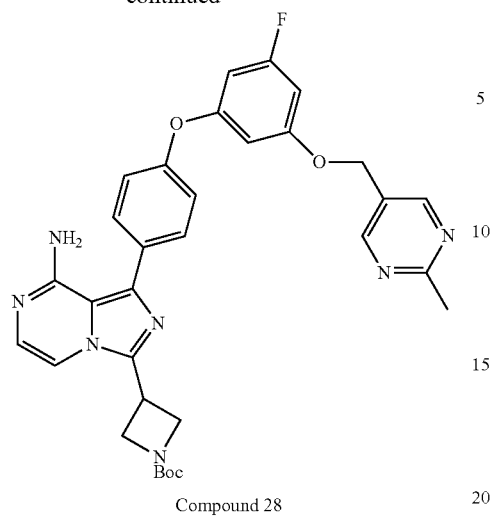
Compound 28

66
-continued

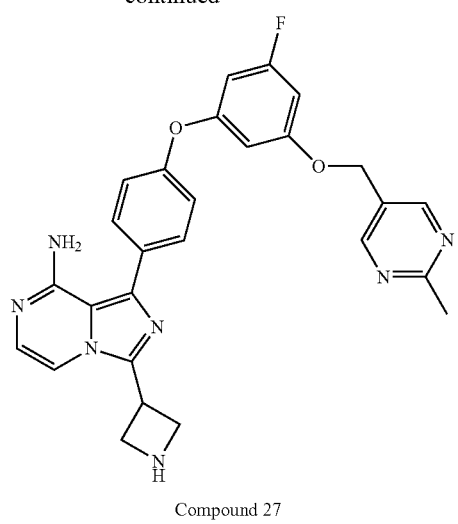
Compound 27

To a degassed solution of Intermediate 42-e (430 mg, 1.2 mmol), Intermediate 25-b (509 mg, 1.2) mmol), and cesium carbonate (1.1 g, 3.5 mmol) in DME (6.2 ml) and water (1.5 ml), was added PdCl$_2$(dppf) (85 mg, 0.11 mmol), and the reaction was heated in a pressure vessel at 100° C. overnight, and then cooled to room temperature. Ethyl acetate was added and the reaction was adsorbed on silica gel. Purification by silica gel chromatography provided Compound 28 as a beige foam. MS (m/z) M+H=598.0

Synthesis of Compound 27

To a solution of Compound 28 (208 mg, 0.3 mmol) in dichloromethane (2.3 ml) was added TFA (2.1 ml, 27.8 mmol), and the solution was stirred at room temperature for 30 minutes. Volatiles were removed under reduced pressure. Purification by reverse phase chromatography eluting with a 0.1% HCl/methanol gradient provided Compound 27.3HCl as yellow solid. MS (m/z) M+H=498.1

Synthesis of Compound 26

Scheme 44

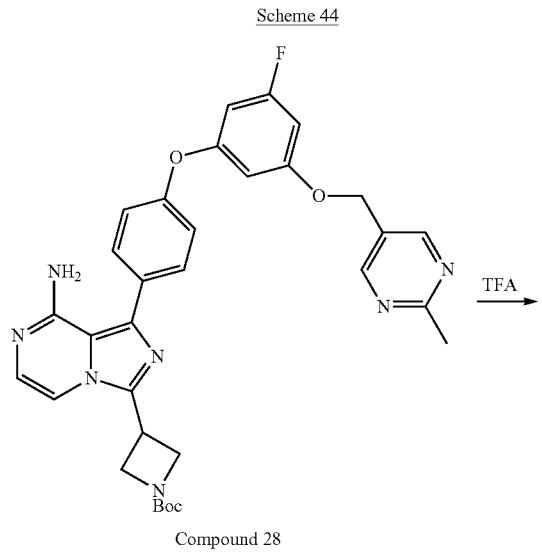
Compound 28
→ TFA

Scheme 45

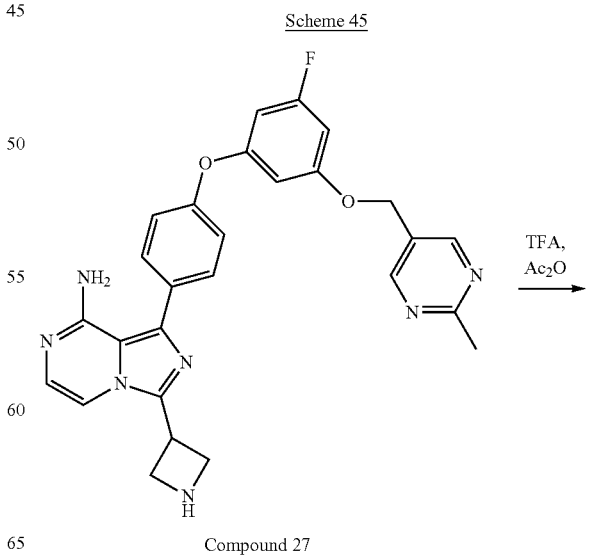
Compound 27
→ TFA, Ac$_2$O

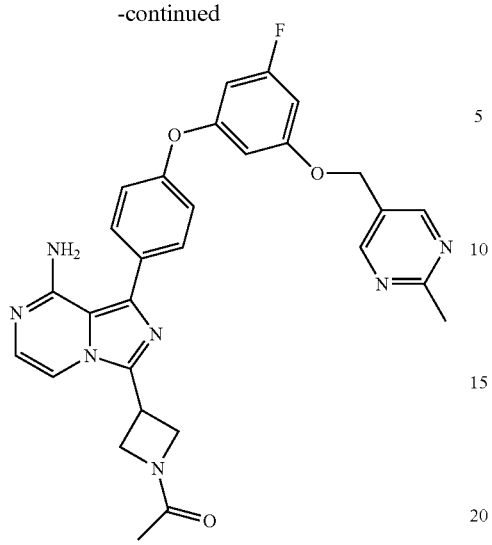

Compound 26

To a solution of Compound 27·2TFA (105 mg, 0.17 mmol) in dichloromethane (1.7 ml) cooled to 0° C. were sequentially added triethylamine (96 μl, 0.7 mmol) and acetic anhydride (172 μl, 0.17 mmol), and the reaction was then stirred at 0° C. for 1 hour. Volatiles were removed under reduced pressure. Purification by reverse phase chromatography eluting with a 0.1% formic acid/methanol gradient provided Compound 26 as a beige solid. MS (m/z) M+H=540.0

Synthesis of Intermediate 46-b

Scheme 46

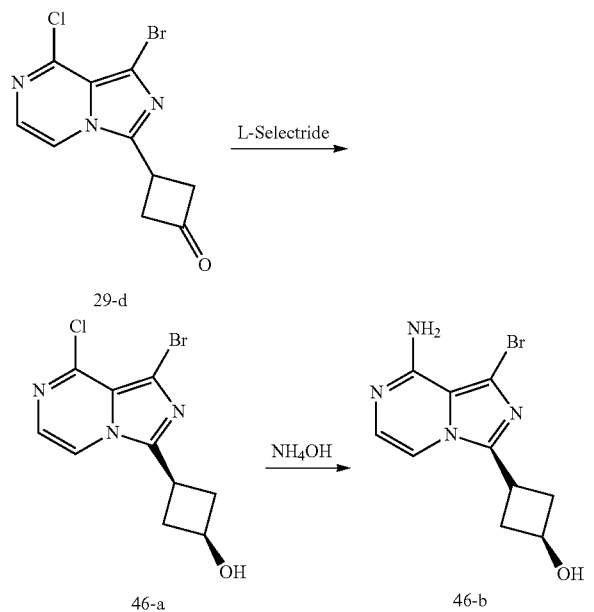

Step 1: Intermediate 46-a

To a solution of Intermediate 29-d (700 mg, 2.3 mmol) in THF (7.8 ml) cooled to −78° C. was added L-Selectride (487 mg, 2.5 mmol), and the reaction was then stirred at −78° C. for 1 hour. A saturated aqueous solution of NaHCO₃ (1 ml) was added dropwise. The mixture was then warmed to 0° C. and a 30% aqueous solution of H₂O₂ (300 μl) was slowly added while maintaining the temperature between 25-30° C. Water and ethyl acetate were added, the organic layer was separated, washed with brine, dried over anhydrous MgSO₄, filtered and concentrated under reduced pressure to provide Intermediate 46-a as a yellow oil.

Step 2: Intermediate 46-b

To a solution of Intermediate 46-a (705 mg, 2.3 mmol) in iPrOH (3.2 ml) was added NH₄OH (4.5 ml), and the reaction mixture was stirred in pressure vessel overnight at 95° C. and then cooled to room temperature. Volatiles were removed under reduced pressure. Water was added to the residue, a precipitated formed and was collected by filtration to provide Intermediate 46-b as a beige solid.

Synthesis of compound 29

Scheme 47

46-b $\xrightarrow[\text{25-b}]{\text{PdCl}_2(\text{dppf}) \\ \text{K}_2\text{CO}_3}$

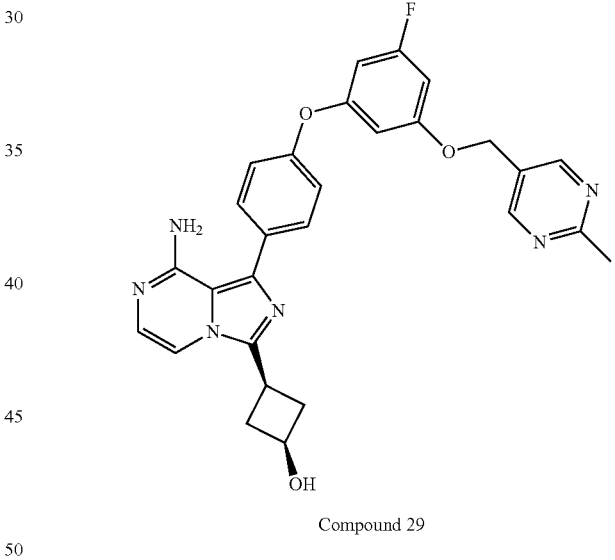

Compound 29

To a degassed solution of Intermediate 46-b (360 mg, 1.3 mmol), Intermediate 25-b (610 mg, 1.4 mmol) and potassium carbonate (527 mg, 3.8 mmol) in DME (6.8 ml), and water (1.7 ml), was added PdCl₂(dppf) (93 mg, 0.13 mmol), and the reaction was heated in a pressure vessel at 100° C. overnight, and then cooled to room temperature. A saturated aqueous solution of ammonium chloride and ethyl acetate were added, the organic layer was separated, washed with brine, dried over MgSO₄, filtered and concentrated under reduced pressure. Purification by reverse phase chromatography eluting with a 0.1% formic acid/methanol gradient provided Compound 29 as a white solid. MS (m/z) M+H=513.2

Synthesis of Intermediate 48-e

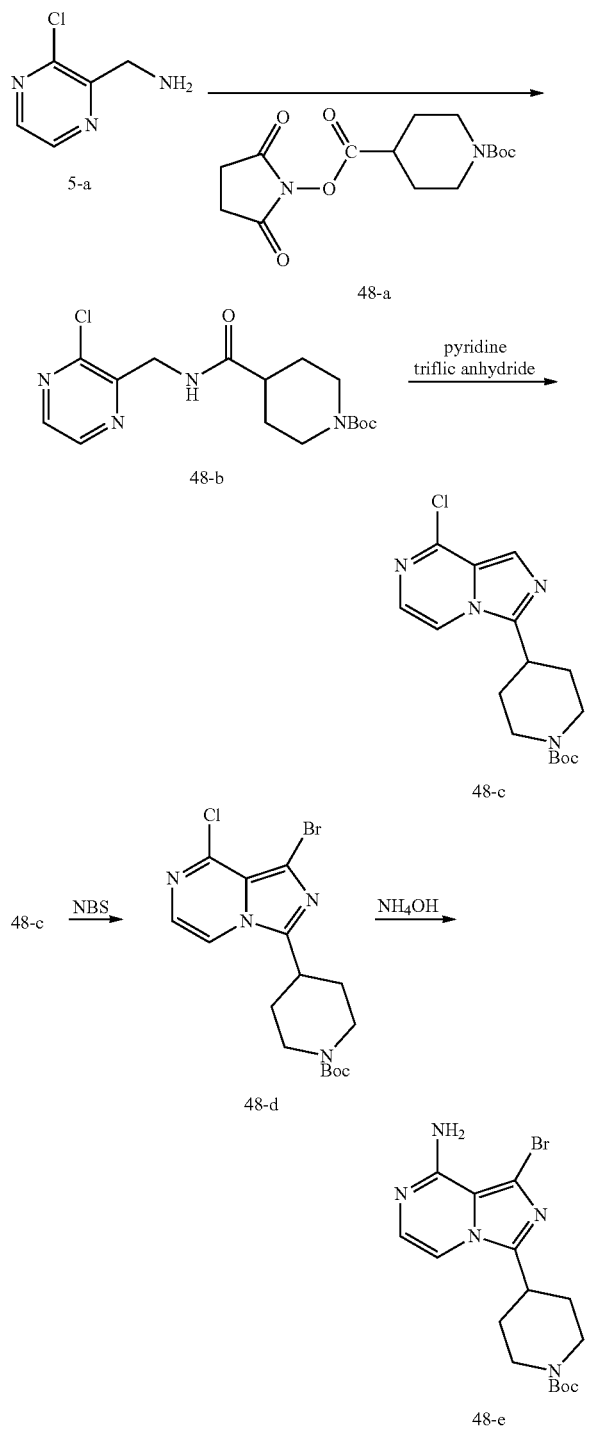

Scheme 48

Step 1: Intermediate 48-b

To a solution of 1-(tert-butoxycarbonyl)piperidine-4-carboxylic acid (2.5 g, 10.9 mmol) in ethyl acetate (21.8 ml) were sequentially added 1-hydroxypyrrolidine-2,5-dione (1.2 g, 10.9 mmol) and DCC (9.0 g, 10.9 mmol). The reaction was stirred at room temperature for 1 hour, and then filtered over celite. Volatiles were removed under reduced pressure to provide Intermediate 48-a as a white solid. To a solution of (3-chloropyrazin-2-yl)methanamine 5-a (2.3 g, 10.7 mmol) in THF (42.9 ml) were sequentially added Intermediate 48-a (3.5 g, 10.7 mmol) and an aqueous solution of sodium bicarbonate (1.7M, 13.2 ml, 22.5 mmol), and the reaction was then stirred for 2 hours at room temperature. Water and ethyl acetate were added, the organic layer was separated, washed with brine, dried over $MgSO_4$, filtered and concentrated under reduced pressure to provide Intermediate 48-b as a beige solid.

Step 2: Intermediate 48-c

To a solution of Intermediate 48-b (3.4 g, 9.6 mmol) in dichloromethane (31.9 ml) cooled to 0° C. was added pyridine (1.8 ml, 22.0 mmol), and trifluoromethanesulfonic anhydride (1.8 ml, 10.5 mmol), and the reaction mixture was then stirred for 2 hours at room temperature. A saturated aqueous solution of $NaHCO_3$ and ethyl acetate were added, the organic layer was separated, the aqueous phase was extracted twice with ethyl acetate, the combined organic extracts were washed with brine, dried over anhydrous $MgSO_4$, filtered and concentrated under reduced pressure. Purification by silica gel chromatography provided Intermediate 48-c as a white foam.

Step 3: Intermediate 48-d

To a solution of Intermediate 48-c (1.5 g, 4.6 mmol) in DMF (11.5 ml) cooled to 0° C. was slowly added a 0.7 N solution of N-bromosuccinimide in DMF (7.2 ml, 5.0 mmol) under an atmosphere of nitrogen. After the addition was completed the reaction mixture was stirred for 1 hour at 0° C. Water and dichloromethane were added, the organic layer was separated, the aqueous phase was extracted twice with dichloromethane, the combined organic extracts were washed with a saturated aqueous solution of ammonium chloride and brine, dried over anhydrous $MgSO_4$, filtered and concentrated under reduced pressure. Purification by silica gel chromatography provided Intermediate 48-d as a white foam.

Step 4: Intermediate 48-e

To a solution of Intermediate 48-d (1.5 g, 3.6 mmol) in iPrOH (5.0 ml) was added $NH_4OH$ (7.0 ml) and the reaction mixture was stirred in pressure vessel overnight at 95° C., and then cooled to room temperature. Volatiles were removed under reduced pressure. Water was added to the residue, a precipitate formed and was collected by filtration to provide Intermediate 48-e as a beige solid.

Synthesis of Compound 32:

Scheme 49

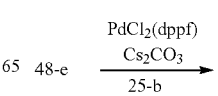

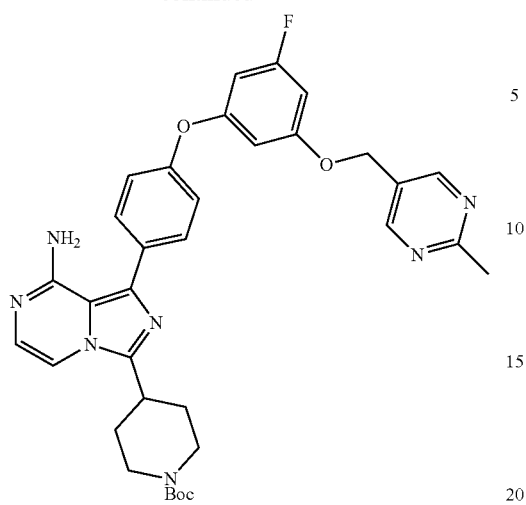

Compound 32

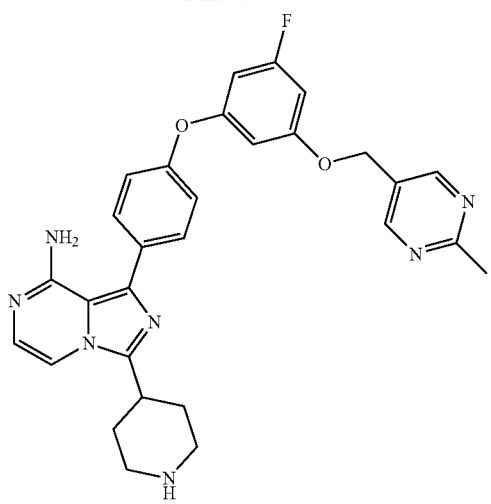

Compound 30

To a degassed solution of Intermediate 48-e (400 mg, 1.0 mmol), Intermediate 25-b (462 mg, 1.1 mmol) and cesium carbonate (987 mg, 3.0 mmol) in DME (5.4 ml) and water (1.3 ml), was added PdCl$_2$(dppf) (74 mg, 0.10 mmol), and the reaction was heated in a pressure vessel at 100° C. overnight, and then cooled to room temperature. Ethyl acetate was added, the reaction was filtered over celite. The filtrate was concentrated under reduced pressure. Purification by silica gel chromatography provided Compound 32 as a white foam. MS (m/z) M+H=626.1.

Synthesis of Compound 30

To a solution of Compound 32 (230 mg, 0.4 mmol) in dichloromethane (2.4 ml) was added TFA (2.2 ml, 29.4 mmol), and the solution was stirred at room temperature for 30 minutes. Volatiles were removed under reduced pressure. Purification by reverse phase chromatography eluting with a 0.1% HCl/methanol gradient provided Compound 30·3HCl as white solid. MS (m/z) M+H=526.1

Synthesis of Compound 31

Scheme 50

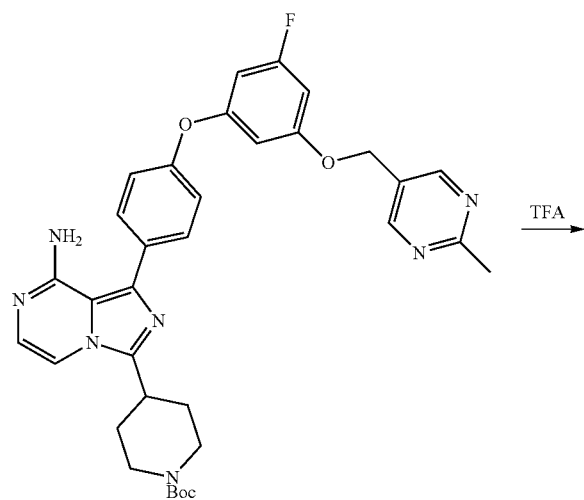

Compound 32

Scheme 51

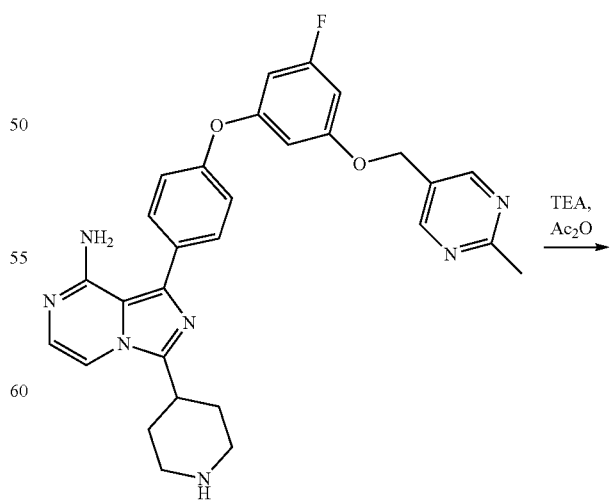

Compound 30

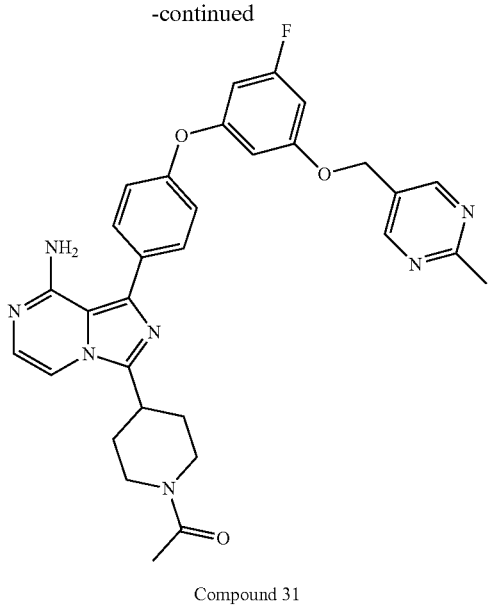

Compound 31

To a solution of Compound 30·2TFA (103 mg, 0.16 mmol) in dichloromethane (1.6 ml) cooled to 0° C. were sequentially added triethylamine (90 μl, 0.6 mmol) and acetic anhydride (15 μl, 0.16 mmol), and the reaction was then stirred at 0° C. for 1 hour. Volatiles were removed under reduced pressure. Purification by reverse phase chromatography eluting with a 0.1% HCl/methanol gradient provided Compound 31·2HCl as a white solid. MS (m/z) M+H=568.1

Synthesis of Compound 34

Scheme 52

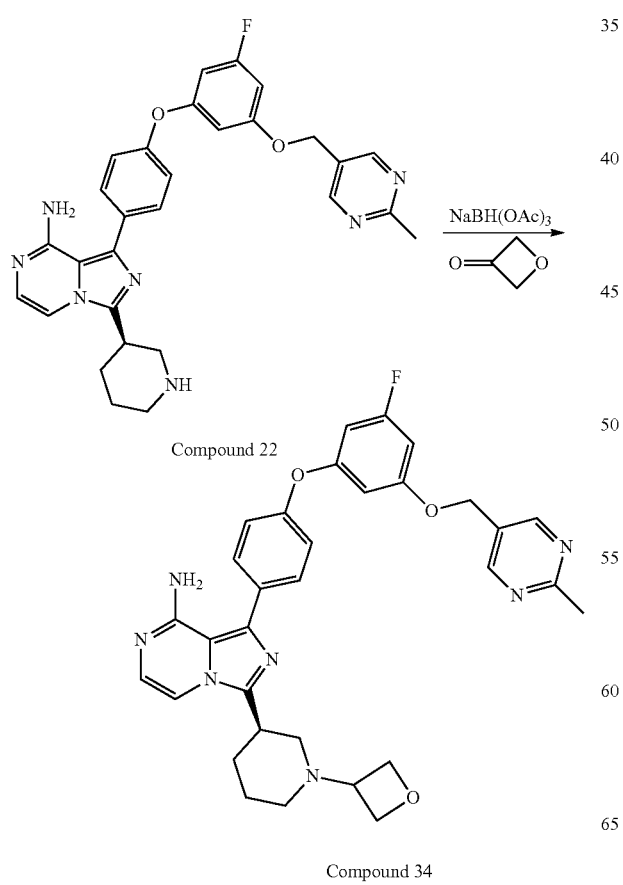

Compound 34

To a solution of Compound 22 (75 mg, 0.1 mmol) in THF (3.6 ml) cooled to 0° C. were sequentially added oxetan-3-one (11 μl, 0.2 mmol) and sodium triacetoxyborohydride (68 mg, 0.3 mmol). The reaction was slowly warmed to room temperature and stirred for 3 days. Volatiles were removed under reduced pressure. A saturated aqueous solution of NaHCO$_3$ and dichloromethane were added to the residue, the organic layer was separated, washed with brine, dried over anhydrous MgSO$_4$, filtered and concentrated under reduced pressure. Purification by silica gel chromatography provided Compound 34 as a yellow solid. MS (m/z) M+H=582.2

Synthesis of Intermediate 53-b

Scheme 53

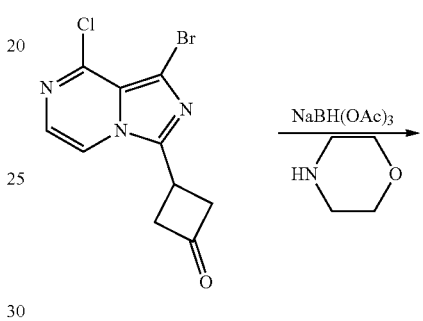

29-d

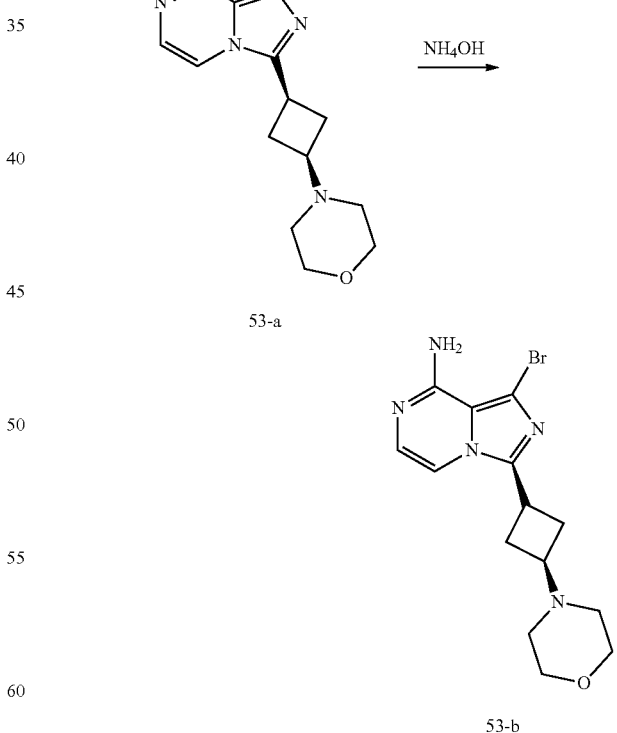

53-a 53-b

Step 1: Intermediate 53-a

To a solution of Intermediate 29-d (760 mg, 2.5 mmol) in THF (25.3 ml) cooled to 0° C. were sequentially added morpholine (218 μl, 2.5 mmol) and sodium triacetoxyborohydride (1.2 g, 5.7 mmol). The reaction was slowly warmed to room temperature and stirred overnight. Volatiles were removed under reduced pressure. A saturated aqueous solution of NaHCO$_3$ and dichloromethane were added to the residue, the organic layer was separated, washed with brine, dried over anhydrous MgSO$_4$, filtered and concentrated under reduced pressure. Purification by silica gel chromatography provided Intermediate 53-a as a yellow oil.

Step 2: Intermediate 53-b

To a solution of Intermediate 53-a (940 mg, 2.5 mmol) in iPrOH (3.5 ml) was added NH$_4$OH (4.9 ml), and the reaction mixture was stirred in pressure vessel overnight at 95° C., and then cooled to room temperature. Volatiles were removed under reduced pressure. Purification by silica gel chromatography provided Intermediate 53-b as a white solid.

Synthesis of Compound 33

Scheme 54

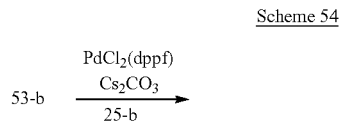

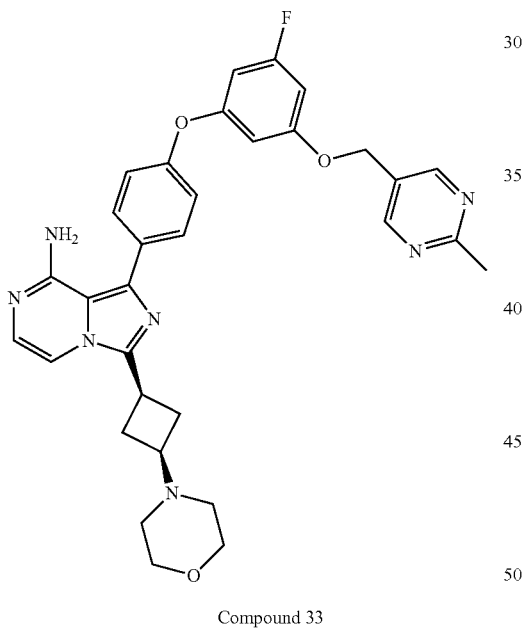

Compound 33

To a degassed solution of Intermediate 53-b (75 mg, 0.2 mmol), Intermediate 25-b (102 mg, 0.2 mmol), and cesium carbonate (208 mg, 0.6 mmol) in DME (1.1 ml) and water (0.3 ml), was added PdCl$_2$(dppf) (16 mg, 0.02 mmol), the reaction was heated in a pressure vessel at 100° C. overnight, and then cooled to room temperature. Ethyl acetate was added and the reaction was filtered over celite. The filtrate was concentrated under reduced pressure. Purification by reverse phase chromatography eluting with a 0.1% formic acid/methanol gradient provided Compound 33 as a beige solid. MS (m/z) M+H=582.2

Synthesis of Compound 17

Scheme 55

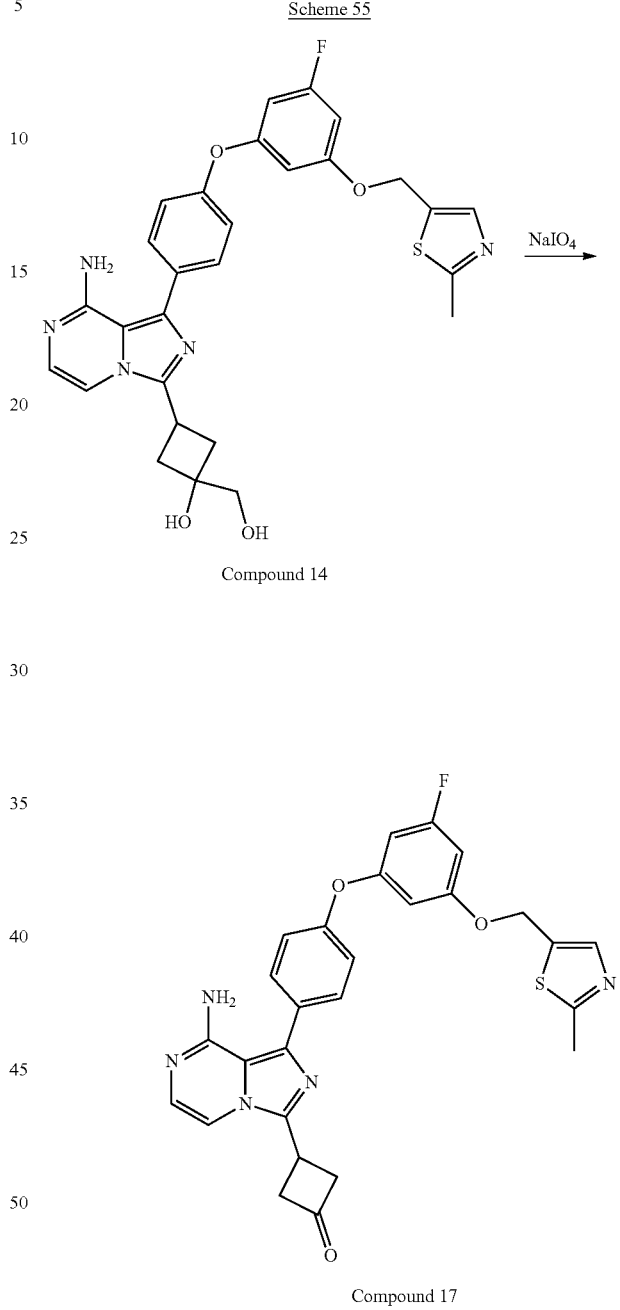

To a solution of Compound 14 (94 mg, 0.2 mmol) in THF (2.1 ml) and water (715 μl) cooled to 0° C. was added sodium periodate (44 mg, 0.2 mmol), and the reaction was slowly warmed to room temperature over a period of 2 hours. Water and ethyl acetate were added, the organic layer was separated, the aqueous phase was extracted twice with ethyl acetate, the combined organic extracts were washed with brine, dried over anhydrous MgSO$_4$, filtered and concentrated under reduced pressure. Purification by silica gel chromatography provided Compound 17 as a white foam. MS (m/z) M+H=516.2

Synthesis of Compound 20

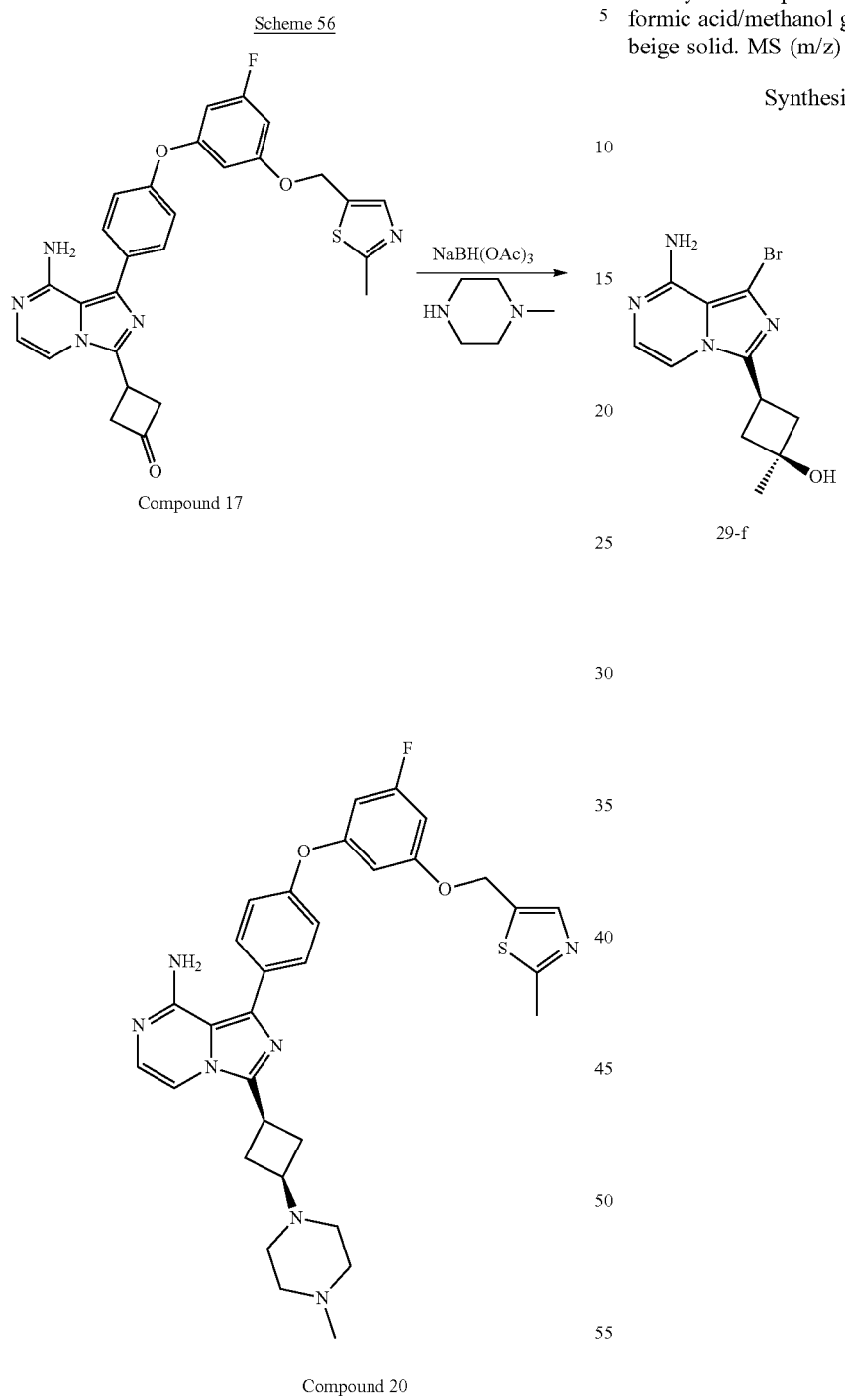

Scheme 56

Compound 17

Compound 20

Synthesis of Intermediate 57-a

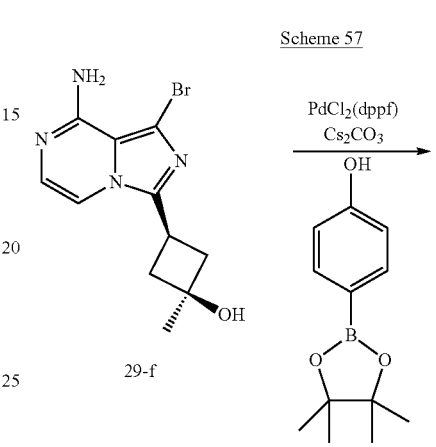

Scheme 57

29-f 57-a romethane were added to the residue, the organic layer was separated, washed with brine, dried over anhydrous $MgSO_4$, filtered and concentrated under reduced pressure. Purification by reverse phase chromatography eluting with a 0.1% formic acid/methanol gradient provided Compound 20 as a beige solid. MS (m/z) M+H=600.0

To a solution of Compound 17 (55 mg, 0.1 mmol) in THF (2.7 ml) were sequentially added 1-methylpiperazine (14 μl, 0.1 mmol) and sodium triacetoxyborohydride (50 mg, 0.2 mmol), and the reaction was stirred for 3 hours at room temperature. Volatiles were removed under reduced pressure. A saturated aqueous solution of $NaHCO_3$ and dichlo- To a solution of Intermediate 29-f (500 mg, 1.7 mmol) in 1,2-dimethoxyethane (10.3 ml) and water (2.6 ml) were sequentially added potassium carbonate (721 mg, 5.2 mmol), 4-(4,4,5,5-tetramethyl-1,3,2-dioxaborolan-2-yl)phenol (426 mg, 1.9 mmol) and Pd(dppf) (62 mg, 0.08 mmol)

under an atmosphere of nitrogen. The reaction mixture was stirred at 90° C. for 3 days and then cooled to room temperature. Volatiles were removed under reduced pressure. Purification by silica gel chromatography provided Intermediate 57-a as a beige solid.

Synthesis of Compound 25

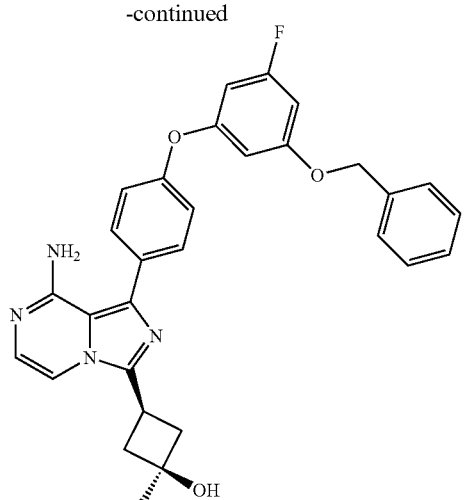

Compound 25

A solution of Intermediate 57-a (200 mg, 0.6 mmol), 1-(benzyloxy)-3-bromo-5-fluorobenzene (217 mg, 0.8 mmol), N,N-Dimethylglycine (199 mg, 1.9 mmol), cesium carbonate (840 mg, 2.6 mmol), and copper(I) iodide (123 mg, 0.6 mmol) in 1,4-dioxane (0.6 ml) was heated in a pressure vessel at 110° C. for 2 days, then cooled to room temperature. Ethyl acetate was added, the reaction was adsorbed on silica gel. Purification silica gel chromatography provided Compound 25 as a yellow solid. MS (m/z) M+H=511.1

Synthesis of Intermediate 59-h

Scheme 58

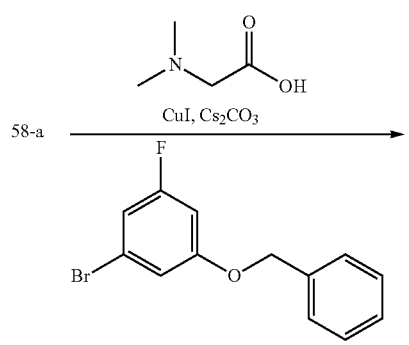

Scheme 59

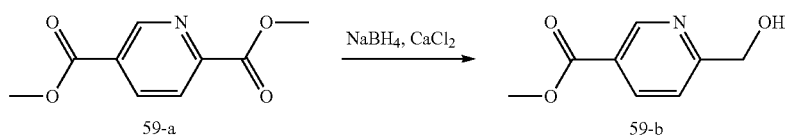

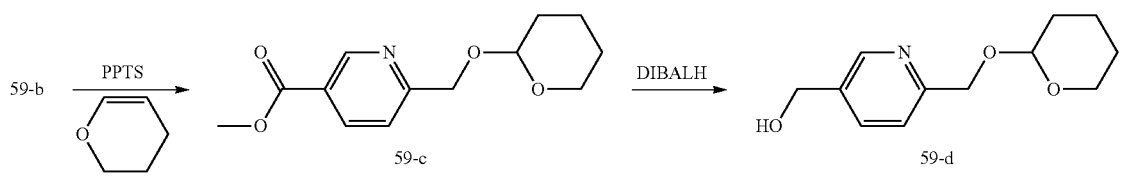

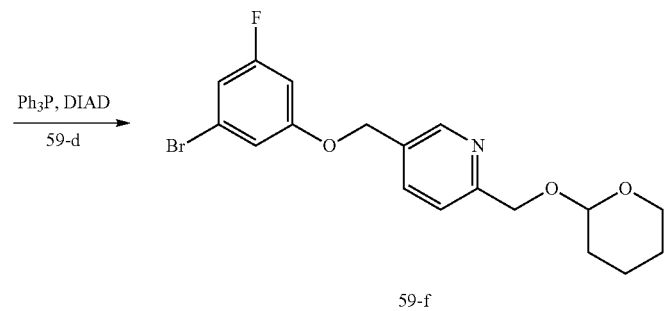

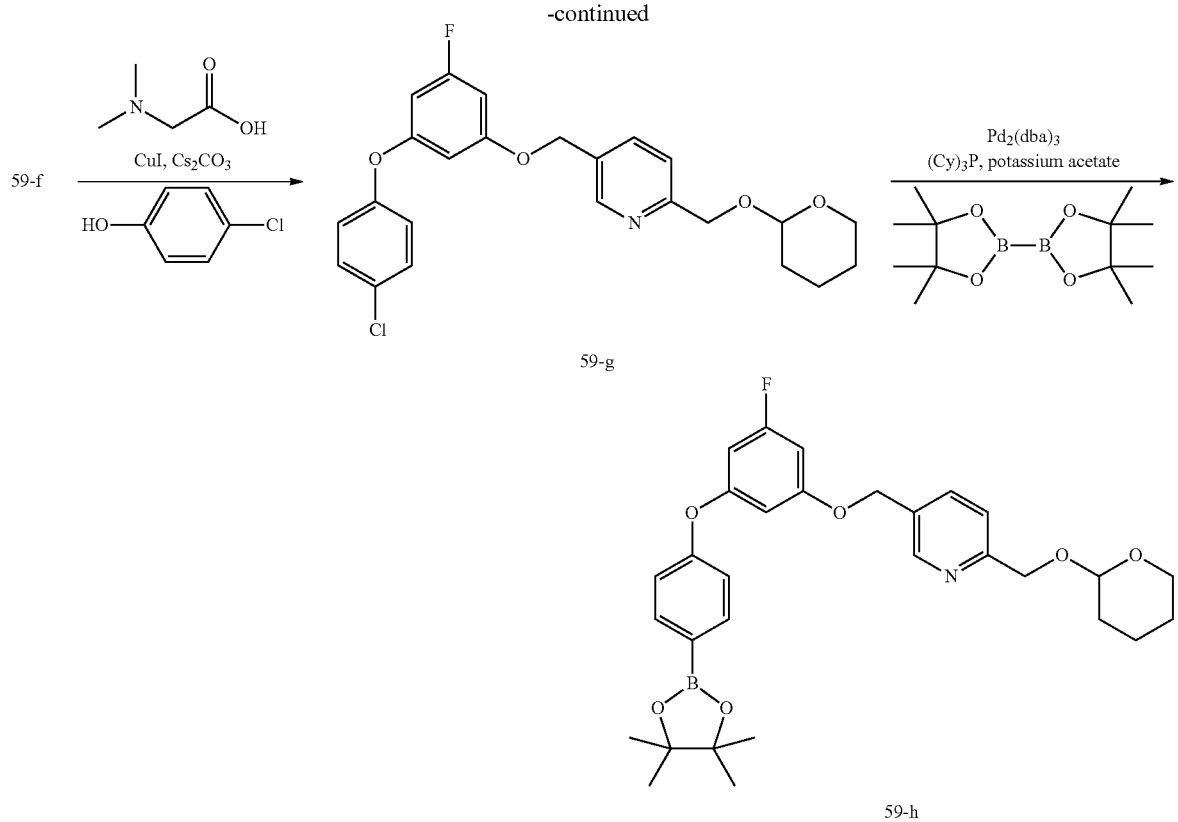

Step 1: Intermediate 59-b

To a solution of dimethyl pyridine-2,5-dicarboxylate 59-a (13.0 g, 66.6 mmol) in a mixture of THF (110 mL) and ethanol (110 mL) was added calcium chloride (29.6 g, 266 mmol). After stirring at room temperature for 30 minutes, the reaction was cooled to 0° C., and sodium borohydride (3.78 g, 100 mmol) was added portion wise. After the addition was completed the reaction was stirred at room temperature overnight. A saturated aqueous solution of ammonium chloride and dichloromethane were added, the organic layer was separated and the aqueous phase was extracted twice with dichloromethane. The combined organic extracts were washed with brine, dried over $MgSO_4$, filtered and concentrated under reduced pressure to provide Intermediate 59-b as a yellow solid.

Step 2: Intermediate 59-c

To a solution of Intermediate 59-b (1.70 g, 10.17 mmol) in dichloromethane (203 mL) was added 3,4-dihydro-2H-pyran (4.28 g, 50.8 mmol), and PPTS (2.56 g, 10.17 mmol), and the reaction was stirred at room temperature overnight. Water was added and the organic layer was separated, washed with brine, dried over $MgSO_4$, filtered and concentrated under reduced pressure to provide Intermediate 59-c as a white solid.

Step 3: Intermediate 59-d

To a solution of Intermediate 59-c (2.56 g, 10.17 mmol) in THF (51 ml) cooled to 0° C. was added drop wise a 1.0 M solution of DIBALH in hexane (23.39 ml, 23.39 mmol), the reaction was then stirred at 0° C. for 1.5 hour and room temperature overnight. Water (1.0 ml) was slowly added, followed 15% NaOH (3.5 ml), and water (2.3 ml), and the mixture was stirred at room temperature for 30 minutes. The reaction was filtered over celite and volatiles were removed under reduced pressure. Purification by silica gel chromatography provided Intermediate 59-d as a yellow oil.

Step 4: Intermediate 59-f

To a solution of Intermediate 3-bromo-5-fluorophenol 59-e (2.5 g, 13.2 mmol) and Intermediate 59-d (3.2 g, 14.5 mmol) in THF (13.2 ml), were sequentially added triphenylphosphine (5.2 g, 19.7 mmol), and DIAD (4.26 g, 21.1 mmol) at room temperature, and the reaction was then stirred overnight. Volatiles were removed under reduced pressure. Purification by silica gel chromatography provided Intermediate 59-f as a yellow oil.

Step 5: Intermediate 59-g

A solution of Intermediate 59-f (2.0 g, 5.0 mmol), 4-chlorophenol (681 mg, 5.3 mmol), N,N-dimethylglycine (1.5 g, 15.1 mmol), cesium carbonate (8.2 g, 25.2 mmol) and copper (I) iodide (961 mg, 5.0 mmol) in 1,4-dioxane (14.4 ml), was heated in a pressure vessel at 110° C. for 2 days, and then cooled to room temperature. Ethyl acetate was added, the reaction was adsorbed on silica gel. Purification by silica gel chromatography provided Intermediate 59-g as a colorless oil.

Step 6: Intermediate 59-h

To a degassed solution of Intermediate 59-g (1.1 g, 2.5 mmol), 4,4,4',4',5,5,5',5'-octamethyl-2,2'-bi(1,3,2-dioxaborolane (755 mg, 3.0 mmol), potassium acetate (730 mg, 7.4 mmol) and tricyclohexylphosphine (139 mg, 0.5 mmol) was added $Pd_2(dba)_3$ (227 mg, 0.2 mmol) under nitrogen. The reaction was heated in a pressure vessel at 110° C. for 2 days, and then cooled to room temperature. Ethyl acetate was added, the reaction was filtered over celite and the filtrate was reduced under reduced pressure. Purification by silica gel chromatography provided Intermediate 59-h as a colorless oil.

Synthesis of Compound 35

Scheme 60

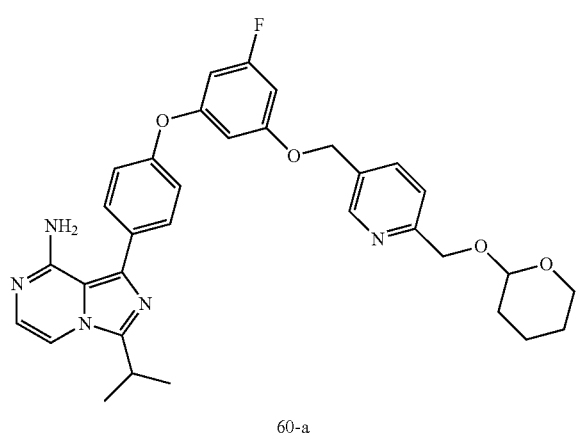

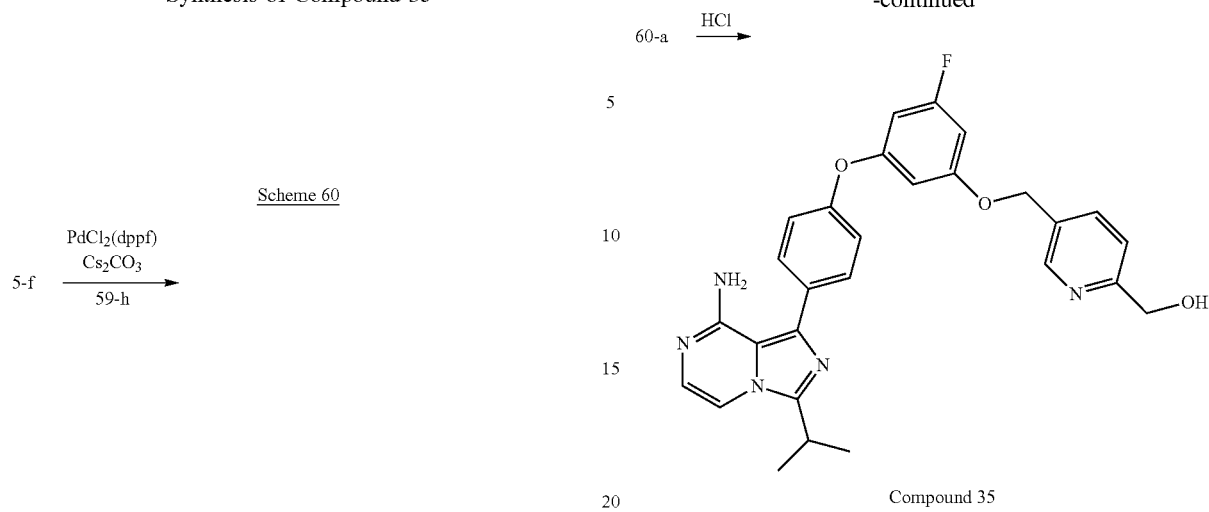

Compound 35

Step 1: Intermediate 60-a

To a degassed solution of Intermediate 5-f (250 mg, 1.0 mmol), Intermediate 59-h (525 mg, 1.0 mmol) and cesium carbonate (958 mg, 2.9 mmol) in DME (5.2 ml), and water (1.3 ml), was added PdCl$_2$(dppf) (72 mg, 0.10 mmol), and the reaction was heated in a pressure vessel at 100° C. overnight, and then cooled to room temperature. Ethyl acetate was added, the reaction was filtered over celite. The filtrate was concentrated under reduced pressure. Purification by silica gel chromatography provided Intermediate 60-a as a beige foam.

Step 2: Compound 35

To a solution of Intermediate 60-a (65 mg, 0.1 mmol) in MeOH (4.4 ml) was added 3N HCl (2.60 ml, 7.80 mmol) and the reaction was stirred at room temperature for 1 hour. Volatiles were removed under reduced pressure. Ethyl acetate was added, a precipitate formed and was collected by filtration to provide Compound 35·2HCl as a beige solid. MS (m/z) M+H=500.2.

TABLE 1

Example Compounds of Formula I

| Compound | Structure | MS (m/z) |
|---|---|---|
| 1 | 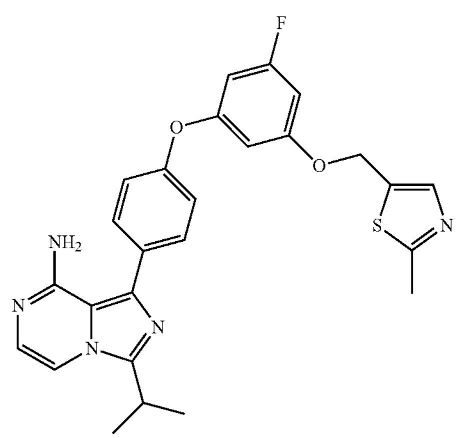 [SMILES: Cc1ncc(COc2cc(F)cc(Oc3ccc(-c4nc(C(C)C)n5ccnc(N)c45)cc3)c2)s1] | [M + H]$^+$ = 490.3; |

TABLE 1-continued

Example Compounds of Formula I

| Compound | Structure | MS (m/z) |
|---|---|---|
| 2 | 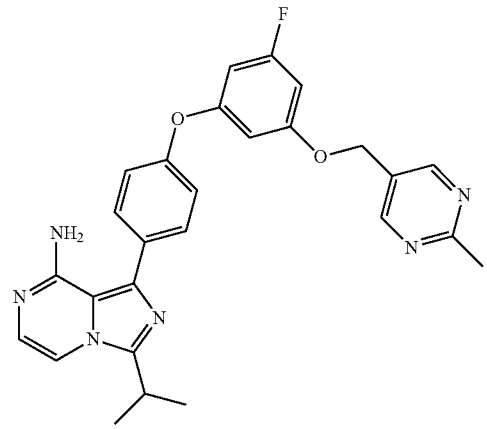 | [M + H]⁺ = 485.2; |
| 3 | 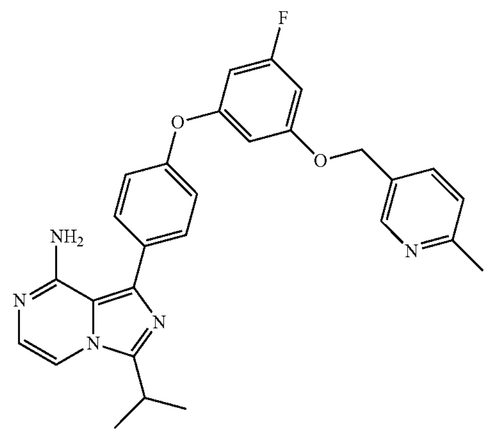 [SMILES: Cc1ccc(COc2cc(F)cc(Oc3ccc(-c4nc(C(C)C)n5ccnc(N)c45)cc3)c2)cn1] | [M + H]⁺ = 484.3; |
| 4 | 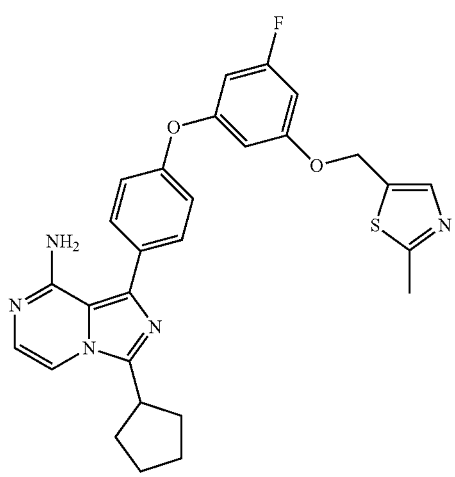 [SMILES: Cc1ncc(COc2cc(F)cc(Oc3ccc(-c4nc(C5CCCC5)n5ccnc(N)c45)cc3)c2)s1] | [M + H]⁺ = 516.1; |

TABLE 1-continued

Example Compounds of Formula I

| Compound | Structure | MS (m/z) |
|---|---|---|
| 5 | 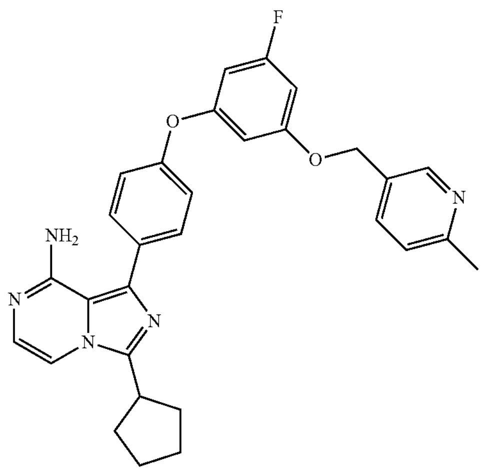 [SMILES: Cc1ccc(COc2cc(F)cc(Oc3ccc(-c4nc(C5CCCC5)n5ccnc(N)c45)cc3)c2)cn1] | [M + H]⁺ = 510.3; |
| 6 | 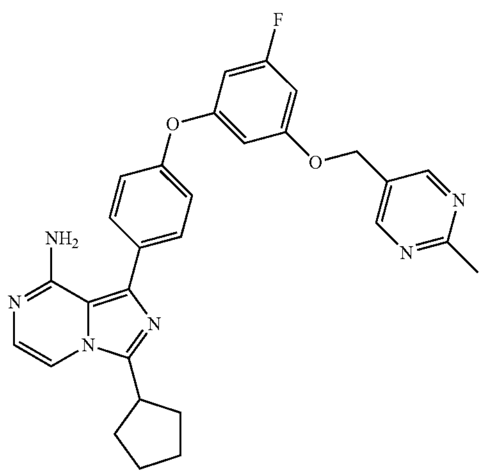 [SMILES: Cc1ncc(COc2cc(F)cc(Oc3ccc(-c4nc(C5CCCC5)n5ccnc(N)c45)cc3)c2)cn1] | [M + H]⁺ = 511.3; |
| 7 | 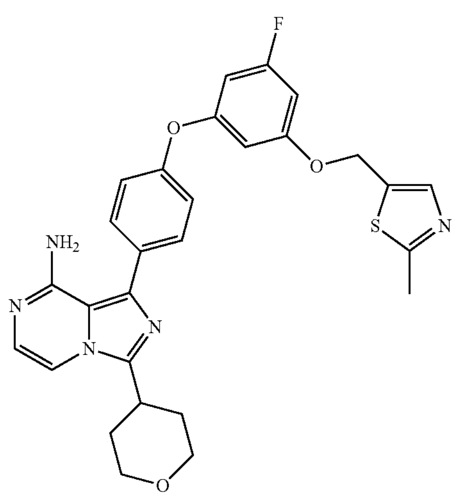 [SMILES: Cc1ncc(COc2cc(F)cc(Oc3ccc(-c4nc(C5CCOCC5)n5ccnc(N)c45)cc3)c2)s1] | [M + H]⁺ = 532.2; |

TABLE 1-continued

Example Compounds of Formula I

| Compound | Structure | MS (m/z) |
|---|---|---|
| 8 | 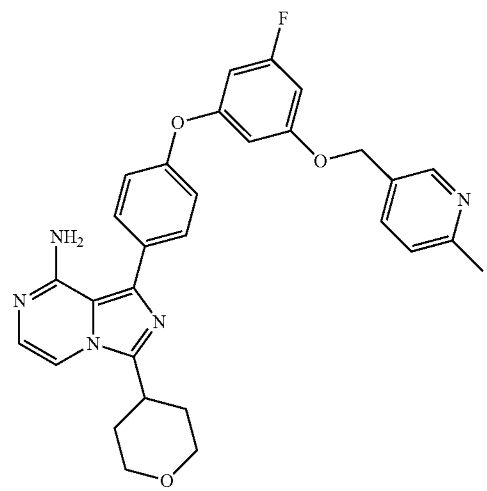 [SMILES: Cc1ccc(COc2cc(F)cc(Oc3ccc(-c4nc(C5CCOCC5)n5ccnc(N)c45)cc3)c2)cn1] | [M + H]+ = 526.2; |
| 9 | 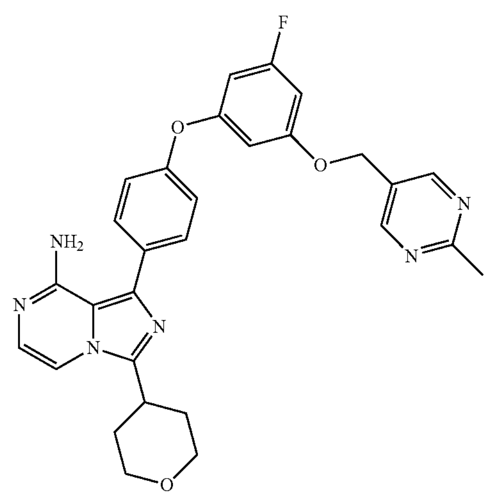 [SMILES: Cc1ncc(COc2cc(F)cc(Oc3ccc(-c4nc(C5CCOCC5)n5ccnc(N)c45)cc3)c2)cn1] | [M + H]+ = 527.3; |
| 10 | 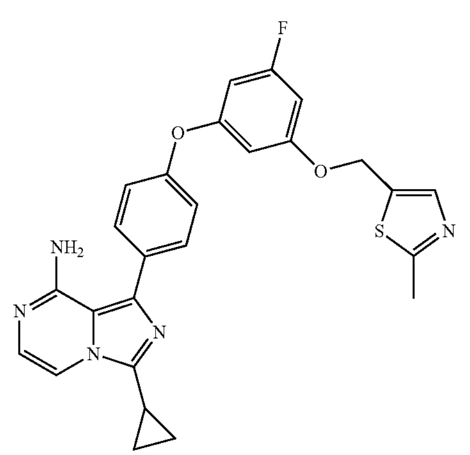 [SMILES: Cc1ncc(COc2cc(F)cc(Oc3ccc(-c4nc(C5CC5)n5ccnc(N)c45)cc3)c2)s1] | [M + H]+ = 488.2; |

TABLE 1-continued
Example Compounds of Formula I
| Compound | Structure | MS (m/z) |
|---|---|---|
| 11 | 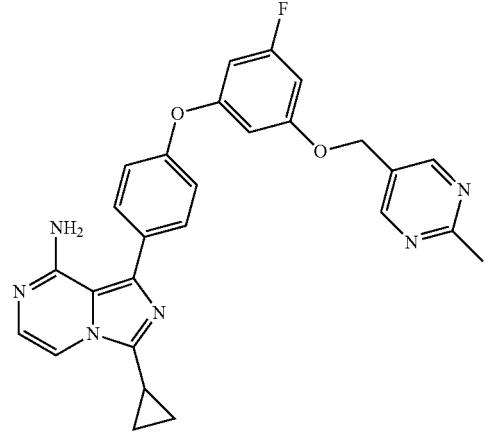 [SMILES: Cc1ncc(COc2cc(F)cc(Oc3ccc(-c4nc(C5CC5)n5ccnc(N)c45)cc3)c2)cn1] | [M + H]⁺ = 483.1; |
| 12 | 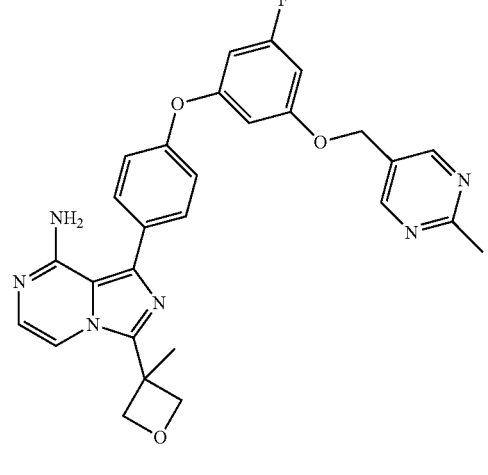 | [M + H]⁺ = 513.2; |
| 13 | 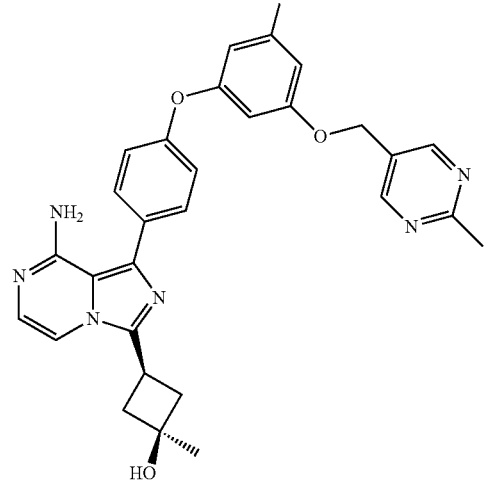 | [M + H]⁺ = 527.2; |

TABLE 1-continued

Example Compounds of Formula I

| Compound | Structure | MS (m/z) |
| --- | --- | --- |
| 14 | 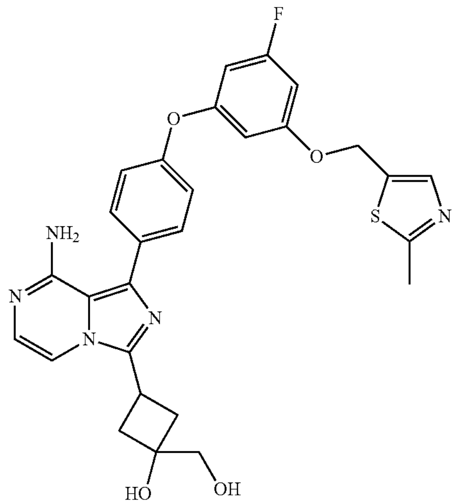 [SMILES: Cc1ncc(COc2cc(F)cc(Oc3ccc(-c4nc(C5CC(O)(CO)C5)n5ccnc(N)c45)cc3)c2)s1] | [M + H]⁺ = 548.1; |
| 15 | 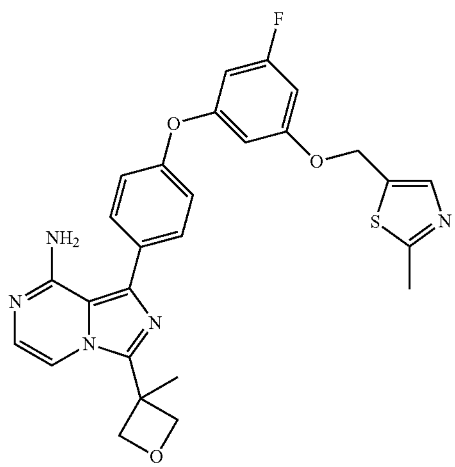 [SMILES: Cc1ncc(COc2cc(F)cc(Oc3ccc(-c4nc(C5(C)COC5)n5ccnc(N)c45)cc3)c2)s1] | [M + H]⁺ = 518.2; |
| 16 | 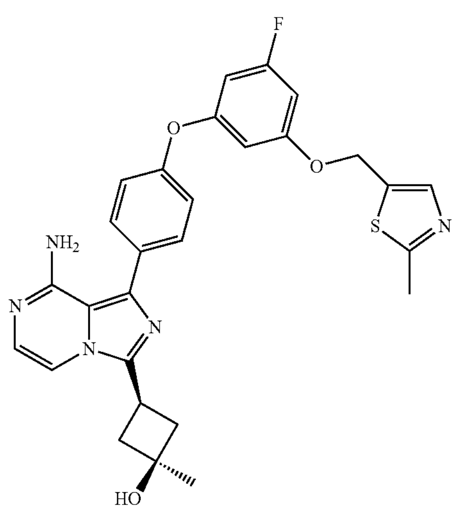 [SMILES: Cc1ncc(COc2cc(F)cc(Oc3ccc(-c4nc([C@H]5C[C@@](C)(O)C5)n5ccnc(N)c45)cc3)c2)s1] | [M + H]⁺ = 532.2; |

TABLE 1-continued

Example Compounds of Formula I

| Compound | Structure | MS (m/z) |
|---|---|---|
| 17 | 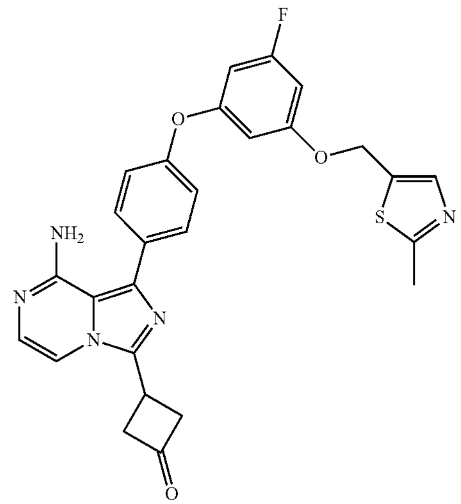 [SMILES: Cc1ncc(COc2cc(F)cc(Oc3ccc(-c4nc(C5CC(=O)C5)n5ccnc(N)c45)cc3)c2)s1] | [M + H]⁺ = 516.2; |
| 18 | 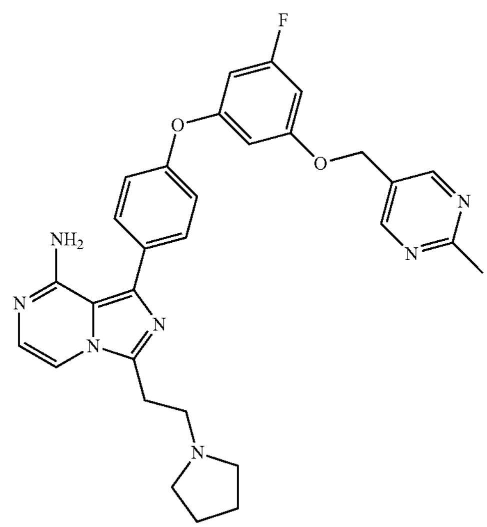 [SMILES: Cc1ncc(COc2cc(F)cc(Oc3ccc(-c4nc(CCN5CCCC5)n5ccnc(N)c45)cc3)c2)cn1] | [M + H]⁺ = 540.2; |
| 19 | 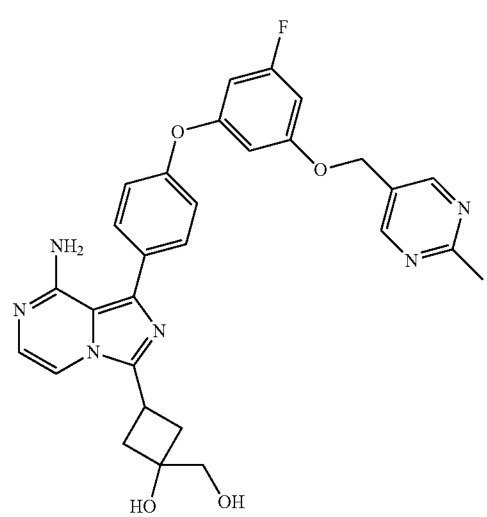 [SMILES: Cc1ncc(COc2cc(F)cc(Oc3ccc(-c4nc(C5CC(O)(CO)C5)n5ccnc(N)c45)cc3)c2)cn1] | [M + H]⁺ = 543.1; |

TABLE 1-continued
Example Compounds of Formula I
| Compound | Structure | MS (m/z) |
|---|---|---|
| 20 | 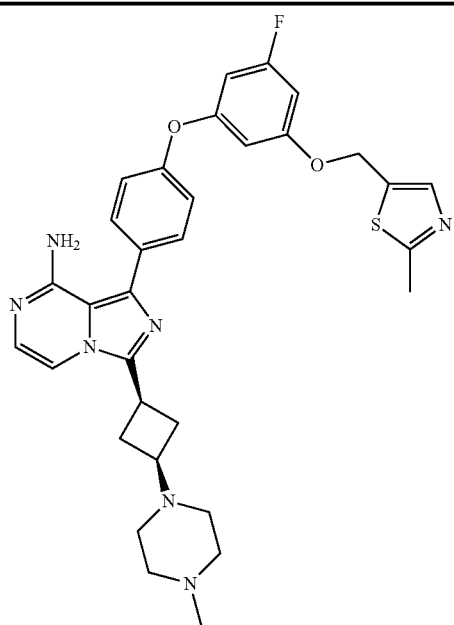 | [M + H]⁺ = 600.0; |
| 21 | 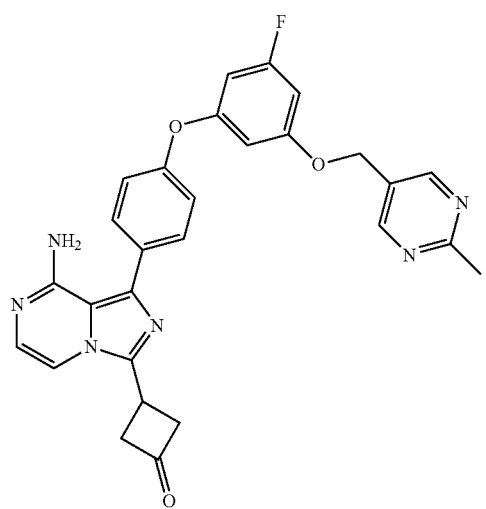 [SMILES: Cc1ncc(COc2cc(F)cc(Oc3ccc(-c4nc(C5CC(=O)C5)n5ccnc(N)c45)cc3)c2)cn1] | [M + H]⁺ = 511.1; |

TABLE 1-continued

Example Compounds of Formula I

| Compound | Structure | MS (m/z) |
|---|---|---|
| 22 | 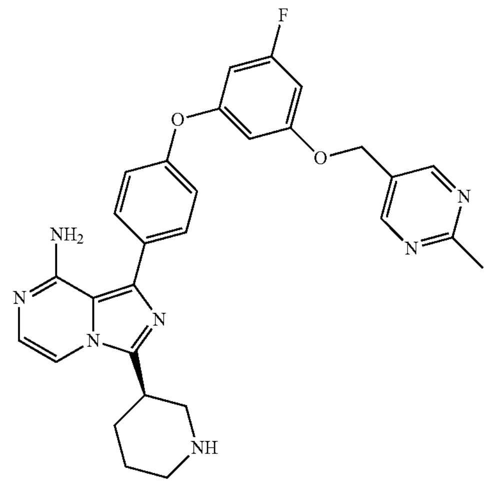 [SMILES: Cc1ncc(COc2cc(F)cc(Oc3ccc(-c4nc([C@@H]5CCCNC5)n5ccnc(N)c45)cc3)c2)cn1] | [M + H]⁺ = 526.1; |
| 23 | 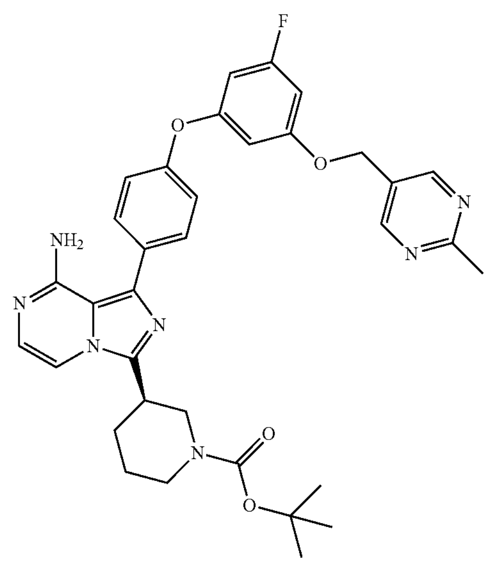 [SMILES: Cc1ncc(COc2cc(F)cc(Oc3ccc(-c4nc([C@@H]5CCCN(C(=O)OC(C)(C)C)C5)n5ccnc(N)c45)cc3)c2)cn1] | [M + H]⁺ = 626.1; |
| 24 | 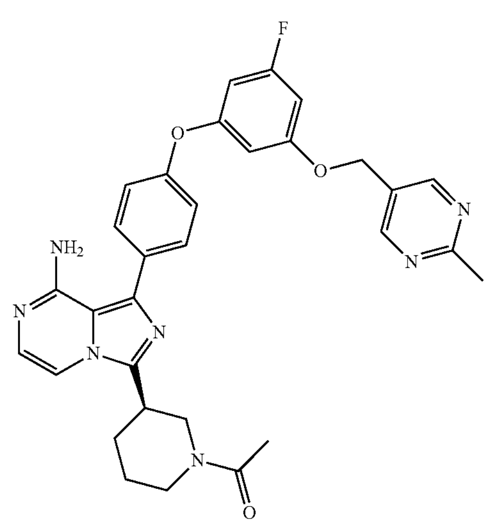 [SMILES: CC(=O)N1CCC[C@@H](c2nc(-c3ccc(Oc4cc(F)cc(OCc5cnc(C)nc5)c4)cc3)c3c(N)nccn23)C1] | [M + H]⁺ = 568.0; |

TABLE 1-continued
Example Compounds of Formula I
| Compound | Structure | MS (m/z) |
|---|---|---|
| 25 | 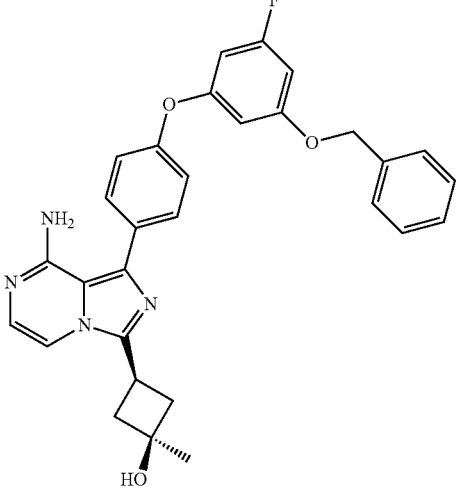 | [M + H]+ = 511.1; |
| 26 | 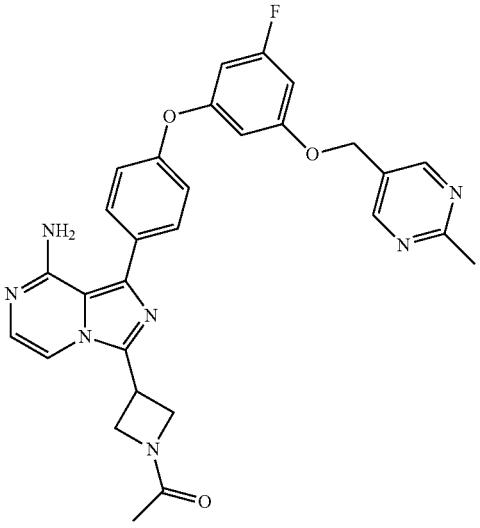 [SMILES: CC(=O)N1CC(c2nc(-c3ccc(Oc4cc(F)cc(OCc5cnc(C)nc5)c4)cc3)c3c(N)nccn23)C1] | [M + H]+ = 540.0; |
| 27 | 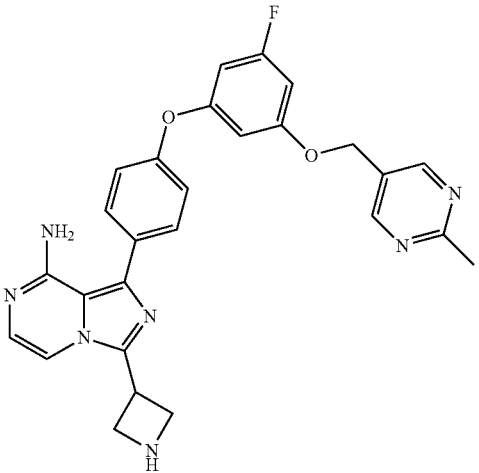 [SMILES: Cc1ncc(COc2cc(F)cc(Oc3ccc(-c4nc(C5CNC5)n5ccnc(N)c45)cc3)c2)cn1] | [M + H]+ = 498.1; |

TABLE 1-continued
Example Compounds of Formula I
| Compound | Structure | MS (m/z) |
|---|---|---|
| 28 | 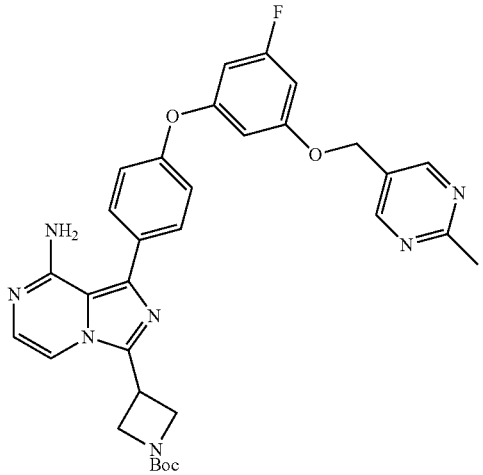 [SMILES: Cc1ncc(COc2cc(F)cc(Oc3ccc(-c4nc(C5CN(C(=O)OC(C)(C)C)C5)n5ccnc(N)c45)cc3)c2)cn1] | [M + H]⁺ = 598.0; |
| 29 | 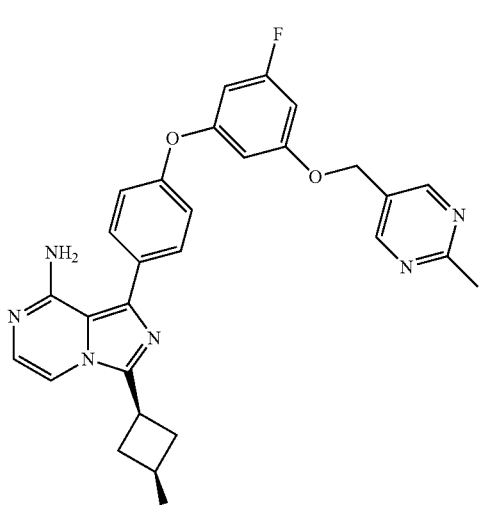 | [M + H]⁺ = 513.2; |
| 30 | 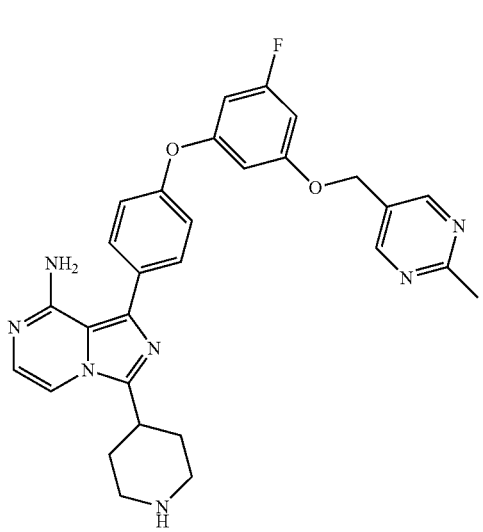 [SMILES: Cc1ncc(COc2cc(F)cc(Oc3ccc(-c4nc(C5CCNCC5)n5ccnc(N)c45)cc3)c2)cn1] | [M + H]⁺ = 526.1; |

TABLE 1-continued
Example Compounds of Formula I
| Compound | Structure | MS (m/z) |
|---|---|---|
| 31 | 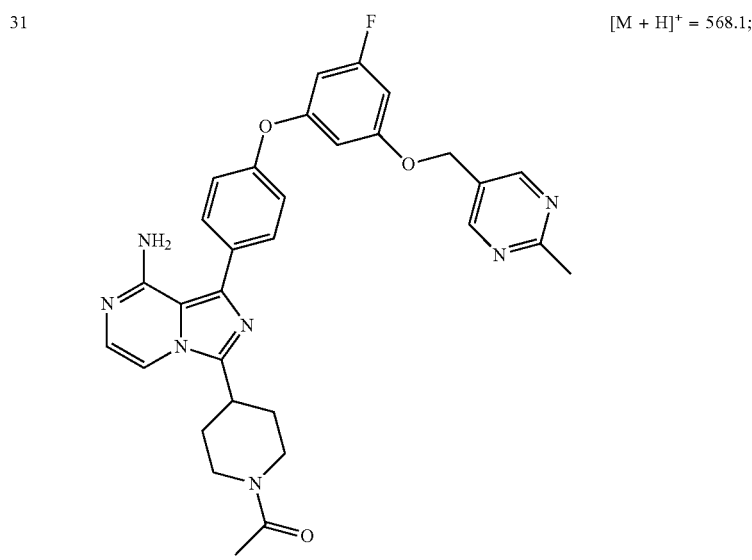 | [M + H]⁺ = 568.1; |
| 32 | 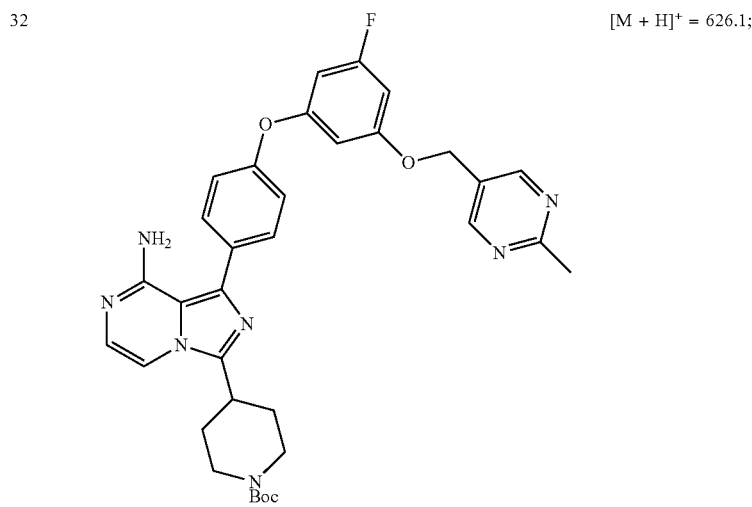 | [M + H]⁺ = 626.1; |

TABLE 1-continued

Example Compounds of Formula I

| Compound | Structure | MS (m/z) |
|---|---|---|
| 33 | 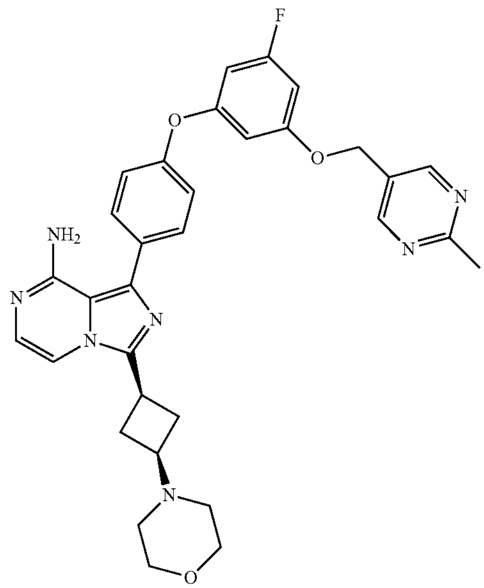 [SMILES: Cc1ncc(COc2cc(F)cc(Oc3ccc(-c4nc([C@H]5C[C@@H](N6CCOCC6)C5)n5ccnc(N)c45)cc3)c2)cn1] | [M + H]⁺ = 582.1; |
| 34 | 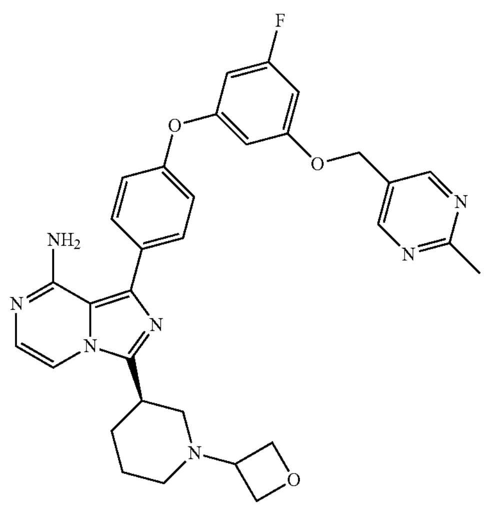 [SMILES: Cc1ncc(COc2cc(F)cc(Oc3ccc(-c4nc([C@@H]5CCCN(C6COC6)C5)n5ccnc(N)c45)cc3)c2)cn1] | [M + H]⁺ = 582.2; |
| 35 | 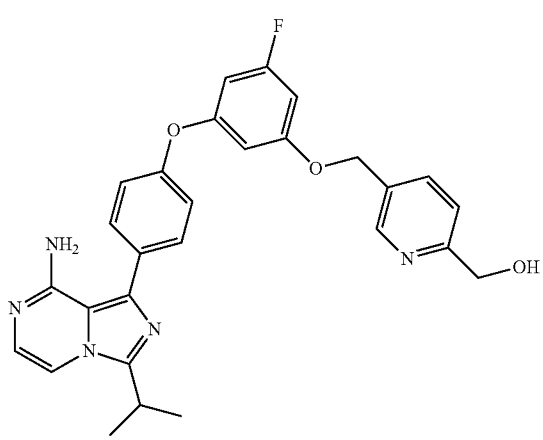 [SMILES: CC(C)c1nc(-c2ccc(Oc3cc(F)cc(OCc4ccc(CO)nc4)c3)cc2)c2c(N)nccn12] | [M + H]⁺ = 500.2. |

Biological Assays

Assays for determining kinase activity are described in more detail in the accompanying examples.

Kinase Inhibition

Btk Kinase Inhibition Assays

Method A:

Fluorescence polarization-based kinase assays were performed in 384 well-plate format using histidine tagged recombinant human full-length Bruton Agammaglobulinemia Tyrosine Kinase (Btk) and a modified protocol of the KinEASE™ FP Fluorescein Green Assay supplied from Millipore®. Kinase reaction were performed at room temperature for 60 minutes in presence of 250 μM substrate, 10 μM ATP and variable test article concentrations. The reaction was stopped with EDTA/kinase detection reagents. Phosphorylation of the substrate peptide was detected by fluorescence polarization measured with a Tecan 500 instrument. From the dose-response curve obtained, the $IC_{50}$ was calculated using Graph Pad Prisms® using a non linear fit curve. The Km for ATP on each enzyme was experimentally determined and the Ki values calculated using the Cheng-Prusoff equation (see: Cheng Y, Prusoff W. H. (1973) Relationship between the inhibition constant (K1) and the concentration of inhibitor which causes 50% inhibition ($I_{50}$) of an enzymatic reaction". Biochem. Pharmacol. 22 (23): 3099-108). $k_i$ values are reported in Tables 2a and 2b:

TABLE 2a

Inhibition of Btk

| Compound | $k_i$ (nM) |
|---|---|
| 1 | a |
| 2 | a |
| 3 | a |
| 4 | a |
| 5 | a |
| 6 | a |
| 7 | a |
| 8 | a |
| 9 | a |
| 10 | a |
| 11 | a |
| 12 | a |
| 13 | a |
| 14 | a |
| 15 | a |
| 16 | a |
| 17 | a |
| 18 | a |
| 19 | a |
| 20 | a |
| 21 | a |
| 22 | a |
| 24 | a |
| 25 | a |
| 26 | a |
| 27 | a | a - Ki < 100 nM;
b - 100 nM < Ki < 1000 nM,
c - ki > 1000 nM.

Method B:

In vitro potency of selected compound was defined against human BTK kinase (hBTK) using KinaseProfiler radiometric protein kinase assays performed at Eurofins Pharma Discovery Services UK Limited.

hBTK kinase is diluted in buffer and all compounds were prepared to 50× final assay concentration in 100% DMSO. This working stock of the compound was added to the assay well as the first component in the reaction, followed by the remaining components as detailed in the assay protocol listed above. The reaction was initiated by the addition of the MgATP mix. The kinase reaction was performed at room temperature for 40 minutes in presence of 250 μM substrate, 10 mM MgAcetate, [γ-33P-ATP] (specific activity approx. 500 cpm/pmol, concentration as required) and variable test article concentrations. The ATP concentrations in the assays were with 15 μM of the apparent. The reaction was stopped by the addition of 3% phosphoric acid solution. 10 μL of the reaction is then spotted onto a P30 filtermat and washed three times for 5 minutes in 75 mM phosphoric acid and once in methanol prior to drying and scintillation counting. In addition positive control wells contain all components of the reaction, except the compound of interest; however, DMSO (at a final concentration of 2%) were included in these wells to control for solvent effects as well as blank wells contain all components of the reaction, with a reference inhibitor replacing the compound of interest. This abolishes kinase activity and establishes the base-line (0% kinase activity remaining). The potency of each compound was reported by estimating the $EC_{50}$.

TABLE 2b

Inhibition of Btk

| Compound | $EC_{50}$ (nM) |
|---|---|
| 29 | a |
| 30 | a |
| 31 | a |
| 33 | a |
| 34 | a |
| 35 | a | a - $EC_{50}$ < 100 nM;
b - 100 nM < $EC_{50}$ < 1000 nM,
c - $EC_{50}$ > 1000 nM.

Cellular Assay

Splenic Cell Proliferation Assay

Proliferation of splenocytes in response to anti-IgM can be blocked by inhibition of Btk. Splenocytes were obtained from 6 week old male CD1 mice (Charles River Laboratories Inc.). Mouse spleens were manually disrupted in PBS and filtered using a 70 um cell strainer followed by ammonium chloride red blood cell lysis. Cells were washed, resuspended in Splenocyte Medium (HyClone RPMI supplemented with 10% heat-inactivated FBS, 0.5× non-essential amino acids, 10 mM HEPES, 50 uM beta mercaptoethanol) and incubated at 37° C., 5% $CO_2$ for 2 h to remove adherent cells. Suspension cells were seeded in 96 well plates at 50,000 cells per well and incubated at 37° C., 5% $CO_2$ for 1 h. Splenocytes were pre-treated in triplicate with 10,000 nM curves of Formula I compounds for 1 h, followed by stimulation of cell proliferation with 2.5 ug/ml anti-IgM F(ab')$_2$ (Jackson ImmunoResearch) for 72 h. Cell proliferation was measured by Cell Titer-Glo Luminescent Assay (Promega). $EC_{50}$ values (50% proliferation in the presence of compound as compared to vehicle treated controls) were calculated from dose response compound curves using GraphPad Prism Software.

$EC_{50}$ values are reported in Table 3:

TABLE 3

Inhibition of splenic cell proliferation

| Compound | $EC_{50}$ (nM) |
|---|---|
| 1 | a |
| 2 | a |
| 3 | a |

TABLE 3-continued

Inhibition of splenic cell proliferation

| Compound | EC$_{50}$ (nM) |
|---|---|
| 4 | a |
| 5 | a |
| 6 | a |
| 7 | a |
| 8 | a |
| 9 | a |
| 10 | a |
| 11 | a |
| 12 | a |
| 13 | a |
| 14 | a |
| 15 | a |
| 16 | a |
| 17 | a |
| 18 | b |
| 19 | a |
| 20 | a |
| 21 | a |
| 22 | a |
| 24 | a |
| 25 | a |
| 26 | a |
| 27 | b |
| 29 | a |
| 30 | a |
| 31 | a |
| 33 | a |
| 34 | a |
| 35 | a | a - EC$_{50}$ < 100 nM;
b - 100 nM < EC$_{50}$ < 1000 nM,
c - EC$_{50}$ > 1000 nM.

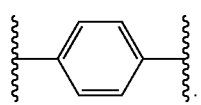

21. The compound according to claim 1, wherein W is selected from the group consisting of
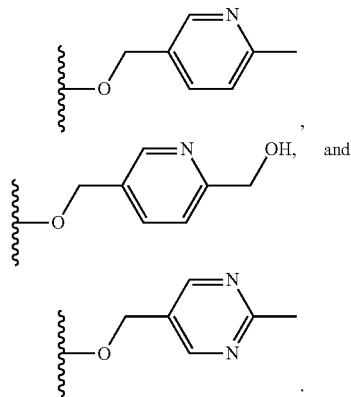

The invention claimed is:

1. A compound of Formula I:

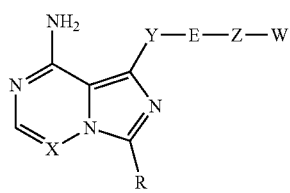

Formula I or pharmaceutically acceptable salt, solvate, solvate of salt, stereoisomer, tautomer, isotope, or complex thereof, wherein X is
1) CH;

R is
1) hydrogen,
2) alkyl,
3) heteroalkyl,
4) carbocyclyl,
5) heterocyclyl,
6) aryl, or
7) heteroaryl, wherein the alkyl, heteroalkyl, carbocyclyl, heterocyclyl, aryl, or heteroaryl are optionally substituted;

Y is

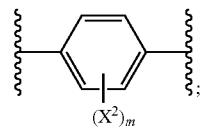

E is oxygen;

Z is

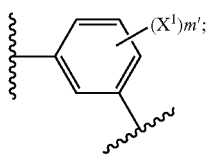

W is
1) —OCH$_2$R$^1$ or
2) —CH$_2$OR$^1$, wherein Y-E-Z-W is

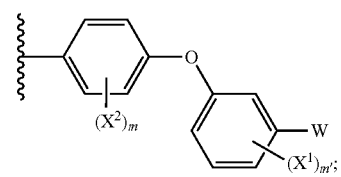

R$^1$ is substituted or unsubstituted 5-membered heteroaryl;

X$^1$ and X$^2$ are independently hydrogen or halogen;

m is an integer from 0 to 4;

m' is an integer from 0 to 4.

2. The compound according to claim 1, wherein R is selected from the group consisting of:

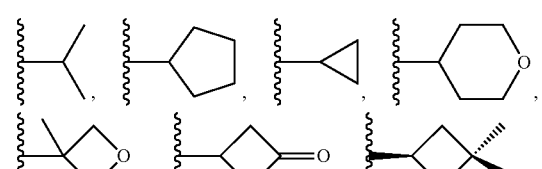

113
-continued

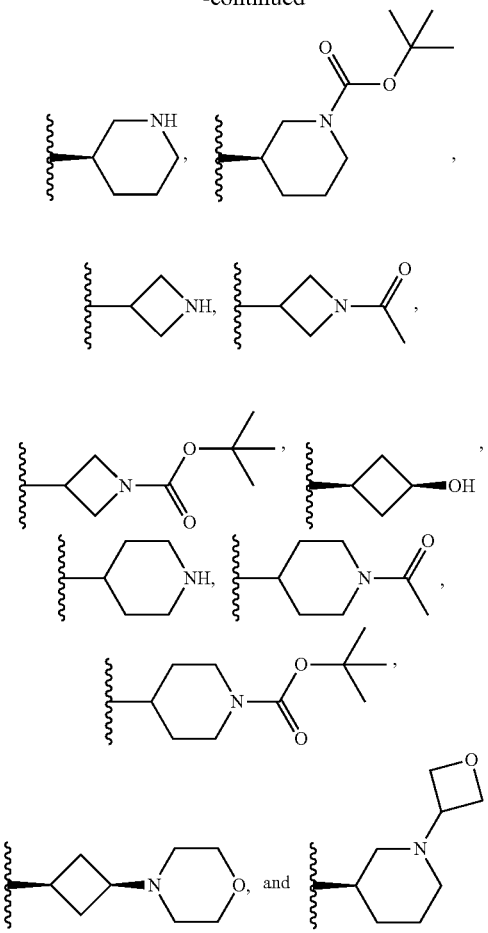

3. The compound according to claim 1, wherein Z is

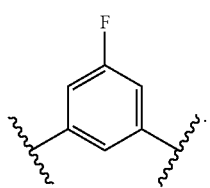 [SMILES: *c1cc(*)cc(F)c1]

4. The compound according to claim 1, wherein Y is

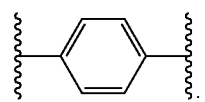

5. The compound according to claim 1, wherein W is

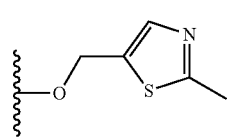

6. A compound of Formula II:

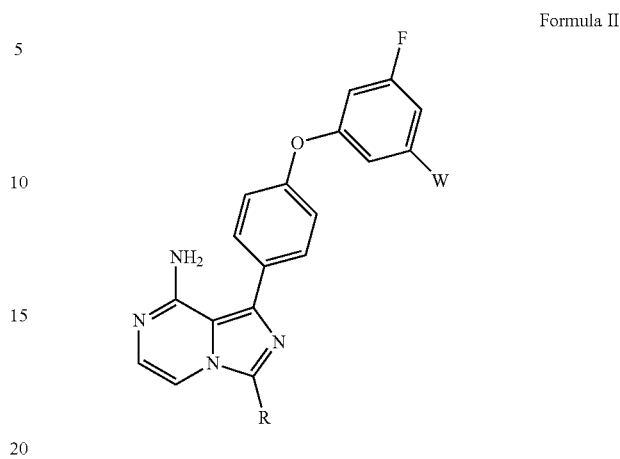

Formula II or a pharmaceutically acceptable salt, solvate, solvate of salt, stereoisomer, tautomer, isotope, or complex thereof wherein R is selected from the group consisting of:
1) hydrogen,
2) alkyl,
3) heteroalkyl,
4) carbocyclyl,
5) heterocyclyl,
6) aryl, or
7) heteroaryl, wherein the alkyl, heteroalkyl, carbocyclyl, heterocyclyl, aryl, or heteroaryl are optionally substituted;

wherein W is selected from the group consisting of:

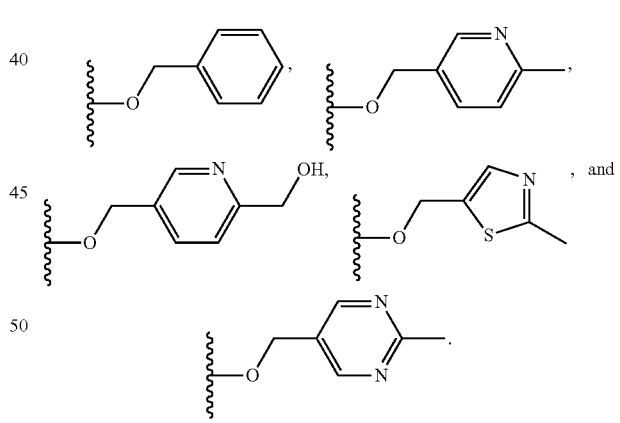

7. The compound according to claim 6, wherein R is selected from the group consisting of:

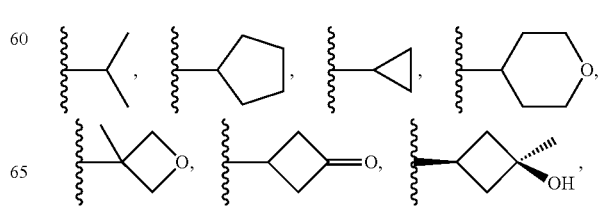

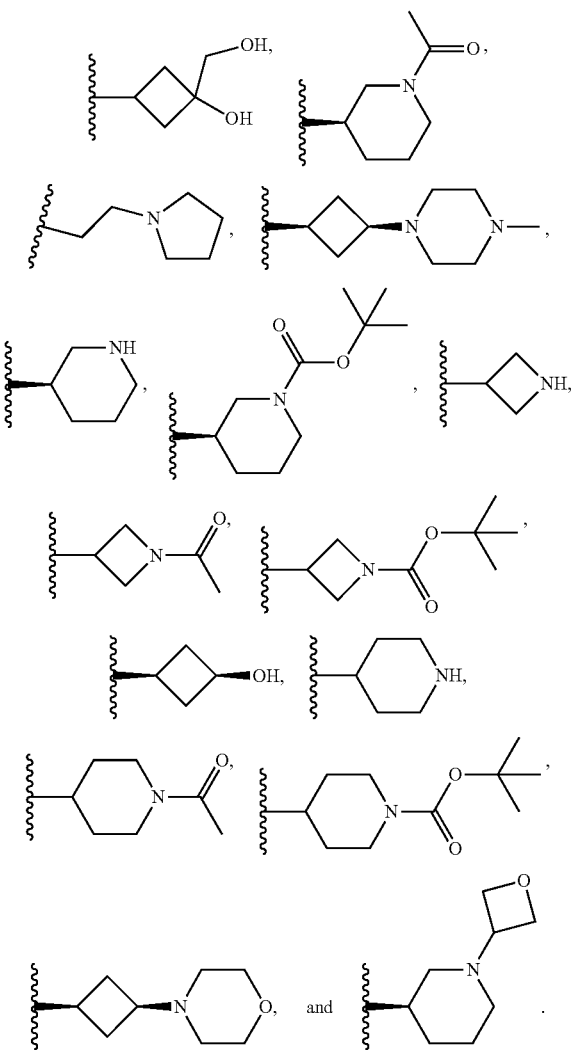
8. A compound selected from the group consisting of:
| Compound | Structure |
|---|---|
| 1 | 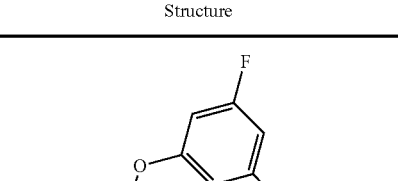 |
| 2 | 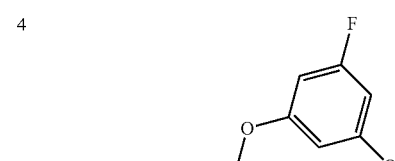 |
| 3 | 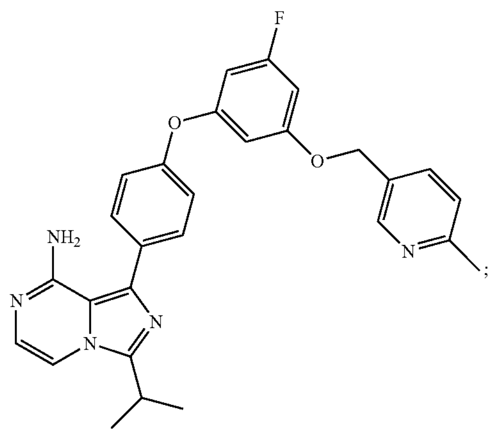 [SMILES: Cc1ccc(COc2cc(F)cc(Oc3ccc(-c4nc(C(C)C)n5ccnc(N)c45)cc3)c2)cn1] |
| 4 | 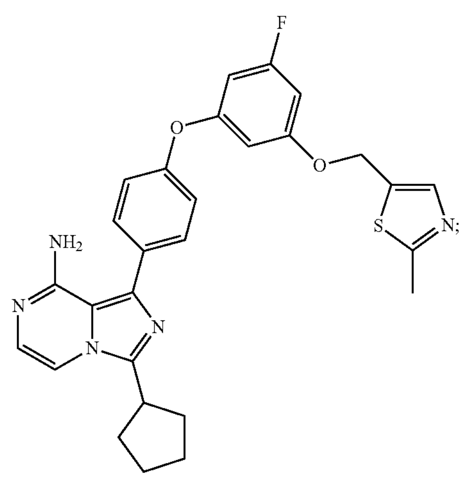 [SMILES: Cc1ncc(COc2cc(F)cc(Oc3ccc(-c4nc(C5CCCC5)n5ccnc(N)c45)cc3)c2)s1] |

| Compound | Structure |
|---|---|
| 5 | 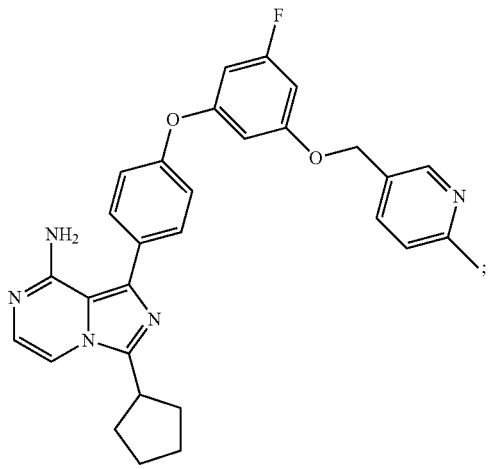 [SMILES: Cc1ccc(COc2cc(F)cc(Oc3ccc(-c4nc(C5CCCC5)n5ccnc(N)c45)cc3)c2)cn1] |
| 6 | 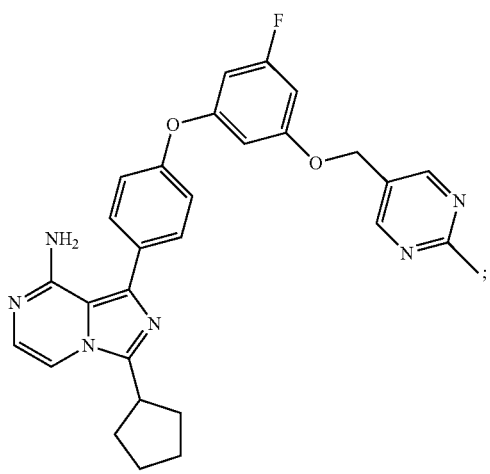 [SMILES: Cc1ncc(COc2cc(F)cc(Oc3ccc(-c4nc(C5CCCC5)n5ccnc(N)c45)cc3)c2)cn1] |
| 7 | 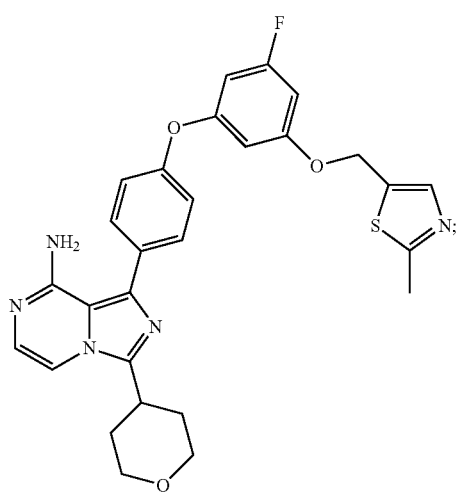 [SMILES: Cc1ncc(COc2cc(F)cc(Oc3ccc(-c4nc(C5CCOCC5)n5ccnc(N)c45)cc3)c2)s1] |
| Compound | Structure |
|---|---|
| 8 | 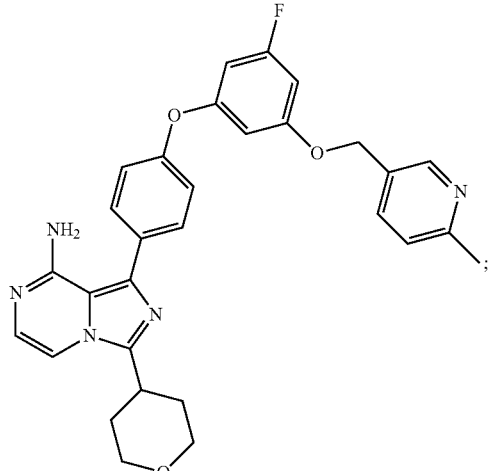 |
| 9 | 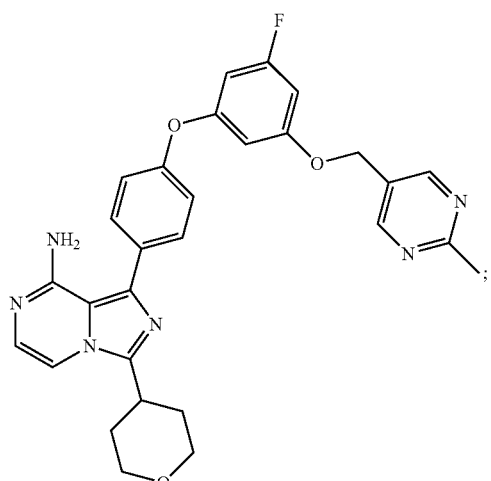 |
| 10 | 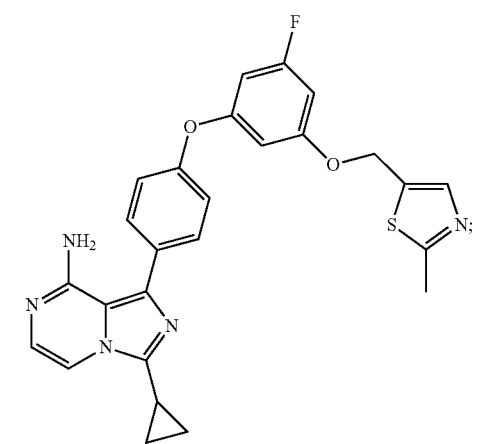 [SMILES: Cc1ncc(COc2cc(F)cc(Oc3ccc(-c4nc(C5CC5)n5ccnc(N)c45)cc3)c2)s1] |

| Compound | Structure |
|---|---|
| 11 | 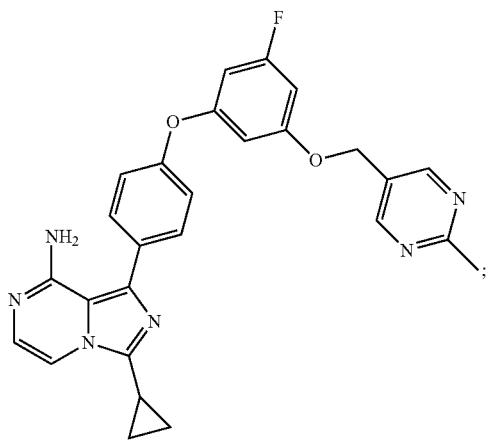 [SMILES: Cc1ncc(COc2cc(F)cc(Oc3ccc(-c4nc(C5CC5)n5ccnc(N)c45)cc3)c2)cn1] |
| 12 | 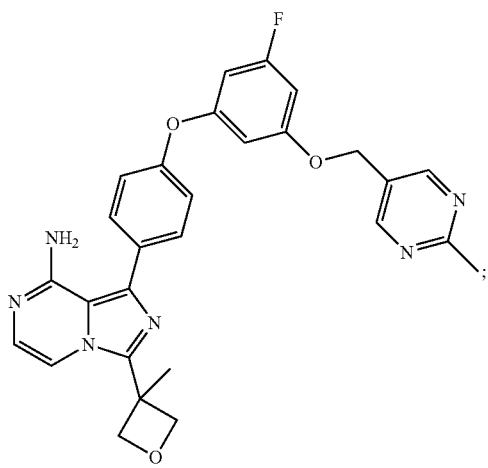 [SMILES: Cc1ncc(COc2cc(F)cc(Oc3ccc(-c4nc(C5(C)COC5)n5ccnc(N)c45)cc3)c2)cn1] |
| 13 | 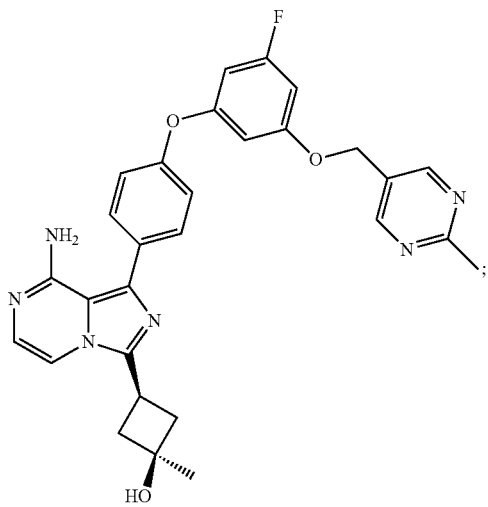 [SMILES: Cc1ncc(COc2cc(F)cc(Oc3ccc(-c4nc([C@H]5C[C@@](C)(O)C5)n5ccnc(N)c45)cc3)c2)cn1] |
| Compound | Structure |
|---|---|
| 14 | 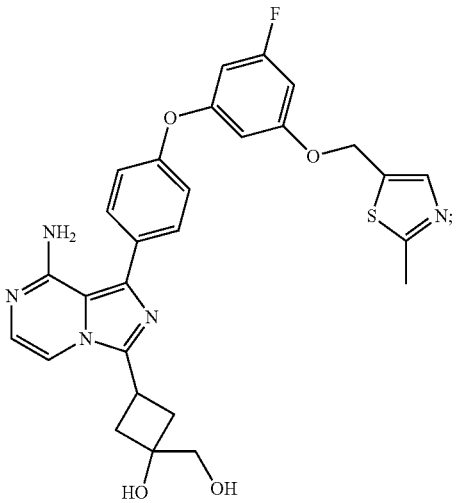 [SMILES: Cc1ncc(COc2cc(F)cc(Oc3ccc(-c4nc(C5CC(O)(CO)C5)n5ccnc(N)c45)cc3)c2)s1] |
| 15 | 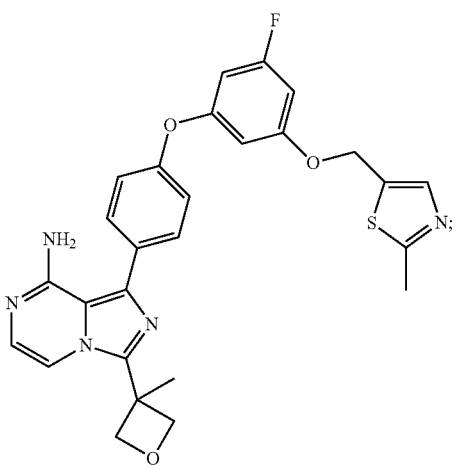 [SMILES: Cc1ncc(COc2cc(F)cc(Oc3ccc(-c4nc(C5(C)COC5)n5ccnc(N)c45)cc3)c2)s1] |
| 16 | 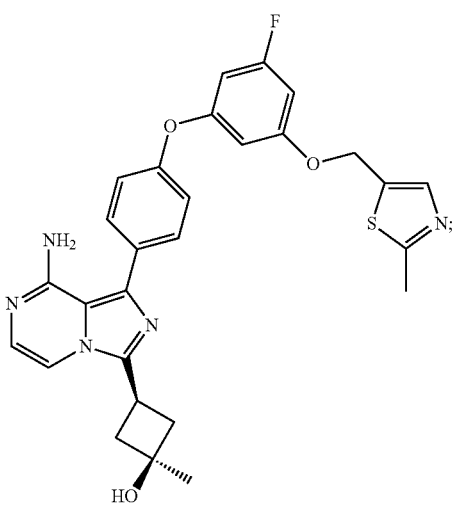 [SMILES: Cc1ncc(COc2cc(F)cc(Oc3ccc(-c4nc([C@H]5C[C@@](C)(O)C5)n5ccnc(N)c45)cc3)c2)s1] |

-continued
| Compound | Structure |
|---|---|
| 17 | 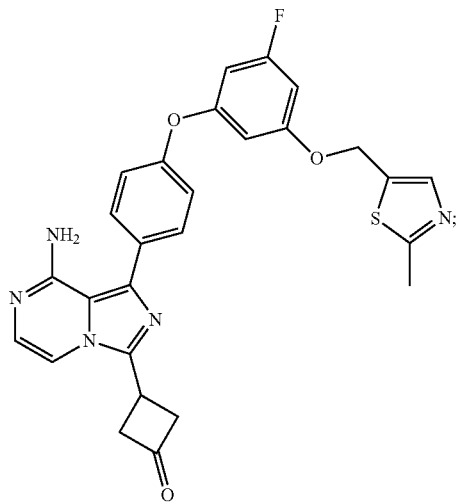 [SMILES: Cc1ncc(COc2cc(F)cc(Oc3ccc(-c4nc(C5CC(=O)C5)n5ccnc(N)c45)cc3)c2)s1] |
| 18 | 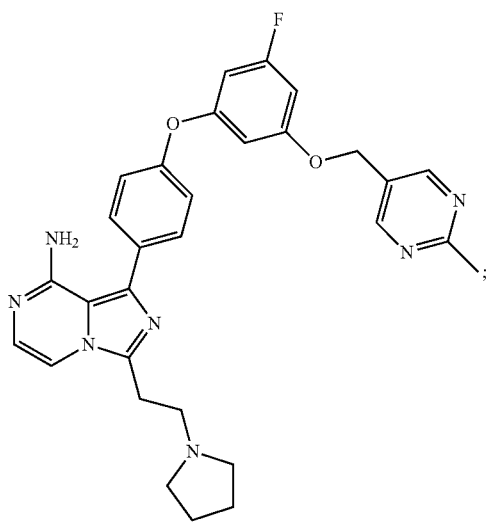 [SMILES: Cc1ncc(COc2cc(F)cc(Oc3ccc(-c4nc(CCN5CCCC5)n5ccnc(N)c45)cc3)c2)cn1] |
| 19 | 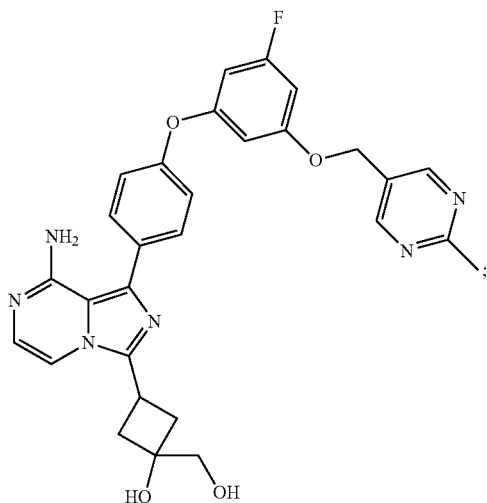 [SMILES: Cc1ncc(COc2cc(F)cc(Oc3ccc(-c4nc(C5CC(O)(CO)C5)n5ccnc(N)c45)cc3)c2)cn1] |
-continued
| Compound | Structure |
|---|---|
| 20 | 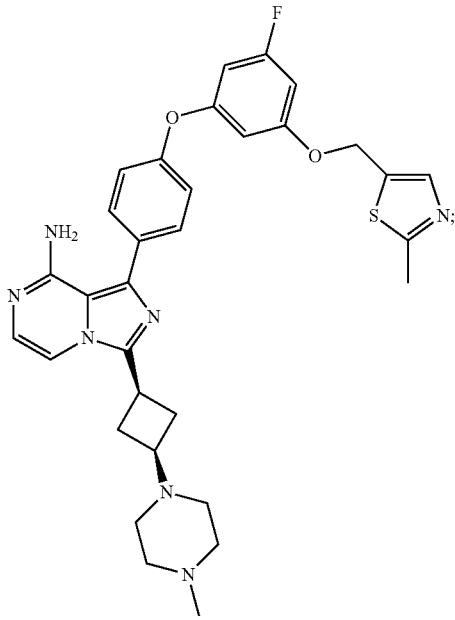 [SMILES: Cc1ncc(COc2cc(F)cc(Oc3ccc(-c4nc([C@H]5C[C@@H](N6CCN(C)CC6)C5)n5ccnc(N)c45)cc3)c2)s1] |
| 21 | 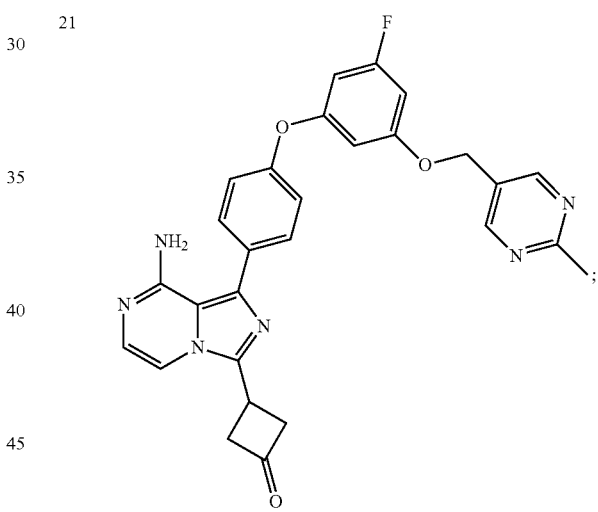 |
| 22 | 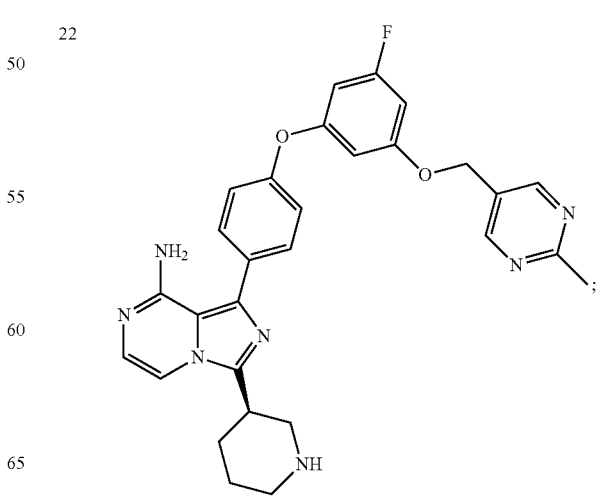 |

-continued
| Compound | Structure |
|---|---|
| 23 | 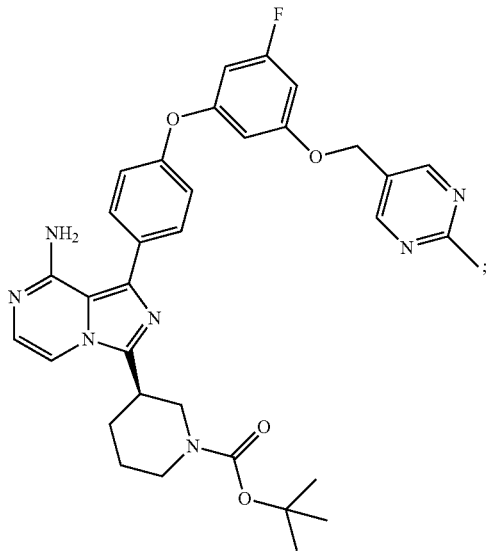 [SMILES: Cc1ncc(COc2cc(F)cc(Oc3ccc(-c4nc([C@@H]5CCCN(C(=O)OC(C)(C)C)C5)n5ccnc(N)c45)cc3)c2)cn1] |
| 24 | 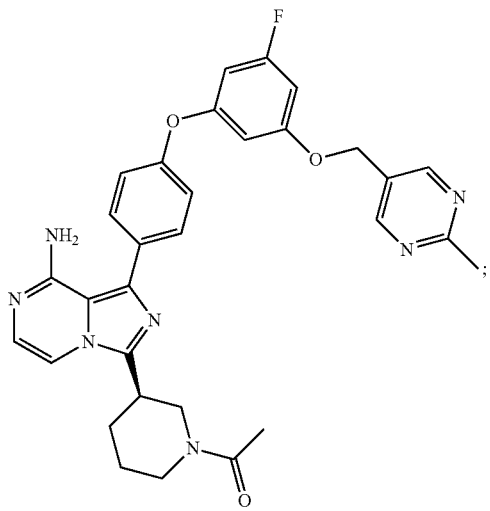 [SMILES: CC(=O)N1CCC[C@@H](c2nc(-c3ccc(Oc4cc(F)cc(OCc5cnc(C)nc5)c4)cc3)c3c(N)nccn23)C1] |
| 25 | 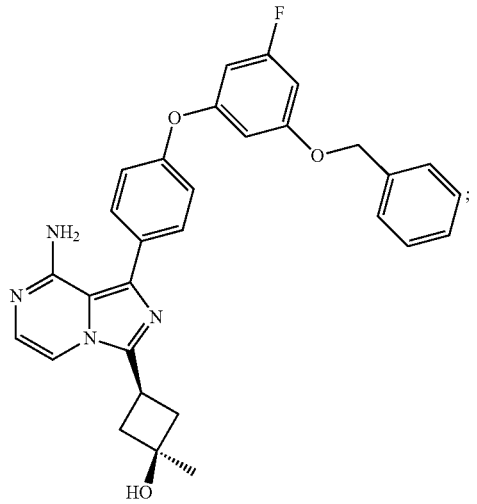 [SMILES: C[C@]1(O)C[C@@H](c2nc(-c3ccc(Oc4cc(F)cc(OCc5ccccc5)c4)cc3)c3c(N)nccn32)C1] |
-continued
| Compound | Structure |
|---|---|
| 26 | 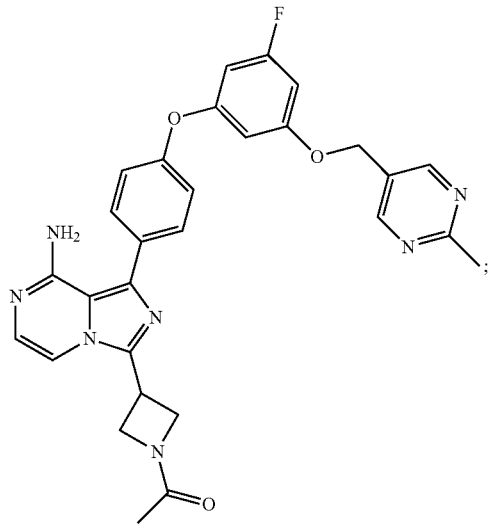 [SMILES: CC(=O)N1CC(c2nc(-c3ccc(Oc4cc(F)cc(OCc5cnc(C)nc5)c4)cc3)c3c(N)nccn23)C1] |
| 27 | 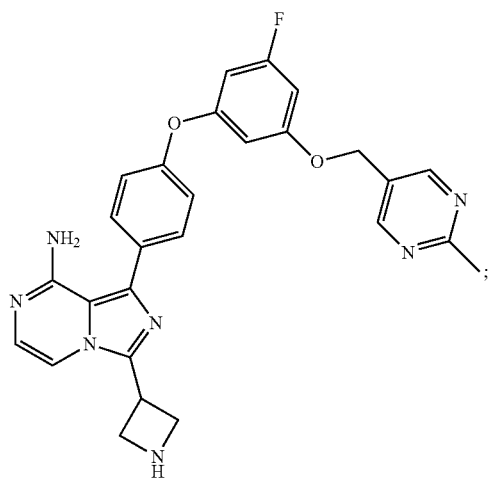 [SMILES: Cc1ncc(COc2cc(F)cc(Oc3ccc(-c4nc(C5CNC5)n5ccnc(N)c45)cc3)c2)cn1] |
| 28 | 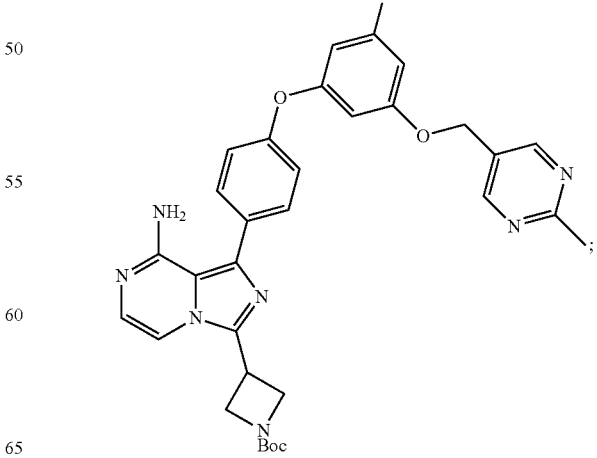 |

125
-continued
| Compound | Structure |
|---|---|
| 29 | 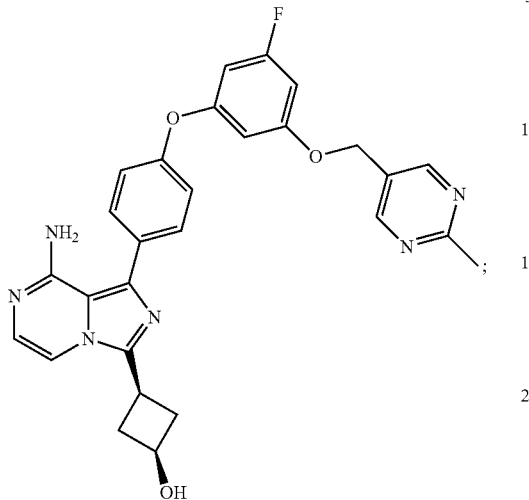 |
| 30 | 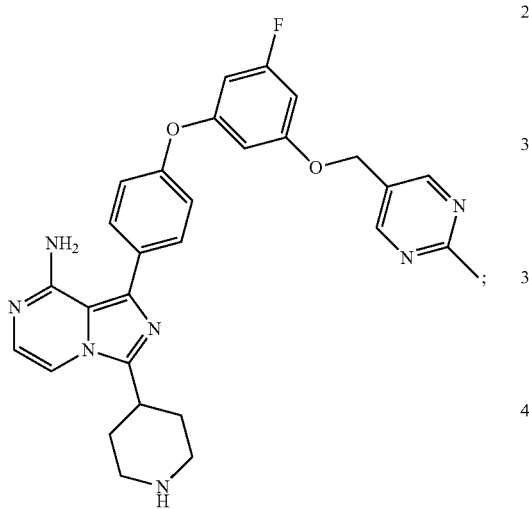 |
| 31 | 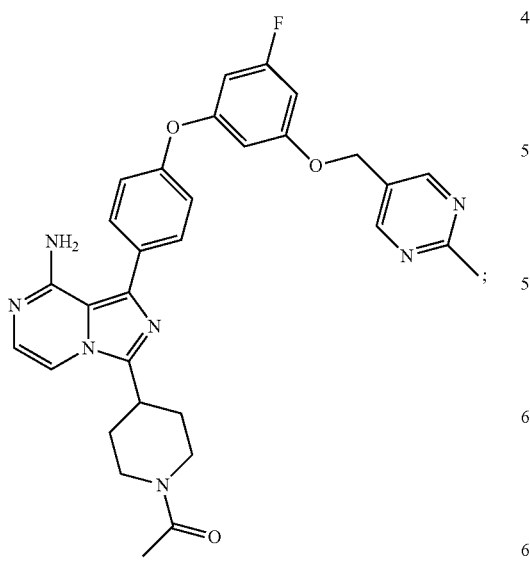 |
126
-continued
| Compound | Structure |
|---|---|
| 32 | 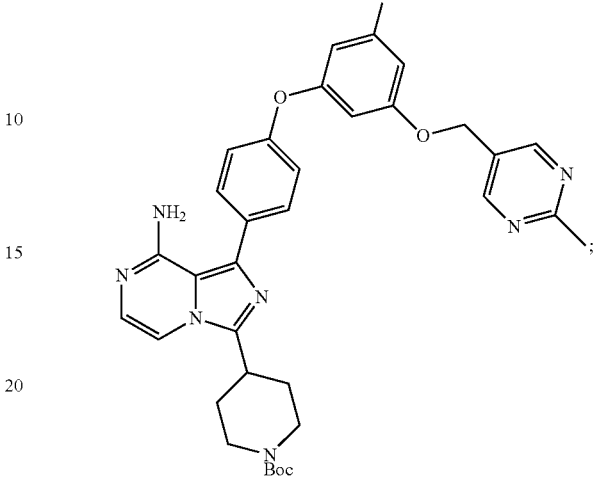 |
| 33 | 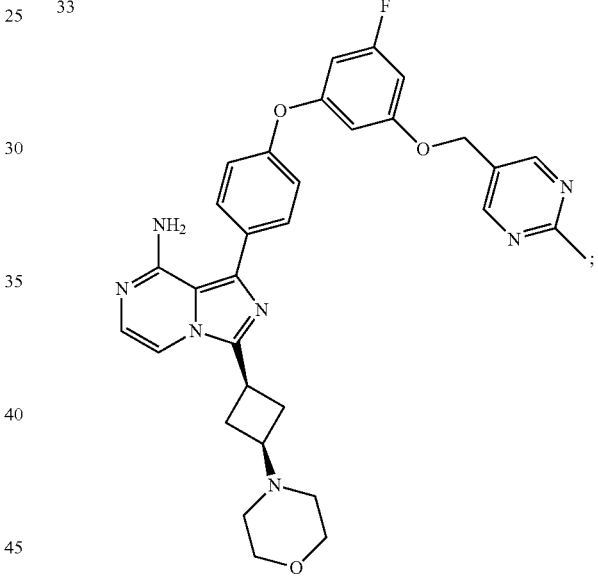 |
| 34 | 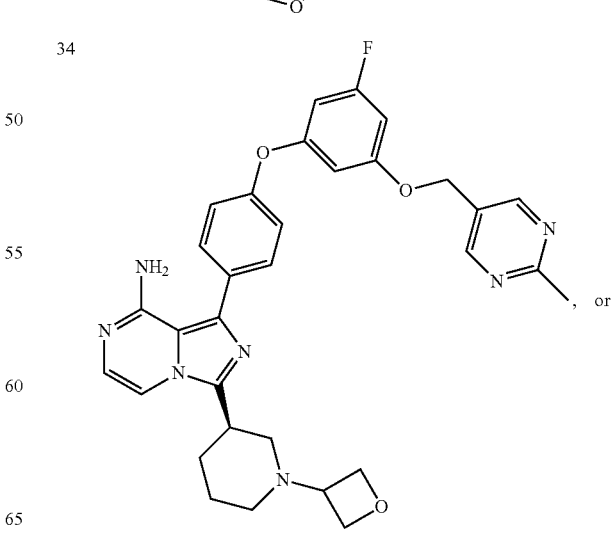, or |

| Compound | Structure |
|---|---|
| 35 | 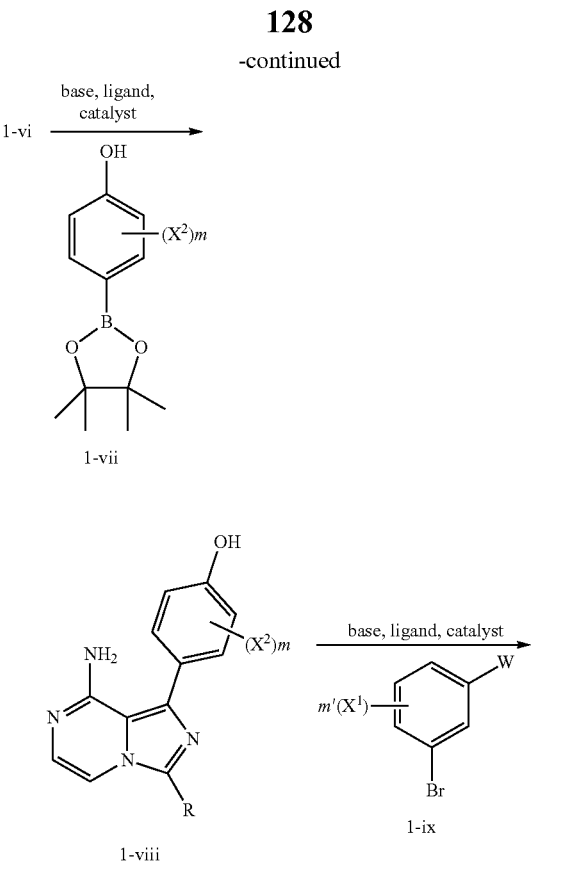 |
or pharmaceutically acceptable salt, solvate, solvate of salt, stereoisomer, tautomer, isotope, or complex thereof.
9. A process for producing a compound according to claim 1, wherein the process comprises the following steps:
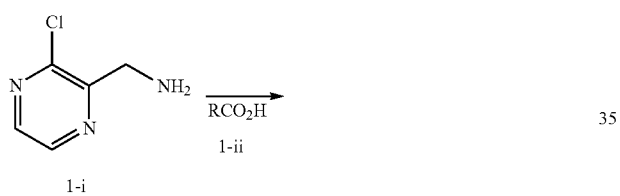
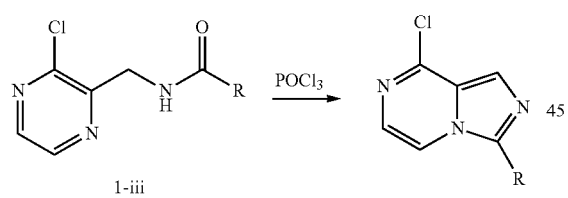
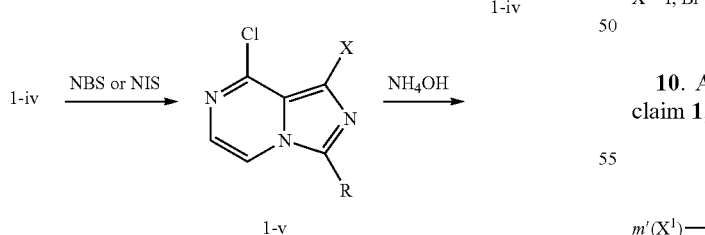
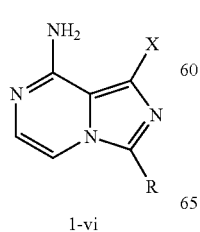
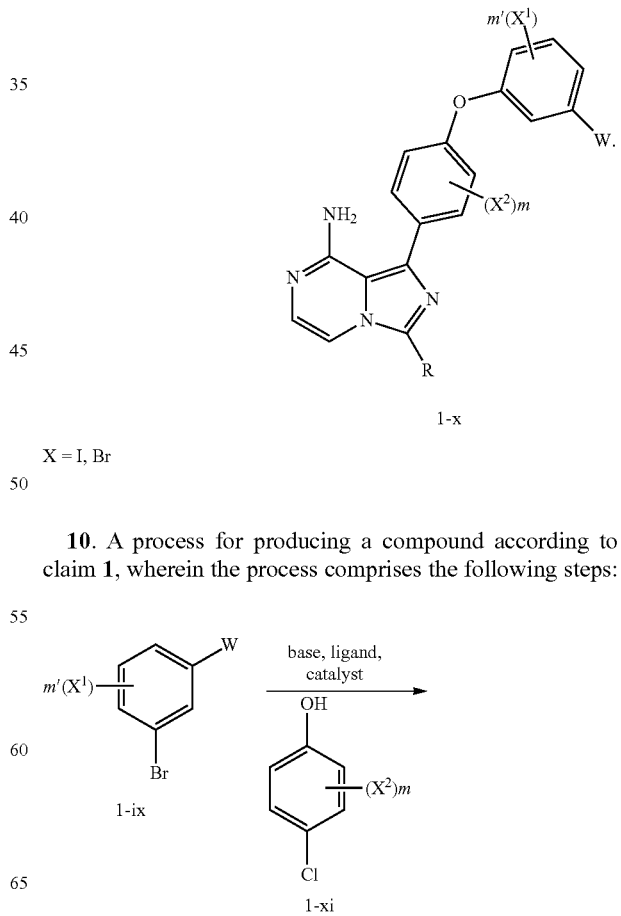
X = I, Br
10. A process for producing a compound according to claim 1, wherein the process comprises the following steps:

-continued

[structure 1-xii: m'(X¹)—phenyl(W)—O—phenyl(X²)m—Cl]

1-xii 1-xii →(base, ligand, catalyst, bis(pinacolato)diboron)→

[structure 1-xiii: m'(X¹)—phenyl(W)—O—phenyl(X²)m—Bpin]

1-xiii

[structure 1-vi: imidazopyrazine with NH₂, X, R]

1-vi + 1-xiii →(base, ligand, catalyst)→

[structure 1-x: imidazopyrazine-NH₂ substituted with biaryl ether bearing W, X¹, X²]

1-x

11. A pharmaceutical composition comprising a compound according to claim 1, or a pharmaceutically acceptable salt, solvate, solvate of salt, stereoisomer, tautomer, isotope, or complex thereof, and at least one pharmaceutically acceptable carrier, diluents, or excipient.

12. A compound of Formula I:

[Formula I: imidazo-fused ring with NH₂, X, N, R, and Y—E—Z—W substituent]

Formula I or pharmaceutically acceptable salt, solvate, solvate of salt, stereoisomer, tautomer, isotope, or complex thereof, wherein
X is
 1) CH;
R is
 1) hydrogen,
 2) alkyl,
 3) heteroalkyl,
 4) carbocyclyl,
 5) heterocyclyl,
 6) aryl, or
 7) heteroaryl,
wherein the alkyl, heteroalkyl, carbocyclyl, heterocyclyl, aryl, or heteroaryl are optionally substituted;
Y is

[phenyl with $(X^2)_m$]

;

E is oxygen;
Z is

[phenyl with $(X^1)_{m'}$]

;

W is
 1) —OCH₂R¹ or
 2) —CH$_{2OR}$¹,
wherein Y-E-Z W is

[biaryl ether: phenyl-$(X^2)_m$—O—phenyl-$(X^1)_{m'}$—W];

R¹ is substituted or unsubstituted aryl;
X¹ and X² are independently hydrogen or halogen;
m is an integer from 0 to 4;
m' is an integer from 0 to 4.

13. The compound according to claim 12, wherein R is selected from the group consisting of:

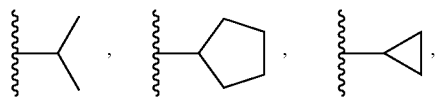

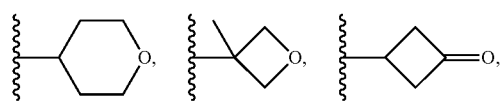

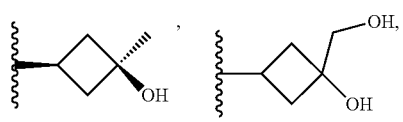

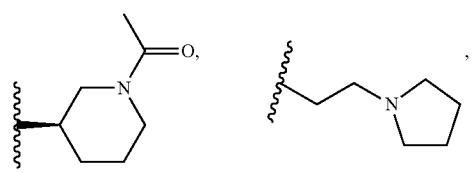

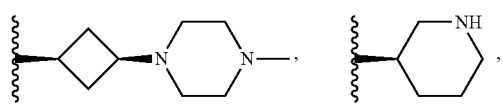

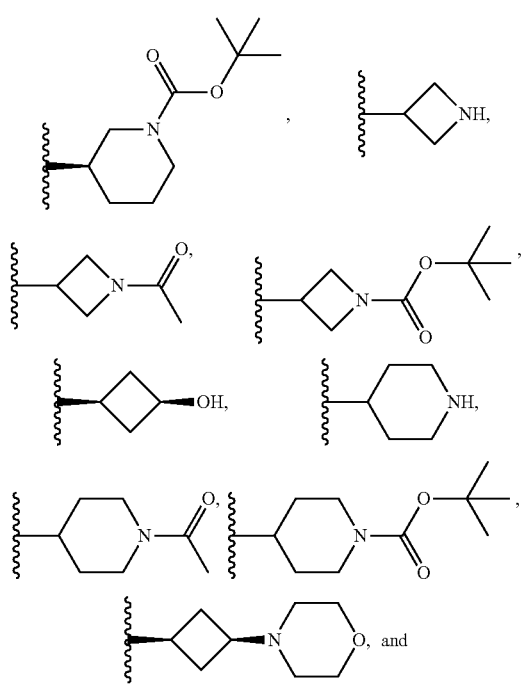

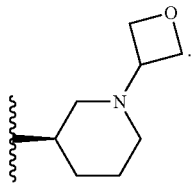

14. The compound according to claim 12, wherein Z is

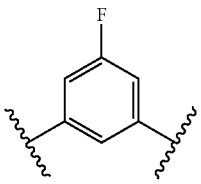

15. The compound according to claim 12, wherein Y is

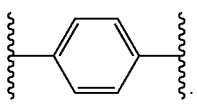

16. The compound according to claim 12, wherein W is

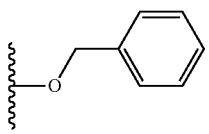

17. A compound of Formula I:

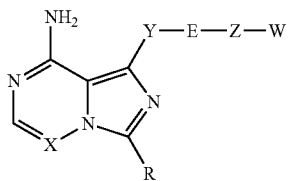

Formula I or pharmaceutically acceptable salt, solvate, solvate of salt, stereoisomer, tautomer, isotope, or complex thereof, wherein X is
1) CH;

R is
1) hydrogen,
2) alkyl,
3) heteroalkyl,
4) carbocyclyl,
5) heterocyclyl,
6) aryl, or
7) heteroaryl, wherein the alkyl, heteroalkyl, carbocyclyl, heterocyclyl, aryl, or heteroaryl are optionally substituted;
Y is

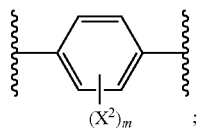

E is oxygen;
Z is

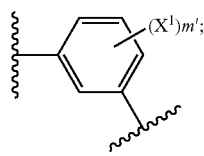

W is
1) —OCH²R¹ or
2) —CH₂OR¹,
wherein Y-E-Z-W is

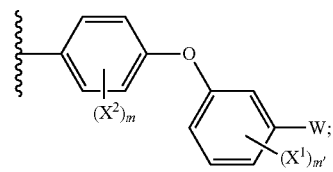

R¹ is substituted or unsubstituted 6-membered heteroaryl;
X¹ and X² are independently hydrogen or halogen;
m is an integer from 0 to 4;
m' is an integer from 0 to 4.

18. The compound according to claim 17, wherein R is selected from the group consisting of:

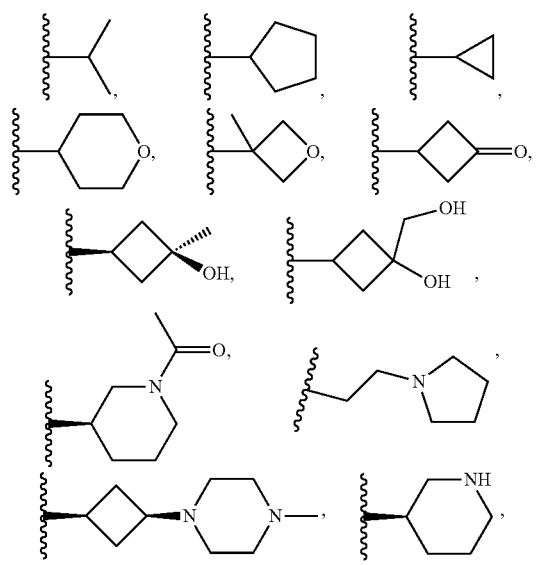

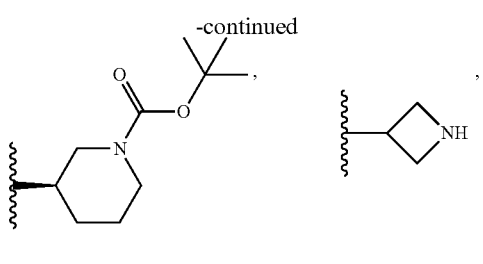

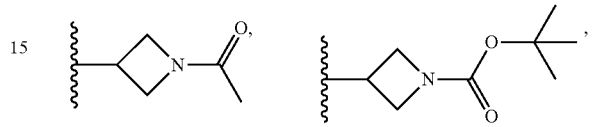

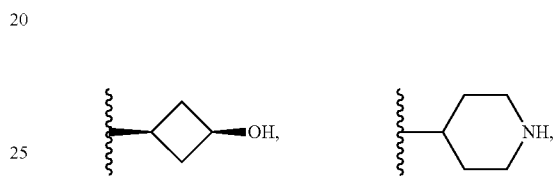

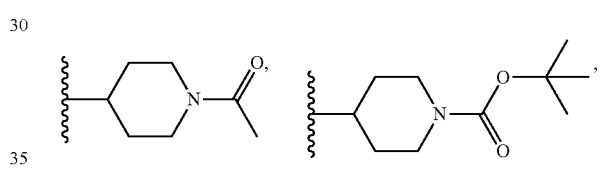

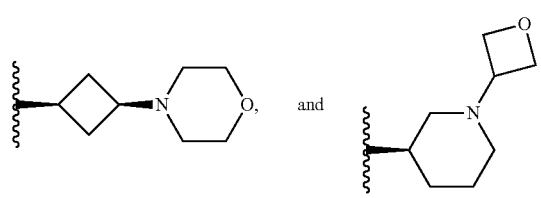

19. The compound according to claim 17, wherein Z is

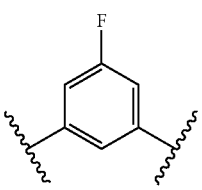

20. The compound according to claim 17, wherein Y is